United States Patent
Giacomini et al.

(10) Patent No.: US 9,217,007 B2
(45) Date of Patent: Dec. 22, 2015

(54) PLATINUM ANTICANCER AGENTS

(71) Applicant: The Regents of the University of California, Oakland, CA (US)

(72) Inventors: Kathleen M. Giacomini, Atherton, CA (US); Swati More, Minneapolis, MN (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/175,295

(22) Filed: Feb. 7, 2014

(65) Prior Publication Data

US 2014/0155366 A1    Jun. 5, 2014

Related U.S. Application Data

(63) Continuation of application No. PCT/US2012/052566, filed on Aug. 27, 2012.

(60) Provisional application No. 61/528,136, filed on Aug. 26, 2011.

(51) Int. Cl.
*C07F 15/00* (2006.01)

(52) U.S. Cl.
CPC .................................. *C07F 15/0093* (2013.01)

(58) Field of Classification Search
CPC .................................................. C07F 15/0093
See application file for complete search history.

(56) References Cited

U.S. PATENT DOCUMENTS

2010/0028259 A1    2/2010 Giacomini et al.

FOREIGN PATENT DOCUMENTS

| | | |
|---|---|---|
| JP | 5-271264 | 10/1993 |
| WO | 03017998 A1 | 3/2003 |

OTHER PUBLICATIONS

Lovejoy, Katherine S. et al., "cis-diammine(pyridine)chloroplatinum(II), a monofunctional platinum(II) antitumor agent: Uptake, structure, function, and prospects," PNAS, vol. 105(26):8902-8907 (2008).
Zhang, Shuzhong et al., "Organic Cation Transporters Are Determinants of Oxaliplatin Cytotoxicity," Cancer Res., vol. 66(17):8847-8857 (2006).

*Primary Examiner* — Brian McDowell
(74) *Attorney, Agent, or Firm* — Mintz Levin Cohn Ferris Glovsky and Popeo, P.C.

(57) ABSTRACT

Described herein are novel platinum-based compounds having the formula:

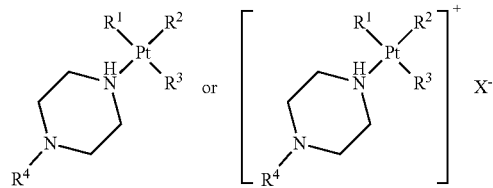

and methods of using platinum-based compounds in the treatment of diseases, such as cancer, that are associated with cells expressing solute transporter proteins.

16 Claims, 10 Drawing Sheets

PLATINUM ANTICANCER AGENTS

CROSS-REFERENCE TO RELATED APPLICATIONS

This application claims the benefit of PCT application PCT/US2012/052566, filed Aug. 27, 2012, titled "PLATINUM ANTICANCER AGENTS" and U.S. Provisional Application No. 61/528,136 filed Aug. 26, 2011, which are hereby incorporated in their entirety and for all purposes.

REFERENCE TO A "SEQUENCE LISTING," A TABLE, OR A COMPUTER PROGRAM LISTING APPENDIX SUBMITTED AS AN ASCII TEXT FILE

The Sequence Listing written in file 84850-846113_ST25.TXT, created on Aug. 27, 2012, 55,665 bytes, machine format IBM-PC, MS-Windows operating system, is hereby incorporated by reference.

BACKGROUND OF THE INVENTION

Platinum anticancer agents in the clinic today are potent and efficacious; however, they cause a large number of serious adverse effects because their activity is often not targeted at the cancer, but rather, at all body tissues with the cancerous tissue being included. This invention addresses these and other needs in the art. For example, provided herein is a means to channel the activity of a platinum anticancer agent to a cancerous tissue, thereby decreasing the potential of adverse effects.

Cancer is the second leading cause of death behind heart disease. In fact, cancer incidence and death figures account for about 10% of the U.S. population in certain areas of the United States (National Cancer Institute's Surveillance, Epidemiology, and End Results (SEER) database and Bureau of the Census statistics; see, *Harrison's Principles of Internal Medicine*, Kasper et al., 16th ed., 2005, Chapter 66). The five leading causes of cancer deaths among men are lung cancer, prostate cancer, colon and rectum cancer, pancreatic cancer, and leukemia. The five leading causes of cancer deaths among women are lung cancer, breast cancer, colon cancer, ovarian cancer, and pancreatic cancer. When detected at locally advanced or metastatic stages, no consistently curative treatment regimen exists. Treatment for metastatic cancer includes immunotherapy, hormonal ablation, radiation therapy, chemotherapy, hormonal therapy, and combination therapies. Unfortunately, for prostate cancer and hormone dependent tumors, there is frequent relapse of an aggressive androgen independent disease that is insensitive to further hormonal manipulation or to treatment with conventional chemotherapy (Ghosh et al., *Proc. Natl. Acad. Sci. U.S.A.*, 95:13182-13187 (1998)).

The organic cation transporters (OCTs), OCT1 (Grundemann et al., *Nature*, 372:549-552 (1994)), OCT2 (Okuda et al., *Biochem. Biophys. Res. Comm.*, 224:500-507 (1996)), and OCT3 (Kekuda et al., *J. Biol. Chem.*, 273:15971-15979 (1998); Wu et al., *J. Biol. Chem.*, 273:32776-32786 (1998)), are in the class of plasma membrane transporters belonging to the solute carrier (SLC) 22A family. The OCTs mediate intracellular uptake of a broad range of structurally diverse organic cations (Jonker et al., *J. Pharmacol. Exp. Ther.*, 308:2-9 (2004); Wright, *Toxicol. Appl. Pharmacol.*, 204:309-319 (2005)). Substrates of OCTs include endogenous compounds such as choline, creatinine, and monoamine neurotransmitters, and a variety of xenobiotics such as tetraethylammonium (TEA, a prototypic organic cation), 1-methyl-4-phenylpyridinium (MPP+, a neurotoxin) and clinically used drugs such as metformin, cimetidine, and amantadine (Jonker et al., supra). In humans, OCT1 is primarily expressed in the liver (Gorboulev et al., *DNA Cell Biol.*, 16:871-881 (1997); Zhang et al., *Mol. Pharmacol.*, 51:913-921 (1997); Wright, supra) and less so in the intestine (Muller et al., *Biochem. Pharmacol.*, 70:1851-1860 (2005)), whereas OCT2 is predominantly expressed in the kidney (Gorboulev et al., supra; Wright, supra). OCT3 is expressed in many tissues including placenta, heart, liver, and skeletal muscle (Grundemann et al., *Nat. Neurosci.*, 1:349-351 (1998); Verhaagh et al., *Genomics*, 55:209-218 (1999)). The expression of the OCTs has also been detected in a number of human cancer cell lines (Hayer-Zillgen et al., *Br. J. Pharmacol.*, 136:829-836 (2002)). The interaction of cisplatin with human OCTs has been investigated and the results are discordant (Briz et al., *Mol. Pharmacol.*, 61:853-860 (2002); Ciarimboli et al., *Am. J. Pathol.*, 167:1477-1484 (2005)). Previous studies indicate that cisplatin is not a substrate of human OCT1 or OCT2 (Briz et al., supra), whereas more recent work indicates that the drug interacts with human and rat OCT2 but not OCT1 (Ciarimboli et al., supra; Yonezawa et al., *Biochem. Pharmacol.*, 70:1823-1831 (2005)).

Platinum-based compounds and drugs are among the most active anticancer agents and cisplatin represents one of the three most widely used cancer chemotherapeutics (Wong et al., *Chem. Rev.*, 99:2451-2466 (1999)). Although cisplatin is effective against a number of solid tumors, especially testicular and ovarian cancer, its clinical use is limited because of its toxic effects as well as the intrinsic and acquired resistance of some tumors to this drug (Weiss et al., *Drugs*, 46:360-377 (1993)). Carboplatin is less nephrotoxic, but its cross-resistance with cisplatin limits its application in otherwise cisplatin-treatable diseases (Weiss et al., supra). Oxaliplatin, however, exhibits a different anticancer spectrum from that of cisplatin (Raymond et al., *Ann. Oncol.*, 9:1053-1071 (1998); Rixe et al., *Biochem. Pharmacol.*, 52:1855-1865 (1996)). It has been approved as the first or second line therapy in combination with 5-fluoruracil/leucovorin for advanced colorectal cancer, for which cisplatin and carboplatin are essentially inactive (Misset et al., *Crit. Rev. Oncol. Hematol.*, 35:75-93 (2000)). In spite of their distinct antitumor specificities, cisplatin and oxaliplatin exhibit cytotoxicity (Pinto et al., *Biochim. Biophys. Acta*, 780:167-180 (1985); Zamble et al., *Trends Biochem. Sci.*, 20:435-439 (1995)). These compounds may initiate a series of biochemical cascades, eventually leading to cell death (Pinto et al., supra; Wang et al., *Nat. Rev. Drug Discov.*, 4:307-320 (2005)).

Cisplatin and oxaliplatin target similar DNA sites for binding and form similar types of DNA adducts (Jennerwein et al., *Chem. Biol. Interact.*, 70:39-49 (1989); Page et al., *Biochemistry*, 29:1016-1024 (1990); Woynarowski et al., *Mol. Pharmacol.*, 54:770-777 (1998)), mainly 1,2- and 1,3-intrastrand cross-links involving purine nucleotides. Studies aiming to identify such mechanisms have focused on the cellular processing of cisplatin- and oxaliplatin-DNA adducts (Chaney et al., *Crit. Rev. Oncol. Hematol.*, 53:3-11 (2005); Vaisman et al., *Biochemistry*, 38:11026-11039 (1999)). Reduced intracellular accumulation is a common observation in cisplatin-resistant cells (Andrews et al., *Cancer Cells*, 2:35-43 (1990); Gately et al., *Br. J. Cancer,* 67:1171-1176 (1993)).

BRIEF SUMMARY OF THE INVENTION

In a first aspect, a compound having the formula:

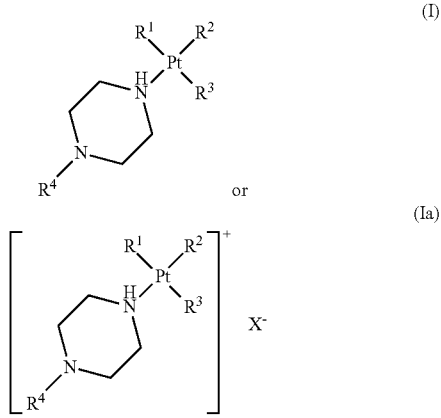

is provided.

$X^-$ is a counterion. $R^1$, $R^2$, and $R^3$ are independently halogen, —$SR^9$, —$OSO_2R^8$, —$OSO_3H$, —$NH_2NH_2$, —$ONR^6R^7$, —$NH_2C=(O)NHNH_2$, —$NH_2C=(O)NR^6R^7$, —$NR^5R^6R^7$, —$OC(O)R^8$, —$OC(O)NR^6R^7$, —$OR^9$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein $R^1$ and $R^2$, $R^2$ and $R^3$ or $R^1$ and $R^3$ may optionally be joined to form a substituted or unsubstituted cycloalkyl, substituted or unsubstituted heterocycloalkyl, substituted or unsubstituted aryl, or substituted or unsubstituted heteroaryl. $R^4$ is independently hydrogen, halogen, —$CY_3$, —$CN$, —$SO_2Cl$, —$SO_qR^{14}$, —$SO_uNR^{11}R^{12}$, $NHNH_2$, —$ONR^{11}R^{12}$, —$NHC=(O)NHNH_2$, —$NHC=(O)NR^{11}R^{12}$, —$N(O)_m$, —$NR^{11}R^{12}$, —$C(O)R^{13}$, —$C(O)$—$OR^{13}$, —$C(O)NR^{11}R^{12}$, —$OR^{14}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^5$, $R^6$, $R^7$, $R^8$, and $R^9$ are independently hydrogen, halogen, —$CF_3$, —$CN$, —$OH$, —$NH_2$, —$COOH$, —$CONH_2$, —$NO_2$, —$SH$, —$SO_2Cl$, —$SO_3H$, —$SO_4H$, —$SO_2NH_2$, —$NHNH_2$, —$ONH_2$, —$NHC=(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^{11}$, $R^{12}$, $R^{13}$, and $R^{14}$ are independently hydrogen, halogen, —$CF_3$, —$CN$, —$OH$, —$NH_2$, —$COOH$, —$CONH_2$, —$NO_2$, —$SH$, —$SO_2Cl$, —$SO_3H$, —$SO_4H$, —$SO_2NH_2$, —$NHNH_2$, —$ONH_2$, —$NHC=(O)NHNH_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. The symbol u is independently an integer from 1 to 2. The symbol m is independently an integer from 1 to 2. The symbol q is independently an integer from 0 to 4. The symbol Y is independently —Cl, —Br, —I, or —F.

In a second aspect, a pharmaceutical composition including a pharmaceutically acceptable excipient and a compound as described herein (e.g. formula I, Ia, II, IIa, III, IIIa, IV, or V, including embodiments), or a pharmaceutically acceptable salt of a compound described herein is provided.

In another aspect, a method of inhibiting replication of DNA in a cell is provided. The method includes contacting the cell with a compound as described herein (e.g. formula I, Ia, II, IIa, III, IIIa, IV, or V, including embodiments).

In a further aspect, a method of inducing cell death in a cell is provided. The method includes contacting the cell with a compound as described herein (e.g. formula I, Ia, II, IIa, III, IIIa, IV, or V, including embodiments).

In a further aspect, a method of treating a disease in a patient in need of such treatment is provided, wherein the patient has disease-related cells expressing a norepinephrine transporter protein or mRNA. The method includes administering a therapeutically effective amount of a compound as described herein (e.g. formula I, Ia, II, IIa, III, IIIa, IV, or V, including embodiments).

In a further aspect, a method of inhibiting replication of DNA in a cell is provided, wherein the cell expresses a norepinephrine transporter protein or mRNA. The method includes contacting the cell with a compound as described herein (e.g. formula I, Ia, II, IIa, III, IIIa, IV, or V, including embodiments).

In a further aspect, a method of inducing cell death in a cell, wherein the cell expresses a norepinephrine transporter protein or mRNA is provided. The method includes contacting the cell with a compound as described herein (e.g. formula I, Ia, II, IIa, III, IIIa, IV, or V, including embodiments).

DETAILED DESCRIPTION OF THE INVENTION

I. Definitions

Figure 1:
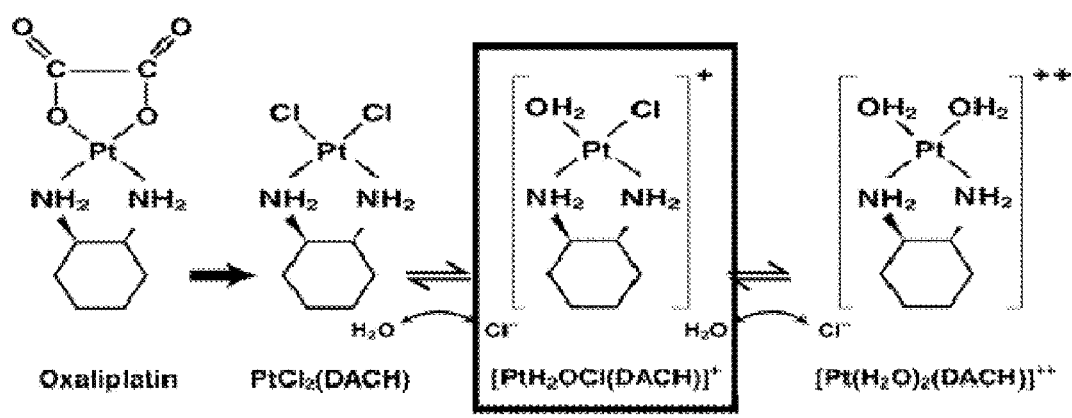
FIG. 1. Bioconversion of oxaliplatin to mono- and diaqua intermediates.
Figure 2:
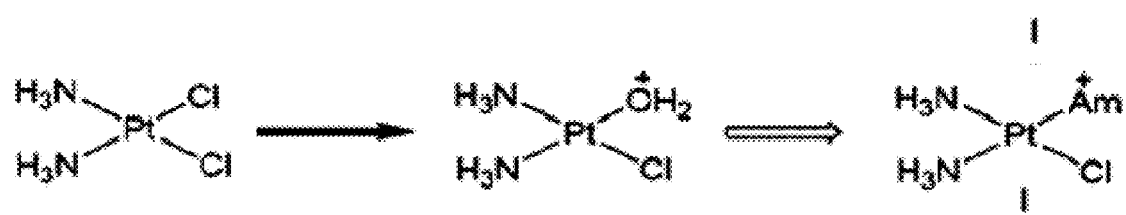
FIG. 2. Example of certain Class A compounds: Am is a platinum ligand such as a substituted or unsubstituted piperazinyl.
Figure 3:
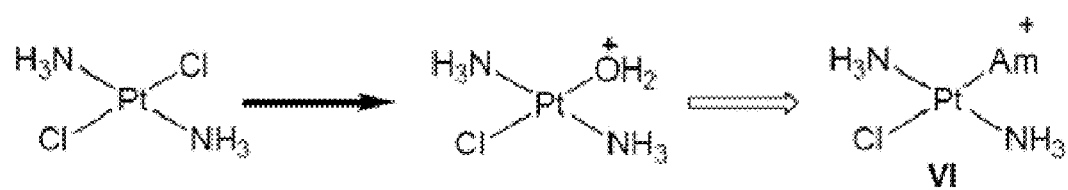
FIG. 3. Example of certain Class C compounds: Am is a platinum ligand such as a substituted or unsubstituted piperazinyl.
Figure 4:
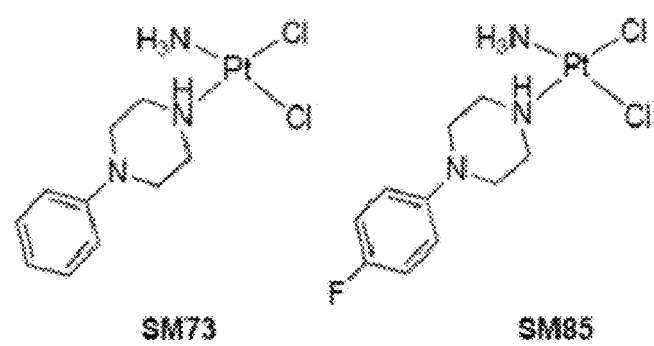
FIG. 4 depicts a set of two platinum compounds SM-73 and SM-85.

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include di- and multivalent radicals, having the number of carbon atoms designated (i.e., $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, (cyclohexyl) methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—).

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom selected from the group consisting of Pt, O, N, P, Si, and S, and wherein the nitrogen and sulfur atoms may optionally be oxidized, and the nitrogen heteroatom may optionally be quaternized. The heteroatom(s) Pt, O, N, P, S, and Si may be placed at any interior position of the heteroalkyl group or at the position at which the alkyl group is attached to the remainder of the molecule. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, —O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$.

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as Pt, N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroaryl refers to two rings fused together, wherein one ring has 5 members and the other ring has 6 members, and wherein at least one ring is a heteroaryl ring. Likewise, a 6,6-fused ring heteroaryl refers to two rings fused together, wherein one ring has 6 members and the other ring has 6 members, and wherein at least one ring is a heteroaryl ring. And a 6,5-fused ring heteroaryl refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4- oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively.

A fused ring heterocycloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substituents described herein.

The term "oxo," as used herein, means an oxygen that is double bonded to a carbon atom.

The term "alkylsulfonyl," as used herein, means a moiety having the formula —S($O_2$)—R', where R' is an alkyl group as defined above, including substituted or unsubstituted. R' may have a specified number of carbons (e.g., "$C_1$-$C_4$ alkylsulfonyl").

Each of the above terms (e.g., "alkyl," "heteroalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R"', —OC(O)R', —C(O)R', —$CO_2$R', —CONR'R", —OC(O)NR'R", —NR"C(O)R', —NR'—C(O) NR"R"', —NR"C(O)$_2$R', —NR—C(NR'R"R"')=NR"", —NR—C(NR'R")=NR"', —S(O)R', —S(O)$_2$R', —S(O)$_2$ NR'R", —NRSO$_2$R', —NR'NR"R"', —ONR'R", —NR'C=(O)NR"NR"'R"", —CN, —$NO_2$, in a number ranging from zero to (2 m'+1), where m' is the total number of carbon atoms in such radical. R, R', R", R"', and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound of the invention includes more than one R group, for example, each of the R groups is independently selected as are each R', R", R"', and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —C(O) $CH_3$, —C(O)$CF_3$, —C(O)$CH_2OCH_3$, and the like).

Similar to the substituents described for the alkyl radical, substituents for the aryl and heteroaryl groups are varied and are selected from, for example: —OR', —NR'R", —SR', -halogen, —SiR'R"R"', —OC(O)R', —C(O)R', —$CO_2$R', —CONR'R", —OC(O)NR'R", —NR"C(O)R', —NR'—C(O) NR"R"', —NR"C(O)$_2$R', —NR—C(NR'R"R"')=NR"", —NR—C(NR'R")=NR"', —S(O)R', —S(O)$_2$R', —S(O)$_2$ NR'R", —NRSO$_2$R', —NR'NR"R"', —ONR'R", —NR'C=(O)NR"NR"'R"", —CN, —$NO_2$, —R', —$N_3$, —CH(Ph)$_2$, fluoro($C_1$-$C_4$)alkoxy, and fluoro($C_1$-$C_4$)alkyl, in a number ranging from zero to the total number of open valences on the aromatic ring system; and where R', R", R"', and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R", R"', and R"" groups when more than one of these groups is present.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-($CH_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R"')$_d$—, where s and d are independently integers of from 0 to 3, and X' is —O—, —NR'—, —S—, —S(O)—, —S(O)$_2$—, or —S(O)$_2$NR'—. The substituents R, R', R", and R"' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include, oxygen (O), nitrogen (N), sulfur (S), phosphorus (P), and silicon (Si).

A "substituent group," as used herein, means a group selected from the following moieties:

(A) —OH, —$NH_2$, —SH, —CN, —$CF_3$, —$NO_2$, oxo, halogen, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:

(i) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from:

(a) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, or heteroaryl, substituted with at least one substituent selected from: oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_4$-C$_8$ cycloalkyl, and each substituted or unsubstituted heterocycloalkyl is a substituted or unsubstituted 4 to 8 membered heterocycloalkyl.

A "lower substituent" or "lower substituent group," as used herein, means a group selected from all of the substituents described above for a "substituent group," wherein each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_3$-C$_7$ cycloalkyl, and each substituted or unsubstituted heterocycloalkyl is a substituted or unsubstituted 3 to 7 membered heterocycloalkyl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. Alternatively, at least one or all of these groups are substituted with at least one lower substituent group.

In other embodiments of the compounds herein, each substituted or unsubstituted alkyl may be a substituted or unsubstituted C$_1$-C$_{20}$ alkyl, each substituted or unsubstituted heteroalkyl is a substituted or unsubstituted 2 to 20 membered heteroalkyl, each substituted or unsubstituted cycloalkyl is a substituted or unsubstituted C$_3$-C$_8$ cycloalkyl, and/or each substituted or unsubstituted heterocycloalkyl is a substituted or unsubstituted 3 to 8 membered heterocycloalkyl. In some embodiments of the compounds herein, each substituted or unsubstituted alkylene is a substituted or unsubstituted C$_1$-C$_{20}$ alkylene, each substituted or unsubstituted heteroalkylene is a substituted or unsubstituted 2 to 20 membered heteroalkylene, each substituted or unsubstituted cycloalkylene is a substituted or unsubstituted C$_3$-C$_8$ cycloalkylene, and/or each substituted or unsubstituted heterocycloalkylene is a substituted or unsubstituted 3 to 8 membered heterocycloalkylene.

In some embodiments, each substituted or unsubstituted alkyl is a substituted or unsubstituted C$_1$-C$_8$ alkyl, each substituted or unsubstituted heteroalkyl is a substituted or unsubstituted 2 to 8 membered heteroalkyl, each substituted or unsubstituted cycloalkyl is a substituted or unsubstituted C$_5$-C$_7$ cycloalkyl, and/or each substituted or unsubstituted heterocycloalkyl is a substituted or unsubstituted 5 to 7 membered heterocycloalkyl. In some embodiments, each substituted or unsubstituted alkylene is a substituted or unsubstituted C$_1$-C$_8$ alkylene, each substituted or unsubstituted heteroalkylene is a substituted or unsubstituted 2 to 8 membered heteroalkylene, each substituted or unsubstituted cycloalkylene is a substituted or unsubstituted C$_5$-C$_7$ cycloalkylene, and/or each substituted or unsubstituted heterocycloalkylene is a substituted or unsubstituted 5 to 7 membered heterocycloalkylene. In some embodiments, the compound is a chemical species set forth in the Examples section below.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science,* 1977, 66, 1-19). Certain specific compounds of the present invention contain both basic and acidic functionalities that allow the compounds to be converted into either base or acid addition salts.

Thus, the compounds of the present invention may exist as salts, such as with pharmaceutically acceptable acids. The present invention includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

In addition to salt forms, the present invention provides compounds, which are in a prodrug form. Prodrugs of the compounds described herein are those compounds that undergo chemical changes under physiological conditions to provide the compounds of the present invention. Additionally, prodrugs can be converted to the compounds of the present invention by chemical or biochemical methods in an ex vivo environment. For example, prodrugs can be converted to the compounds of the present invention when placed in a transdermal patch reservoir with a suitable enzyme or chemical reagent. In some embodiments, prodrugs of the compounds described herein (also referred to herein as "compound of the present invention") (e.g. formula I, Ia, II, IIa, III, IIIa, IV, or V, including embodiments) may be platinum (IV)-based compounds (e.g. Pt(IV) complexes) that are converted to platinum (II)-based compounds (e.g. Pt(II) complexes) as described herein (e.g. formula I, Ia, II, IIa, III, IIIa, IV, or V, including embodiments). In some embodiments, the platinum (IV)-based compound is bonded to two additional groups as well as the four ligands (also referred to herein as substituents) of the platinum (II)-based compounds described herein (e.g. formula I, Ia, II, IIa, III, IIIa, IV, or V, including embodiments). In some embodiments, the two ligands present in a platinum (IV)-based compound that are lost when converting to the corresponding platinum (II)-based compound is a platinum (IV)-based compound leaving group known in the art such as a halogen (e.g. chloride, bromide, iodide). (see, for example, Talman et al., "Can Pt(IV)-amine complexes act as 'prodrugs'?", $\textit{Inorganica Chimica Acta}$, 1998, 283, 251-255; Choi et al., "Reduction and Anticancer Activity of Platinum(IV) Complexes", $\textit{Inorganic Chemistry}$, 1998, 37, 2500-2504; Dhar et al., "Targeted delivery of a cisplatin prodrug for safer and more effective prostate cancer therapy in vivo", 2011, 108, 1850-1855). Generating Pt(IV)-based compound prodrugs of novel Pt(II)-based compounds and methods of using the prodrugs are within the capabilities of one skilled in the art (Id.)

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

As used herein, the term "salt" refers to acid or base salts of the compounds used in the methods of the present invention. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^{3}$H), iodine-125 ($^{125}$I), or carbon-14 ($^{14}$C). All isotopic variations of the compounds of the present invention, whether radioactive or not, are encompassed within the scope of the present invention.

The symbol "$\sim\!\sim\!\sim$" denotes the point of attachment of a chemical moiety to the remainder of a molecule or chemical formula.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487-493 (1991) and Houghton et al., *Nature* 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909-6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer. Chem. Soc.* 114:9217-9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., *Nature Biotechnology*, 14(3):309-314 (1996) and PCT/US96/10287), carbohydrate libraries (see, e.g., Liang et al., *Science,* 274:1520-1522 (1996) and U.S. Pat. No. 5,593,853). The methods above may be used to synthesize single molecular species.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls. Moreover, where a moiety is substituted with an R substituent, the group may be referred to as "R-substituted." Where a moiety is R-substituted, the moiety is substituted with at least one R substituent and each R substituent is optionally different.

Description of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The term "counterion" as used herein means an ion with a charge of opposite polarity from a compound (e.g. a positively charged compound and a negatively charged counterion) with which it interacts. Counterions include those anions derived from inorganic acids such as hydrochloric (e.g. $Cl^-$), hydrobromic (e.g. $Br^-$), nitric (e.g. $NO_3^-$), carbonic, monohydrogencarbonic, phosphoric, monohydrogenphosphoric, dihydrogenphosphoric, sulfuric, monohydrogensulfuric, hydriodic, or phosphorous acids and the like, as well as the anions derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are anions of amino acids such as arginate and the like, and salts of organic acids like glucuronic or galactunoric acids and the like. In some embodiments, a counterion is acetate, bromide, camsylate, chloride, formate, fumarate, maleate, mesylate, nitrate, oxalate, phosphate, sulfate, tartrate, thiocyanate, or tosylate.

The term "ligand" has its plain ordinary meaning within chemistry and inorganic chemistry and is well understood by those of ordinary skill in the art. The term "ligand" is used interchangeably with "substituent" in the context of a group bound to a platinum atom. In some embodiments, a ligand is bonded to a platinum atom through a coordinate covalent bond. Without being limited by theory or mechanism, it would be understood by one of ordinary skill in the art that a ligand may contribute a lone pair of electrons to the bond with a platinum atom, resulting in the formation of the bond (e.g. coordinate bond or coordinate covalent bond). In some embodiments, the donor atom of the ligand group is neutral. In some embodiments, the donor atom of the ligand group is charged.

The term "donor atom" is given its plain ordinary meaning within chemistry and inorganic chemistry and would be understood by a person of skill in the art. In some embodiments, the donor atom is the atom of the ligand or substituent group that contributes a lone pair of electrons to form the bond with a platinum atom in a platinum-based compound. In some embodiments, the donor atom is a heteroatom. In some embodiments, the donor atom is not a carbon atom.

The term "transporter" or "transporter protein" as used herein refers to a protein capable of transporting certain molecules across a membrane (e.g. a cell membrane). Examples of transporters include the solute carrier family of transporter proteins. Within the solute carrier family of transporter proteins are the sodium- and chloride-dependent sodium:neurotransmitter transporters (SLC6), which includes NET. Within the solute carrier family of transporter are the oraganic cation/anion/zwitterion transporters (SLC22), which include OCT1, OCT2, and OCT3.

The term "transporter substrate" as used herein means a composition (e.g. compound, platinum-based compound or drug) capable of being transported into a cell by a transporter protein. An "organic cation transporter substrate" means a composition (e.g. compound or platinum-based compound or drug) capable of being transported into a cell by an organic cation transporter (OCT). A "norepinephrine transporter substrate" is a composition (e.g. compound or platinum-based compound or drug) capable of being transported into a cell by a norepinephrine transporter.

The term "modulator" refers to a composition that increases or decreases the level of a target molecule or the function of a target molecule (e.g. a target may be a transporter protein and the function may be to translocate a molecule across a membrane or a target may be a cancer cell and the function may be to replicate and multiply). In some embodiments, a modulator is a compound that reduces the severity of one or more symptoms of a disease (e.g. tumor growth or metastasis).

The term "platinum-based compound" as used herein refers to a compound comprising a heavy metal complex containing a central atom of platinum surrounded by organic and/or inorganic functionalities (e.g. formula I, Ia, II, IIa, III, IIIa, IV, or V, including embodiments). Non-limiting examples of platinum-based compounds include oxaliplatin, cisplatin, carboplatin, pharmaceutically acceptable salts thereof, stereoisomers thereof, derivatives thereof, analogs thereof, and combinations thereof. Included within platinum-based compounds are platinum-based drugs.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine. and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with material as a carrier providing a dosage form in which the active component with or without other carriers, is associated with a carrier. Similarly, cachets and lozenges are included. Tablets, powders, capsules, pills, cachets, and lozenges can be used as solid dosage forms suitable for oral administration.

The terms "treating" or "treatment" refers to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. For example, the certain methods presented herein successfully treat cancer by decreasing the incidence of cancer and or causing remission of cancer. The term "treating," and conjugations thereof, include prevention of an injury, pathology, condition, or disease.

An "effective amount" is an amount sufficient to accomplish a stated purpose (e.g. achieve the effect for which it is administered, treat a disease, reduce enzyme activity, kill a cancer cell, reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy,* 20th Edition, 2003, Gennaro, Ed., Lippincott, Williams & Wilkins).

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects.

"Contacting" is used in accordance with its plain ordinary meaning and refers to the process of allowing at least two distinct species (e.g. chemical compounds including biomolecules, or cells) to become sufficiently proximal to react, interact or physically touch. It should be appreciated, however, the resulting reaction product can be produced directly from a reaction between the added reagents or from an intermediate from one or more of the added reagents which can be produced in the reaction mixture.

The term "contacting" may include allowing two species to react, interact, or physically touch, wherein the two species may be a platinum-based compound as described herein and an organic cation transporter or a platinum based compound as described herein and a norepinephrine transporter or a platinum-based compound as described herein and a transporter of the solute carrier group of membrane transport proteins. In some embodiments, contacting may involve a platinum-based compound as described herein and a DNA strand, DNA base, or DNA nucleotide.

As defined herein, the term "inhibition", "inhibit", "inhibiting" and the like in reference to a protein-inhibitor interaction means negatively affecting (e.g. decreasing) the activity or function of the protein (e.g. an organic cation transporter such as OCT1, OCT2, or OCT3. or a norepinephrine transporter such as NET) relative to the activity or function of the protein in the absence of the inhibitor. Thus, inhibition includes, at least in part, partially or totally blocking stimulation, decreasing, preventing, or delaying activation, or inactivating, desensitizing, or down-regulating signal transduction or enzymatic activity. Similarly an "inhibitor" is a compound that inhibits DNA replication or induces cell death, e.g., by binding, partially or totally blocking stimulation, decrease, prevent, or delay activation, or inactivate, desensitize, or down-regulate signal transduction or enzymatic activity necessary for DNA replication cell viability or cell survival. Inhibition may also include partially or totally blocking cancer cell growth or decreasing the rate of cell or tumor growth.

"Patient" or "subject in need thereof" refers to a living organism suffering from or prone to a condition that can be treated by administration of a pharmaceutical composition as provided herein. Non-limiting examples include humans, other mammals (e.g. mice, rats, dogs, monkeys, cows, goats, sheep) and other non-mammalian animals. In some embodiments, a patient or subject in need thereof is a human with a disease or condition.

The terms "disease" or "condition" or "disorder" refer to a state of being or health status of a patient or subject capable of being treated with the compounds or methods provided herein. In some embodiments, the disease is a disease related to (e.g. caused by) an abnormal cell growth or abnormal protein activity. Examples of diseases, disorders, or conditions include, but are not limited to, cancer, metastatic cancer, acute lung injury, pulmonary vascular permeability, vascular permeability, sepsis, pain, cardiovascular disease, hypertension, Syndrome X, depression, anxiety, glaucoma, human immunodeficiency virus (HIV) or acquired immunodeficiency syndrome (AIDS), neurodegeneration, Alzheimer's disease, Parkinson's disease, cognition enhancement, Cushing's Syndrome, Addison's Disease, osteoporosis, frailty, muscle frailty, inflammatory diseases, osteoarthritis, rheumatoid arthritis, asthma and rhinitis, adrenal function-related ailments, viral infection, immunodeficiency, immunomodulation, autoimmune diseases, allergies, wound healing, compulsive behavior, multi-drug resistance, addiction, psychosis, anorexia, cachexia, post-traumatic stress syndrome, post-surgical bone fracture, medical catabolism, major psychotic depression, mild cognitive impairment, psychosis, dementia, hyperglycemia, stress disorders, antipsychotic induced weight gain, delirium, cognitive impairment in depressed patients, cognitive deterioration in individuals with Down's syndrome, psychosis associated with interferon-alpha therapy, chronic pain, pain associated with gastroesophageal reflux disease, postpartum psychosis, postpartum depression, neurological disorders in premature infants, migraine headaches, stroke, aneurysm, brain aneurysm, cerebral aneurysm, brain attack, cerebrovascular accident, ischemia, thrombosis, arterial embolism, hemorrhage, transient ischemic attack, anemia, embolism, systemic hypoperfusion, venous thrombosis, arthritis, reperfusion injury, skin diseases or conditions, acne, acne vulgaris, keratosis pilaris, acute, promyelocytic leukemia, baldness, acne rosacea, harlequin ichthyosis, xeroderma pigmentosum, keratoses, neuroblastoma, fibrodysplasia ossificans progressive, eczema, rosacea, sun damage, wrinkles, or cosmetic conditions. In some instances, "disease" or "condition" refer to cancer. In some further instances, "cancer" refers to human cancers and carcinomas, sarcomas, adenocarcinomas, lymphomas, leukemias, etc., including solid and lymphoid cancers, kidney, breast, lung, bladder, colon, ovarian, prostate, pancreas, stomach, brain, head and neck, skin, uterine, testicular, glioma, esophagus, and liver cancer, including hepatocarcinoma, lymphoma, including B-acute lymphoblastic lymphoma, non-Hodgkin's lymphomas (e.g., Burkitt's, Small Cell, and Large Cell lymphomas), Hodgkin's lymphoma, leukemia (including AML, ALL, and CML), or multiple myeloma.

As used herein, the term "autoimmune disease" refers to a disease or condition in which a subject's immune system irregularly responds to one or more components (e.g. biomolecule, protein, cell, tissue, organ, etc.) of the subject. In some embodiments, an autoimmune disease is a condition in which the subject's immune system irregularly reacts to one or more components of the subject as if such components were not self Exemplary autoimmune diseases that may be treated with a compound or method provided herein include Acute Disseminated Encephalomyelitis (ADEM), Acute necrotizing hemorrhagic leukoencephalitis, Addison's disease, Agammaglobulinemia, Asthma, Allergic asthma, Allergic rhinitis, Alopecia greata, Amyloidosis, Ankylosing spondylitis, Anti-GBM/Anti-TBM nephritis, Antiphospholipid syndrome (APS), Arthritis, Autoimmune aplastic anemia, Autoimmune dysautonomia, Autoimmune hepatitis, Autoimmune hyperlipidemia, Autoimmune immunodeficiency, Autoimmune inner ear disease (AIED), Autoimmune myocarditis, Autoimmune pancreatitis, Autoimmune retinopathy, Autoimmune thrombocytopenic purpura (ATP), Autoimmune thyroid disease, Axonal & neuronal neuropathies, Balo disease, Behcet's disease, Bullous pemphigoid, Cardiomyopathy, Castleman disease, Celiac sprue, Chagas disease, Chronic inflammatory demyelinating polyneuropathy (CIDP), Chronic recurrent multifocal osteomyelitis (CRMO), Churg-Strauss syndrome, Cicatricial pemphigoid/benign mucosal pemphigoid, Crohn's disease, Cogans syndrome, Cold agglutinin disease, Congenital heart block, Coxsackie myocarditis, CREST disease, Essential mixed cryoglobulinemia, Demyelinating neuropathies, Dermatitis herpetiformis, Dermatomyositis, Devic's disease (neuromyelitis optica), Discoid lupus, Dressler's syndrome, Endometriosis, Eosinophilic fasciitis, Erythema nodosum, Experimental allergic encephalomyelitis, Evans syndrome, Fibrosing alveolitis, Giant cell arteritis (temporal arteritis), Glomerulonephritis, Goodpasture's syndrome, Graves' disease, Grave's ophthalmopathy, Guillain-Barre syndrome, Hashimoto's encephalitis, Hashimoto's thyroiditis, Hemolytic anemia, Henoch-Schonlein purpura, Herpes gestationis, Hypogammaglobulinemia, Ichthyosis, Idiopathic thrombocytopenic purpura (ITP), IgA nephropathy, IgG4-related sclerosing disease, Immunoregulatory lipoproteins, Inclusion body myositis, Inflammatory bowel disease, Insulin-dependent diabetes (type1), Interstitial cystitis, Juvenile arthritis, Juvenile diabetes, Kawasaki syndrome, Lambert-Eaton syndrome, Leukocytoclastic vasculitis, Lichen planus, Lichen sclerosus, Ligneous conjunctivitis, Linear IgA disease (LAD), Lupus (SLE), Lyme disease, chronic, Meniere's disease, Microscopic polyangiitis, Mixed connective tissue disease (MCTD), Mooren's ulcer, Mucha-Habermann disease, Multiple sclerosis, Myasthenia gravis, Myositis, Narcolepsy, Neuromyelitis optica (Devic's), Neutropenia, Ocular cicatricial pemphigoid, Optic neuritis, Palindromic rheumatism, PANDAS (Pediatric Autoimmune Neuropsychiatric Disorders Associated with Streptococcus), Paraneoplastic cerebellar degeneration, Paroxysmal nocturnal hemoglobinuria (PNH), Parry Romberg syndrome, Parsonnage-Turner syndrome, Pars planitis (peripheral uveitis), Pemphigus, Peripheral neuropathy, Perivenous encephalomyelitis, Pernicious anemia, POEMS syndrome, Polyarteritis nodosa, Type I, II, & III autoimmune polyglandular syndromes, Polymyalgia rheumatic, Polymyositis, Postmyocardial infarction syndrome, Postpericardiotomy syndrome, Progesterone dermatitis, Primary biliary cirrhosis, Primary sclerosing cholangitis, Psoriasis, Psoriatic, arthritis, Idiopathic pulmonary fibrosis, Pyoderma gangrenous, Pure red cell aplasia, Raynauds phenomenon, Reflex sympathetic dystrophy, Reiter's syndrome, Relapsing polychondritis, Restless legs syndrome, Retroperitoneal Fibrosis, Rheumatic fever, Rheumatoid arthritis, Sarcoidosis, Schmidt syndrome, Scleritis, Scleroderma, Sjogren's syndrome, Sperm & testicular autoimmunity, Stiff person syndrome, Subacute bacterial endocarditis (SBE), Susac's syndrome, Sympathetic ophthalmia, Takayasu's arteritis, Temporal arteritis/Giant cell arteritis, Thrombocytopenic purpura (TTP), Tolosa-Hunt syndrome, Transverse myelitis, Ulcerative colitis, Undifferentiated connective tissue disease (UCTD), Uveitis, Vasculitis, Vesiculobullous dermatosis, Vitiligo, or Wegener's granulomatosis.

As used herein, the term "inflammatory disease" refers to any disease characterized by abnormal inflammation. Exemplary inflammatory diseases that may be treated with a compound or method provided herein include arthritis, rheumatoid arthritis, psoriatic arthritis, juvenile idiopathic arthritis, multiple sclerosis, systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, auto-immune thyroiditis, Behcet's disease, Crohn's disease, ulcerative colitis, bullous pemphigoid, sarcoidosis, ichthyosis, Graves ophthalmopathy, inflammatory bowel disease, Addison's disease, Vitiligo, asthma, or allergic asthma.

As used herein, the term "cardiovascular disease" refers to a disease or condition affecting the heart or blood vessels. In embodiments, cardiovascular disease includes diseases caused by or exacerbated by atherosclerosis. Exemplary cardiovascular diseases that may be treated with a compound or method provided herein include Alcoholic cardiomyopathy, Coronary artery disease, Congenital heart disease, Arrhythmogenic right ventricular cardiomyopathy, Restrictive cardiomyopathy, Noncompaction Cardiomyopathy, diabetes mellitus, hypertension, hyperhomocysteinemia, hypercholesterolemia, Atherosclerosis, Ischemic heart disease, Heart failure, Cor pulmonale, Hypertensive heart disease, Left ventricular hypertrophy, Coronary heart disease, (Congestive) heart failure, Hypertensive cardiomyopathy, Cardiac arrhythmias, Inflammatory heart disease, Endocarditis, Inflammatory cardiomegaly, Myocarditis, Valvular heart disease, stroke, or myocardial infarction. In some embodiments, treating a cardiovascular disease includes treating a condition or symptom caused by a cardiovascular disease. A non-limiting example of such a treatment is treating complications due to a myocardial infarction, after the myocardial infarction has occurred.

As used herein, the term "cancer" refers to all types of cancer, neoplasm or malignant tumors found in mammals, including leukemia, carcinomas and sarcomas, adenocarcinomas, lymphomas, solid and lymphoid cancers, etc. Examples of different types of cancer that may be treated or prevented with a compound or method provided herein include, but are not limited to, neuroendocrine cancer, colorectal cancer, liver cancer (i.e., hepatocarcinoma), prostate cancer, renal cancer (i.e., renal cell carcinoma), bladder cancer, lung cancer (e.g., non-small cell lung cancer), breast cancer, thyroid cancer, pleural cancer, pancreatic cancer, ovarian cancer, uterine cancer, cervical cancer, testicular cancer, anal cancer, pancreatic cancer, bile duct cancer, gastrointestinal carcinoid tumors, esophageal cancer, gall bladder cancer, appendix cancer, small intestine cancer, stomach (gastric) cancer, cancer of the central nervous system, skin cancer, choriocarcinoma; head and neck cancer, blood cancer, osteogenic sarcoma, fibrosarcoma, glioblastoma multiforme, neuroblastoma, glioma, melanoma, rhabdomyosarcoma, primary thrombocytosis, primary macroglobulinemia, primary brain tumors, malignant pancreatic insulanoma, malignant carcinoid, urinary bladder cancer, premalignant skin lesions, esophageal cancer, genitourinary tract cancer, malignant hypercalcemia, endometrial cancer, adrenal cortical cancer, neoplasms of the endocrine or exocrine pancreas, B-cell lymphoma, Hodgkin's Disease, non-Hodgkin's lymphoma, Burkitt's lymphoma, Small Cell lymphoma, Large Cell lymphoma, monocytic leukemia, myelogenous leukemia, acute lymphocytic leukemia, acute myelocytic leukemia, and multiple myeloma. In some embodiments, the methods of the present invention are useful for treating colorectal cancer, liver cancer, brain cancer, neuroendocrine cancer, kidney cancer, prostate cancer, bladder cancer, ovarian cancer, breast cancer, lung cancer, leukemia, B-cell lymphoma (e.g., non-Hodgkin's lymphoma, including Burkitt's, Small Cell, and Large Cell lymphomas), multiple myeloma or a subtype thereof.

In some embodiments, the compositions and/or methods of described herein are useful for treating or preventing neuroblastoma. In some embodiments, the compositions and/or methods of described herein are useful for treating or preventing neuroendocrine cancers. In some embodiments, the compositions and/or methods of described herein are useful for treating or preventing cancers that express OCT1. In some embodiments, the compositions and/or methods of described herein are useful for treating or preventing cancers that express OCT2. In some embodiments, the compositions and/or methods of described herein are useful for treating or preventing cancers that express OCT3. In some embodiments, the compositions and/or methods of described herein are useful for treating or preventing cancers that express NET. In some embodiments, the compositions and/or methods of described herein are useful for treating or preventing glioma. In some embodiments, the compositions and/or methods of described herein are useful for treating or preventing glioblastoma multiforme. In some embodiments, the compositions and/or methods of described herein are useful for treating or preventing metastatic cancer or metastases. In some embodiments, the compositions and/or methods of described herein are useful for treating or preventing neuroendocrine metastases.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

The term "sarcoma" generally refers to a tumor which is made up of a substance like the embryonic connective tissue and is generally composed of closely packed cells embedded in a fibrillar or homogeneous substance. Sarcomas that may be treated with a compound or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound or method provided herein include, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, or carcinoma villosum.

As used herein, the term "disease-related cells" means cells that are associated with a disease or condition, which include but are not limited to cells that initiate a disease, cells that propogate a disease, cells that cause a disease, cells that cause one or more symptoms of a disease, cells that are a hallmark of a disease; cells that contain a particular protein or mRNA molecule that causes a symptom of the disease. In some embodiments, the disease is a cancer and the disease-related cell is a cancer cell. In some embodiments, the disease is a metastatic cancer and the disease-related cell is a metastatic cancer cell. In some embodiments, the disease is liver cancer and the disease-related cell is a liver cancer cell. In some embodiments, the disease is kidney cancer and the disease-related cell is a kidney cancer cell. In some embodiments, the disease is colorectal cancer and the disease-related cell is a colorectal cancer cell. In some embodiments, the disease is neuroendocrine cancer and the disease-related cell is a neuroendocrine cancer cell.

"Organic cation transporter" or "OCT" refers to nucleic acids (e.g., gene, pre-mRNA, mRNA), polypeptides, polymorphic variants, alleles, mutants, and interspecies homologs that: (1) have an amino acid sequence that has greater than about 60% amino acid sequence identity, e.g., about 65%, 70%, 75%, 80%, 85%, 90%, 95%, preferably about 91%, 92%, 93%, 94%, 95%, 96%, 97%, 98%, 99%, or greater amino acid sequence identity, preferably over a region of at least about 25, 50, 100, 200, 500, 1000, or more amino acids, to a polypeptide encoded by a referenced nucleic acid or an amino acid sequence described herein, including OCT1, OCT2, and OCT3; (2) specifically bind to antibodies (e.g., polyclonal antibodies) raised against an immunogen comprising a referenced amino acid sequence, immunogenic fragments thereof, and conservatively modified variants thereof, including OCT1, OCT2, and OCT3; (3) specifically hybridize under stringent hybridization conditions to a nucleic acid encoding a referenced amino acid sequence, and conservatively modified variants thereof, including a nucleic acid encoding OCT1, OCT2, or OCT3; and/or (4) have a nucleic acid sequence that has greater than about 95%, preferably greater than about 96%, 97%, 98%, 99%, or higher nucleotide sequence identity, preferably over a region of at least about 25, 50, 100, 200, 500, 1000, or more nucleotides, to a reference nucleic acid sequence, including a reference nucleic acid encoding OCT1, OCT2, or OCT3. A polynucleotide or polypeptide sequence is typically from a mammal including, but not limited to, primate (e.g., human), rodent (e.g., rat, mouse, hamster), cow, pig, horse, sheep, or any mammal. The nucleic acids and proteins of the present invention include both naturally-occurring and recombinant molecules. An exemplary human nucleic acid encoding OCT1 is provided by Accession No. NM_003057; exemplary protein sequences are provided by Accession Nos. NP_003048 and NP_694857. An exemplary human nucleic acid encoding OCT2 is provided by Accession No. NM_003058; exemplary protein sequences are provided by Accession Nos. NP_003049 and NP_694861. An exemplary human nucleic acid encoding OCT3 is provided by Accession No. NM_021977; exemplary protein sequences are provided by Accession Nos. NP_068812 and O75751. Truncated, alternatively spliced, precursor, and mature forms of OCTs are also included in the foregoing definition.

The term "norepinephrine transporter" or "NET" refers to nucleic acids (e.g., gene, pre-mRNA, mRNA), polypeptides, polymorphic variants, alleles, mutants, and interspecies homologs that: (1) have an amino acid sequence that has greater than about 60% amino acid sequence identity, e.g., about 65%, 70%, 75%, 80%, 85%, 90%, 95%, preferably about 91%, 92%, 93%, 94%, 95%, 96%, 97%, 98%, 99%, or greater amino acid sequence identity, preferably over a region of at least about 25, 50, 100, 200, 500, 1000, or more amino acids, to a polypeptide encoded by a referenced nucleic acid or an amino acid sequence described herein, including NET; (2) specifically bind to antibodies (e.g., polyclonal antibodies) raised against an immunogen comprising a referenced amino acid sequence, immunogenic fragments thereof, and conservatively modified variants thereof, including NET; (3) specifically hybridize under stringent hybridization conditions to a nucleic acid encoding a referenced amino acid sequence, and conservatively modified variants thereof, including a nucleic acid encoding NET; and/or (4) have a nucleic acid sequence that has greater than about 95%, preferably greater than about 96%, 97%, 98%, 99%, or higher nucleotide sequence identity, preferably over a region of at least about 25, 50, 100, 200, 500, 1000, or more nucleotides, to a reference nucleic acid sequence, including a reference nucleic acid encoding NET. A polynucleotide or polypeptide sequence is typically from a mammal including, but not limited to, primate (e.g., human), rodent (e.g., rat, mouse, hamster), cow, pig, horse, sheep, or any mammal. The nucleic acids and proteins of the present invention include both naturally-occurring and recombinant molecules. An exemplary human nucleic acid encoding NET is provided by Accession No. NM_001043; exemplary protein sequences are provided by Accession Nos. NP_001034. Truncated, alternatively spliced, precursor, and mature forms of NET are also included in the foregoing definition. NET is a member of the solute carrier family 6, and is solute carrier family 6, member 2 (SLC6A2). Human NET is located on chromosome 16 locus 16q12.2. NET is a monoamine transporter that transports norepinephrine and dopamine from the synapse to the cytosol.

The term "expression" refers to a gene that is transcribed or translated at a detectable level. As used herein, expression also encompasses "overexpression," which refers to a gene that is transcribed or translated at a detectably greater level, usually in a cancer cell, in comparison to a normal cell. Expression therefore refers to both expression of OCT (or NET) protein and RNA, as well as local overexpression due to altered protein trafficking patterns and/or augmented functional activity. Expression can be detected using conventional techniques for detecting protein (e.g., ELISA, Western blotting, flow cytometry, immunofluorescence, immunohistochemistry, etc.) or mRNA (e.g., RT-PCR, PCR, hybridization, etc.). One skilled in the art will know of other techniques suitable for detecting expression of OCT (or NET) protein or mRNA. Cancerous cells, e.g., cancerous colon or liver cells or kidney cells or neuroendocrine cells in the case of NET, can express (e.g., overexpress) one or more OCTs (e.g., OCT1, OCT2, and/or OCT3) or NET at a level of at least about 5%, 10%, 15%, 20%, 25%, 30%, 35%, 40%, 45%, 50%, 55%, 60%, 65%, 70%, 75%, 80%, 85%, 90%, or 95% in comparison to normal, non-cancerous cells such as colon or liver cells or neuroendocrine cells in the case of NET. Cancerous cells can also have at least about a 1-fold, 2-fold, 3-fold, 4-fold, 5-fold, 6-fold, or 7-fold higher level of OCT (or NET) transcription or translation in comparison to normal, non-cancerous cells. In certain instances, the cancer cell sample is autologous.

"Therapy resistant" cancers, tumor cells, and tumors refer to cancers that have become resistant to both apoptosis-mediated (e.g., through death receptor cell signaling, for example, Fas ligand receptor, TRAIL receptors, TNF-R1, chemotherapeutic drugs, radiation, etc.) and non-apoptosis mediated (e.g., toxic drugs, chemicals, etc.) cancer therapies including, but not limited to, chemotherapy, hormonal therapy, radiotherapy, immunotherapy, and combinations thereof.

As used herein, the term "marker" refers to any biochemical marker, serological marker, genetic marker, or other clinical or echographic characteristic that can be used to diagnose or provide a prognosis for a cancer that expresses at least one OCT or NET according to the methods of the present invention. Preferably, the marker is an OCT or NET protein or nucleic acid marker such as a NET marker or an OCT1, OCT2, and/or OCT3 marker.

The term "sample" includes sections of tissues such as biopsy and autopsy samples, and frozen sections taken for histological purposes. Such samples include blood and blood fractions or products (e.g., serum, plasma, platelets, red blood cells, and the like), sputum, tissue, cultured cells (e.g., primary cultures, explants, and transformed cells), stool, urine, other biological fluids (e.g., prostatic fluid, gastric fluid, intestinal fluid, renal fluid, lung fluid, cerebrospinal fluid, and the like), etc. A sample is typically obtained from a "subject" such as a eukaryotic organism, most preferably a mammal such as a primate, e.g., chimpanzee or human; cow; dog; cat; a rodent, e.g., guinea pig, rat, mouse; rabbit; or a bird; reptile; or fish. In some embodiments, the sample is obtained from a human.

A "biopsy" refers to the process of removing a tissue sample for diagnostic or prognostic evaluation, and to the tissue specimen itself. Any biopsy technique known in the art can be applied to the diagnostic and prognostic methods of the present invention. The biopsy technique applied will depend on the tissue type to be evaluated (e.g., colon, prostate, kidney, bladder, lymph node, liver, bone marrow, blood cell, etc.), the size and type of the tumor (e.g., solid or suspended, blood or ascites), among other factors. Representative biopsy techniques include, but are not limited to, excisional biopsy, incisional biopsy, needle biopsy, surgical biopsy, and bone marrow biopsy. An "excisional biopsy" refers to the removal of an entire tumor mass with a small margin of normal tissue surrounding it. An "incisional biopsy" refers to the removal of a wedge of tissue that includes a cross-sectional diameter of the tumor. A diagnosis or prognosis made by endoscopy or fluoroscopy can require a "core-needle biopsy" of the tumor mass, or a "fine-needle aspiration biopsy" which generally obtains a suspension of cells from within the tumor mass. Biopsy techniques are discussed, for example, in *Harrison's Principles of Internal Medicine,* Kasper, et al., eds., 16th ed., 2005, Chapter 70, and throughout Part V.

The terms "identical" or percent "identity," in the context of two or more nucleic acids or polypeptide sequences, refer to two or more sequences or subsequences that are the same or have a specified percentage of amino acid residues or nucleotides that are the same (e.g., about 60% identity, preferably about 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithm with default parameters described below, or by manual alignment and visual inspection (see, e.g., NCBI web site http://www.ncbi.nlm.nih.gov/BLAST/ or the like). Such sequences are then said to be "substantially identical." This definition also refers to, or may be applied to, the complement of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or over a region that is about 50-100 amino acids or nucleotides in length.

A "comparison window," as used herein, includes reference to a segment of any one of the number of contiguous positions selected from the group consisting of from about 20 to about 600, usually from about 50 to about 200, more usually from about 100 to about 150, in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman, *Adv. Appl. Math.*, 2:482 (1981), by the homology alignment algorithm of Needleman and Wunsch, *J. Mol. Biol.*, 48:443 (1970), by the search for similarity method of Pearson and Lipman, *Proc. Nat'l. Acad. Sci. USA*, 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1987-2005, Wiley Interscience)).

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A preferred example of algorithms suitable for determining percent sequence identity and sequence similarity are the BLAST and BLAST 2.0 algorithms, which are described in Altschul et al., *Nuc. Acids Res.*, 25:3389-3402 (1977) and Altschul et al., *J. Mol. Biol.*, 215:403-410 (1990), respectively. BLAST and BLAST 2.0 are used, with the parameters described herein, to determine percent sequence identity for the nucleic acids and proteins of the present invention. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, M=5, N=−4, and a comparison of both strands. For amino acid sequences, the BLASTP program uses as defaults a word length of 3, and expectation (E) of 10, and the BLOSUM62 scoring matrix (see, Henikoff et al., *Proc. Natl. Acad. Sci. USA*, 89:10915 (1989)) alignments (B) of 50, expectation (E) of 10, M=5, N=−4, and a comparison of both strands.

"Nucleic acid" refers to deoxyribonucleotides or ribonucleotides and polymers thereof in either single- or double-stranded form and complements thereof. The term encompasses nucleic acids containing known nucleotide analogs or modified backbone residues or linkages, which are synthetic, naturally-occurring, or non-naturally occurring, which have similar binding properties as the reference nucleic acid, or which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, and peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.*, 19:5081 (1991); Ohtsuka et al., *J. Biol. Chem.*, 260:2605-2608 (1985); Rossolini et al., *Mol. Cell. Probes*, 8:91-98 (1994)). In some embodiments, a nucleic acid is a gene, cDNA, mRNA, oligonucleotide, or polynucleotide.

A particular nucleic acid sequence also implicitly encompasses "splice variants" and nucleic acid sequences encoding truncated forms of OCT or NET. Similarly, a particular protein encoded by a nucleic acid implicitly encompasses any protein encoded by a splice variant or truncated form of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition. Nucleic acids can be truncated at the 5'-end or at the 3'-end. Polypeptides can be truncated at the N-terminal end or the C-terminal end. Truncated versions of nucleic acid or polypeptide sequences can be naturally-occurring or recombinantly created.

"Polymorphism" refers to the occurrence of two or more genetically determined alternative sequences or alleles in a population (e.g., NET, OCT1, OCT2, or OCT3 alleles). A "polymorphic site" refers to the locus at which divergence occurs. Preferred polymorphic sites have at least two alleles, each occurring at frequency of greater than 1%, and more preferably greater than 10% or 20% of a selected population. A polymorphic locus can be as small as one base pair (single nucleotide polymorphism, or SNP). Polymorphic markers include restriction fragment length polymorphisms, variable number of tandem repeats (VNTR's), hypervariable regions, minisatellites, dinucleotide repeats, trinucleotide repeats, tetranucleotide repeats, simple sequence repeats, and insertion elements such as Alu. The first identified allele is arbitrarily designated as the reference allele and other alleles are designated as alternative or "variant alleles." The allele occurring most frequently in a selected population is sometimes referred to as the "wild-type" allele. Diploid organisms may be homozygous or heterozygous for the variant alleles. The variant allele may or may not produce an observable physical or biochemical characteristic ("phenotype") in an individual carrying the variant allele. For example, a variant allele may alter the enzymatic activity of a protein encoded by a gene of interest.

The term "genotype" as used herein broadly refers to the genetic composition of an organism, including, for example, whether a diploid organism is heterozygous or homozygous for one or more variant alleles of interest.

The term "gene amplification" refers to a cellular process characterized by the production of multiple copies of any particular piece of DNA. For example, a tumor cell amplifies, or copies, chromosomal segments naturally as a result of cell signals and sometimes environmental events. The process of gene amplification leads to the production of many copies of the genes that are located on that region of the chromosome. In certain instances, so many copies of the amplified region are produced that they can form their own small pseudo-chromosomes called double-minute chromosomes. The genes on each of the copies can be transcribed and translated, leading to an overproduction of the mRNA and protein corresponding to the amplified genes.

The terms "polypeptide," "peptide," and "protein" are used interchangeably herein to refer to a polymer of amino acid residues. The terms apply to amino acid polymers in which one or more amino acid residue is an artificial chemical mimetic of a corresponding naturally-occurring amino acid, as well as to naturally-occurring amino acid polymers and non-naturally occurring amino acid polymers.

The term "amino acid" refers to naturally occurring and synthetic amino acids, as well as amino acid analogs and amino acid mimetics that function in a manner similar to the naturally-occurring amino acids. Naturally-occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, and methionine methyl sulfonium. Such analogs have modified R groups (e.g., norleucine) or modified peptide backbones, but retain the same basic chemical structure as a naturally-occurring amino acid. Amino acid mimetics refers to chemical compounds that have a structure that is different from the general chemical structure of an amino acid, but that functions in a manner similar to a naturally-occurring amino acid.

Amino acids may be referred to herein by either their commonly known three-letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids that encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill in the art will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill in the art will recognize that individual substitutions, deletions, or additions to a nucleic acid, peptide, polypeptide, or protein sequence which alters, adds, or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the present invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

The term "recombinant," when used with reference, e.g., to a cell, nucleic acid, protein, or vector, indicates that the cell, nucleic acid, protein, or vector has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, overexpressed, underexpressed, or not expressed at all.

The term "heterologous," when used with reference to portions of a nucleic acid, indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

The phrase "stringent hybridization conditions" refers to conditions under which a probe will hybridize to its target subsequence, typically in a complex mixture of nucleic acids, but to no other sequences. Stringent conditions are sequence-dependent and may be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$)

for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably at least ten times background hybridization. Exemplary stringent hybridization conditions can be as follows: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides that they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill in the art will readily recognize that alternative hybridization and wash conditions can be utilized to provide conditions of similar stringency. Additional guidelines for determining hybridization parameters are provided in numerous reference, e.g., and *Current Protocols in Molecular Biology*, ed. Ausubel, et al., supra.

For PCR, a temperature of about 36° C. is typical for low stringency amplification, although annealing temperatures may vary between about 32° C. and about 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of about 90-95° C. for about 30 sec-2 min., an annealing phase lasting about 30 sec.-2 min., and an extension phase of about 72° C. for about 1-2 min. Protocols and guidelines for low and high stringency amplification reactions are provided, e.g., in Innis et al. (1990) *PCR Protocols, A Guide to Methods and Applications*, Academic Press, Inc. N.Y.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD, and IgE, respectively. Typically, the antigen-binding region of an antibody will be most critical in specificity and affinity of binding.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to about 110 or more amino acids primarily responsible for antigen recognition. The terms variable light chain ($V_L$) and variable heavy chain ($V_H$) refer to these light and heavy chains, respectively.

Antibodies exist, e.g., as intact immunoglobulins or as a number of well-characterized fragments produced by digestion with various peptidases. Thus, for example, pepsin digests an antibody below the disulfide linkages in the hinge region to produce $F(ab)'_2$, a dimer of Fab which itself is a light chain joined to $V_H$—$C_H1$ by a disulfide bond. The $F(ab)'_2$ may be reduced under mild conditions to break the disulfide linkage in the hinge region, thereby converting the $F(ab)'_2$ dimer into an Fab' monomer. The Fab' monomer is essentially Fab with part of the hinge region (see, *Fundamental Immunology*, Paul ed., 3d ed. 1993). While various antibody fragments are defined in terms of the digestion of an intact antibody, one of skill in the art will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990))

For preparation of antibodies, e.g., recombinant, monoclonal, or polyclonal antibodies, any technique known in the art can be used (see, e.g., Kohler and Milstein, *Nature*, 256: 495-497 (1975); Kozbor et al., *Immunology Today*, 4: 72 (1983); Cole et al., pp. 77-96 in *Monoclonal Antibodies and Cancer Therapy*, Alan R. Liss, Inc. (1985); Coligan, *Current Protocols in Immunology* (1991); Harlow and Lane, *Antibodies, A Laboratory Manual* (1988); and Goding, *Monoclonal Antibodies: Principles and Practice* (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, *Immunology* ($3^{rd}$ ed. 1997)). Techniques for the production of single chain antibodies or recombinant antibodies (see, e.g., U.S. Pat. Nos. 4,946,778 and 4,816,567) can be adapted to produce antibodies to the polypeptides of the present invention. Also, transgenic mice or other organisms such as other mammals may be used to express humanized or human antibodies (see, e.g., U.S. Pat. Nos. 5,545,807; 5,545,806; 5,569,825; 5,625,126; 5,633,425; and 5,661,016, Marks et al., *Biotechnology*, 10:779-783 (1992); Lonberg et al., *Nature*, 368:856-859 (1994); Morrison, *Nature*, 368:812-13 (1994); Fishwild et al., *Nature Biotechnology*, 14:845-51 (1996); Neuberger, *Nature Biotechnology*, 14:826 (1996); and Lonberg et al., *Intern. Rev. Immunol.*, 13:65-93 (1995)). Alternatively, phage display technology can be used to identify antibodies and heteromeric Fab fragments that specifically bind to selected antigens (see, e.g., McCafferty et al., *Nature*, 348:552-554 (1990); Marks et al., supra). Antibodies can also be made bispecific, i.e., able to recognize two different antigens (see, e.g., PCT Patent Publication No. WO 93/08829; Traunecker et al., *EMBO J.*, 10:3655-3659 (1991); and Suresh et al., *Methods in Enzymology*, 121:210 (1986)). Antibodies can also be heteroconjugates, e.g., two covalently joined antibodies, or immunotoxins (see, e.g., U.S. Pat. No. 4,676,980, PCT Patent Publication Nos. WO 91/00360 and WO 92/200373; and EP Patent No. 03089).

Methods for humanizing or primatizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers (see, e.g., Jones et al., *Nature*, 321:522-525 (1986); Riechmann et al., *Nature*, 332: 323-327 (1988); Verhoeyen et al., *Science*, 239:1534-1536 (1988) and Presta, *Curr. Op. Struct. Biol.*, 2:593-596 (1992)), by substituting rodent CDRs or CDR sequences for the corresponding sequences of a human antibody. Accordingly, such humanized antibodies are chimeric antibodies (see, e.g., U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

A "chimeric antibody" is an antibody molecule in which (a) the constant region, or a portion thereof, is altered, replaced, or exchanged so that the antigen binding site (variable region) is linked to a constant region of a different or altered class, effector function, and/or species, or an entirely different molecule which confers new properties to the chimeric antibody, e.g., an enzyme, toxin, hormone, growth factor, drug, etc.; or (b) the variable region, or a portion thereof, is altered, replaced, or exchanged with a variable region having a different or altered antigen specificity.

In one embodiment, the antibody is conjugated to an "effector" moiety. The effector moiety can be any number of molecules, including labeling moieties such as radioactive labels or fluorescent labels, or can be a therapeutic moiety. In one embodiment, the antibody modulates the activity of the protein.

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least about two, three, four, or more times the background, and more typically more than at least about 10 to about 100 times the background. Specific binding to an antibody under such conditions requires an antibody that is selected for its specificity for a particular protein. For example, polyclonal antibodies can be selected to obtain only those polyclonal antibodies that are specifically immunoreactive with the selected antigen and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow and Lane, *Antibodies, A Laboratory Manual* (1988) for a description of immunoassay formats and conditions that can be used to determine specific immunoreactivity).

As used herein, the term "administering" means oral administration, administration as a suppository, topical contact, intravenous, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies, for example cancer therapies such as chemotherapy, hormonal therapy, radiotherapy, or immunotherapy. The compounds of the invention can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation). The compositions of the present invention can be delivered by transdermally, by a topical route, formulated as applicator sticks, solutions, suspensions, emulsions, gels, creams, ointments, pastes, jellies, paints, powders, and aerosols.

The term "administer (or administering) a transporter substrate" means administering a transporter substrate (e.g. an organic cation transporter substrate or norephinephrine transporter substrate) to a subject and, without being limited by mechanism, allowing sufficient time for the transporter substrate to be translocated into a cell by a transporter and for the transporter substrate to then prevent replication of the cellular DNA or cause cell death of the cell or react with DNA or modify DNA or covalently modify DNA.

II. Compositions

In a first aspect a compound having the formula:

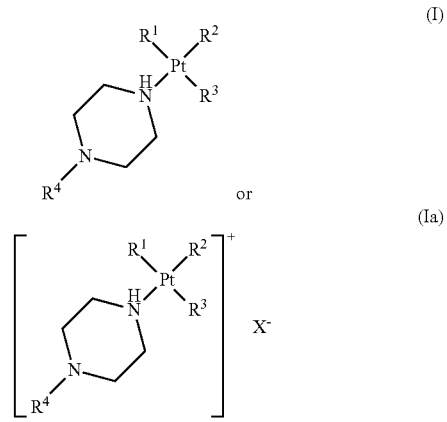

is provided.

$X^-$ is a counterion. $R^1$, $R^2$, and $R^3$ are independently halogen, —$SR^9$, —$OSO_2R^8$, —$OSO_3H$, —$NH_2NH_2$, —$ONR^6R^7$, —$NH_2C=(O)NHNH_2$, —$NH_2C=(O)NR^6R^7$, —$NR^5R^6R^7$, —$OC(O)R^8$, —$OC(O)NR^6R^7$, —$OR^9$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, wherein $R^1$ and $R^2$, $R^2$ and $R^3$ or $R^1$ and $R^3$ may optionally be joined to form a substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^4$ is independently hydrogen, halogen, —CY$_3$, —CN, —SO$_2$Cl, —SO$_q$R$^{14}$, —SO$_u$NR$^{11}$R$^{12}$, —NHNH$_2$, —ONR$^{11}$R$^{12}$, —NHC═(O)NHNH$_2$, —NHC═(O)NR$^{11}$R$^{12}$, —N(O)$_m$, —NR$^{11}$R$^{12}$, —C(O)R$^{13}$, —C(O)OR$^{13}$, —C(O)NR$^{11}$R$^{12}$, —OR$^{14}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^5$, R$^6$, R$^7$, R$^8$, and R$^9$ are independently hydrogen, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC═(O)NHNH$_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^{11}$, R$^{12}$, R$^{13}$, and R$^{14}$ are independently hydrogen, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC═(O)NHNH$_2$, substituted or unsubstituted cycloalkyl, substituted or unsubstituted heterocycloalkyl, substituted or unsubstituted aryl, or substituted or unsubstituted heteroaryl. The symbol u is independently an integer from 1 to 2. The symbol m is independently an integer from 1 to 2. The symbol q is independently an integer from 0 to 4. The symbol Y is independently —Cl, —Br, —I, or —F.

In some embodiments, X$^-$ is acetate, bromide, camsylate, chloride, formate, fumarate, maleate, mesylate, nitrate, oxalate, phosphate, sulfate, tartrate, thiocyanate, or tosylate. In some embodiments, X$^-$ is NO$_3$$^-$. In another embodiment, X$^-$ is a halogen ion chosen from F$^-$, Cl$^-$, Br$^-$, or I$^-$. In some embodiments, the counterion is Cl$^-$.

For the compound of formula (I) or (Ia) including embodiments thereof, a person of skill in the art will immediately recognize that the nitrogen bound to the platinum may be positively charged depending on the identity of the compound. The nitrogen bound to the platinum refers to the nitrogen indicated by an asterisk in the below structure:

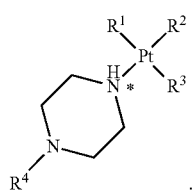

In some embodiments, the nitrogen is attached to the platinum as a coordinate ligand. In other embodiments, the nitrogen is attached to the platinum as a counter ion. Where the nitrogen is attached to the platinum as a counter ion, a person of skill in the art will immediately understand that the nitrogen is formally positively charged.

In some embodiments, R$^1$, R$^2$, and R$^3$ are independently halogen, —SR$^9$, —OSO$_2$R$^8$, —OSO$_3$H, —NH$_2$NH$_2$, —ONR$^6$R$^7$, —NH$_2$C═(O)NHNH$_2$, —NH$_2$C═(O)NR$^6$R$^7$, —NR$^5$R$^6$R$^7$, —OC(O)R$^8$, —OC(O)NR$^6$R$^7$, —OR$^9$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In some embodiments, the R$^1$, R$^2$, and R$^3$ atoms interacting directly with (e.g. bonding with) the Pt atom are not carbon. In some embodiments, R$^1$, R$^2$, and R$^3$ are attached to the Pt atom through an atom that is not a carbon atom. In some embodiments, R$^1$, R$^2$, and R$^3$ are attached to the Pt atom through an atom that is a heteroatom. In some embodiments, R$^1$, R$^2$, and R$^3$ are independently halogen, —SR$^9$, —OSO$_2$R$^8$, —OSO$_3$H, —NH$_2$NH$_2$, —ONR$^6$R$^7$, —NH$_2$C═(O)NHNH$_2$, —NH$_2$C═(O)NR$^6$R$^7$, —NR$^5$R$^6$R$^7$, —OC(O)R$^8$, —OC(O)NR$^6$R$^7$, —OR$^9$, substituted or unsubstituted heteroalkyl, substituted or unsubstituted heterocycloalkyl, or substituted or unsubstituted heteroaryl. In some embodiments, R$^1$, R$^2$, and R$^3$ are independently halogen, —SR$^9$, —OSO$_2$R$^8$, —OSO$_3$H, —NH$_2$NH$_2$, —ONR$^6$R$^7$, —NH$_2$C═(O)NHNH$_2$, —NH$_2$C═(O)NR$^6$R$^7$, —NR$^5$R$^6$R$^7$, —OC(O)R$^8$, —OC(O)NR$^6$R$^7$, —OR$^9$, substituted or unsubstituted heteroalkyl, substituted or unsubstituted heterocycloalkyl, or substituted or unsubstituted heteroaryl. In some embodiments, R$^1$ and R$^2$, R$^2$ and R$^3$ or R$^1$ and R$^3$ may optionally be joined to form a substituted or unsubstituted heteroalkyl, substituted or unsubstituted heterocycloalkyl, or substituted or unsubstituted heteroaryl. In some embodiments, R$^1$ and R$^2$, R$^2$ and R$^3$ or R$^1$ and R$^3$ may optionally be joined to form a substituted or unsubstituted heterocycloalkyl or substituted or unsubstituted heteroaryl. In some embodiments, R$^1$ and R$^2$, R$^2$ and R$^3$ or R$^1$ and R$^3$ may optionally be joined to form a substituted or unsubstituted heterocycloalkyl. Where the substituent (e.g. R$^1$, R$^2$, or R$^3$) is —OSO$_3$H, a person of skill in the art will immediately understand that the definition of —OSO$_3$H also includes the corresponding base —OSO$_3$$^-$. Thus, in some embodiments, R$^1$, R$^2$, and R$^3$ are independently —OSO$_3$H. In other embodiments, R$^1$, R$^2$, or R$^3$ are independently —OSO$_3$$^-$.

In some embodiments, R$^1$, R$^2$, and R$^3$ are independently halogen, —SR$^9$, —OSO$_2$R$^8$, —OSO$_3$H, —NH$_2$NH$_2$, —ONR$^6$R$^7$, —NH$_2$C═(O)NHNH$_2$, —NH$_2$C═(O)NR$^6$R$^7$, —NR$^5$R$^6$R$^7$, —OC(O)R$^8$, —OC(O)NR$^6$R$^7$, —OR$^9$, substituted or unsubstituted heteroalkyl, substituted or unsubstituted heterocycloalkyl, or substituted or unsubstituted heteroaryl, with the proviso that the R$^1$, R$^2$, and R$^3$ atoms interacting directly with (e.g. coordinated with, bonded with, coordinate covalent bonded with) the Pt atom are not carbon. In some embodiments, R$^1$, R$^2$, and R$^3$ are independently halogen, —SR$^9$, —OSO$_2$R$^8$, —OSO$_3$H, —NH$_2$NH$_2$, —ONR$^6$R$^7$, —NH$_2$C═(O)NHNH$_2$, —NH$_2$C═(O)NR$^6$R$^7$, —NR$^5$R$^6$R$^7$, —OC(O)R$^8$, —OC(O)NR$^6$R$^7$, —OR$^9$, substituted or unsubstituted heteroalkyl, substituted or unsubstituted heterocycloalkyl, or substituted or unsubstituted heteroaryl, with the proviso that the R$^1$, R$^2$, and R$^3$ are attached to the Pt atom through an atom (i.e. donor atom) that is not a carbon atom. In some embodiments of the compounds described herein (e.g. formula I, Ia, II, IIa, III, IIIa, IV, or V, including embodiments), the R$^1$ donor atom, R$^2$ donor atom, and R$^3$ donor atom are not carbon. In some embodiments of the compounds described herein (e.g. formula I, Ia, II, IIa, III, IIIa, IV, or V, including embodiments), the R$^1$ donor atom, R$^2$ donor atom, and R$^3$ donor atom are heteroatoms, which may optionally be different heteroatoms. In some embodiments, the R$^1$ donor atom, R$^2$ donor atom, and R$^3$ donor atom are independently nitrogen, oxygen or a halogen.

In some embodiments, R$^1$, R$^2$, and R$^3$ are independently halogen, —SR$^9$, —OSO$_2$R$^8$, —OSO$_3$H, —NH$_2$NH$_2$, —ONR$^6$R$^7$, —NH$_2$C═(O)NHNH$_2$, —NH$_2$C═(O)NR$^6$R$^7$, —NR$^5$R$^6$R$^7$, —OC(O)R$^8$, —OC(O)NR$^6$R$^7$, —OR$^9$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. Where R$^1$, R$^2$, and R$^3$ are independently halogen, —SR$^9$, —OSO$_2$R$^8$, —OSO$_3$H, —NH$_2$NH$_2$, —ONR$^6$R$^7$, —NH$_2$C═(O)NHNH$_2$, —NH$_2$C═(O)NR$^6$R$^7$, —NR$^5$R$^6$R$^7$, —OC(O)

R$^8$, —OC(O)NR$^6$R$^7$, —OR$^9$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, R$^5$, R$^6$, R$^7$, R$^8$, or R$^9$ can be independently defined for R$^1$, R$^2$ or R$^3$, respectively. R$^5$, R$^6$, R$^7$, R$^8$, or R$^9$ may be independently R$^{5A}$, R$^{5B}$, R$^{5C}$, R$^{6A}$, R$^{6B}$, R$^{6C}$, R$^{7A}$, R$^{7B}$, R$^{7C}$, R$^{8A}$, R$^{8B}$, R$^{8C}$, R$^{9A}$, R$^{9B}$ or R$^{9C}$ where serving as a substituent of R$^1$, R$^2$ or R$^3$, respectively. A person of skill in the art will immediately recognize that R$^5$ may be independently R$^{5A}$, R$^{5B}$ or R$^{5C}$ where serving as a substituent of R$^1$, R$^2$, or R$^3$ respectively. In some embodiments, R$^6$ may be independently R$^{6A}$, R$^{6B}$ or R$^{6C}$ where serving as a substituent of R$^1$, R$^2$, or R$^3$ respectively. In some embodiments, R$^7$ may be independently R$^{7A}$, R$^{7B}$ or R$^{7C}$ where serving as a substituent of R$^1$, R$^2$, or R$^3$ respectively. In some embodiments, R$^8$ may be independently R$^{8A}$, R$^{8B}$ or R$^{8C}$ where serving as a substituent of R$^1$, R$^2$, or R$^3$ respectively. In some embodiments, R$^9$ may be independently R$^{9A}$, R$^{9B}$ or R$^{9C}$ where serving as a substituent of R$^1$, R$^2$, or R$^3$ respectively. In some embodiments, R$^1$ is independently halogen, —SR$^{9A}$, —OSO$_2$R$^{8A}$, —OSO$_3$H, —NH$_2$NH$_2$, —ONR$^{6A}$R$^{7A}$, —NH$_2$C=(O)NHNH$_2$, —NH$_2$C=(O)NR$^{6A}$R$^{7A}$, —NR$^{5A}$R$^{6A}$R$^{7A}$, —OC(O)R$^{8A}$, —OC(O)NR$^{6A}$R$^{7A}$, —OR$^{9A}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In some embodiments, R$^2$ is independently halogen, —SR$^{9B}$, —OSO$_2$R$^{8B}$, —OSO$_3$H, —NH$_2$NH$_2$, —ONR$^{6B}$R$^{7B}$, —NH$_2$C=(O)NHNH$_2$, —NH$_2$C=(O)NR$^{6B}$R$^{7B}$, —NR$^{5B}$R$^{6B}$R$^{7B}$, —OC(O)R$^{8B}$, —OC(O)NR$^{6B}$R$^{7B}$, —OR$^{9B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In some embodiments, R$^3$ is independently halogen, —SR$^{9C}$, —OSO$_2$R$^{8C}$, —OSO$_3$H, —NH$_2$NH$_2$, —ONR$^{6C}$R$^{7C}$, —NH$_2$C=(O)NHNH$_2$, —NH$_2$C=(O)NR$^{6C}$R$^{7C}$, —NR$^{5C}$R$^{6C}$R$^{7C}$, —OC(O)R$^{8C}$, —OC(O)NR$^{6C}$R$^{7C}$, —OR$^{9C}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In some embodiments, R$^4$ is substituted or unsubstituted cycloalkyl, substituted or unsubstituted heterocycloalkyl, substituted or unsubstituted aryl, or substituted or unsubstituted heteroaryl. In some embodiments, R$^4$ is substituted or unsubstituted aryl or substituted or unsubstituted heteroaryl. In some embodiments, R$^4$ is substituted or unsubstituted aryl. In some embodiments, R$^4$ is substituted or unsubstituted phenyl. In some embodiments, R$^4$ is unsubstituted phenyl. In some embodiments, R$^4$ is substituted or unsubstituted pyridyl. In some embodiments, R$^4$ is 2-pyridyl. In some embodiments, R$^4$ is 3-pyridyl. In some embodiments, R$^4$ is 4-pyridyl. In some embodiments R$^4$ is substituted with 1 substituent. In other embodiments, R$^4$ is substituted with 2 substituents. In some embodiments, R$^4$ is substituted with 3 substituents. In some embodiments, where R$^4$ is substituted with more than 1 substituent, the substituents are each optionally different. In some embodiments, where R$^4$ is substituted with more than 1 substituent, the substituents are all the same (including the piperazinyl shown in formula I and Ia). In some embodiments, R$^5$, R$^6$, R$^7$, R$^8$, and R$^9$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In some embodiments, R$^5$ and R$^6$, R$^6$ and R$^7$, or R$^5$ and R$^7$, may optionally be joined to form, in combination with their commonly bonded nitrogen, as shown in formula I or Ia, a substituted or unsubstituted heterocycloalkyl or substituted or unsubstituted heteroaryl. In some embodiments, u is 1. In some embodiments, u is 2. In some embodiments, m is 1. In some embodiments, m is 2. In some embodiments, q is 0. In some embodiments, q is 1. In some embodiments, q is 2. In some embodiments, q is 3. In some embodiments, q is 4. In some embodiments Y is —F. In some embodiments, Y is —Cl. In some embodiments, Y is —I. In some embodiments, Y is —Br. In some embodiments, Y is a mixture of halogens and —CY$_3$ is for example —CCl$_2$F.

In some embodiments, R$^{11}$, R$^{12}$, R$^{13}$, and R$^{14}$ are hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In some embodiments, the compound of formula I or Ia is the compound of formula II or IIa, respectively:

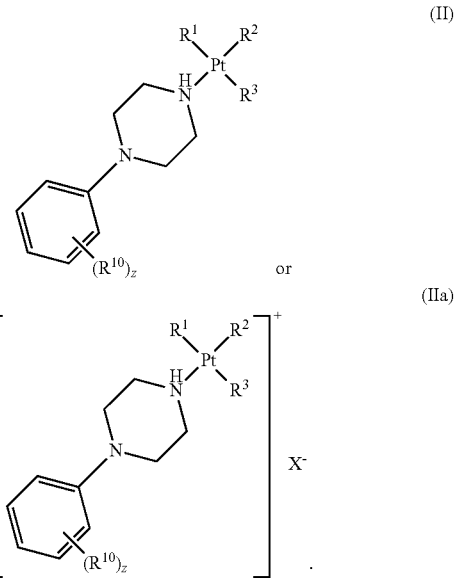

X$^-$, R$^1$, R$^2$, R$^3$, R$^5$, R$^6$, R$^7$, R$^8$, R$^9$, R$^{11}$, R$^{12}$, R$^{13}$, R$^{14}$, Y, m, q, and u are as defined above. R$^{10}$ is independently hydrogen, halogen, —CY$_3$, —CN, —SO$_2$Cl, —SO$_q$R$^{14}$, —SO$_u$NR$^{11}$R$^{12}$, —NHNH$_2$, —ONR$^{11}$R$^{12}$, —NHC=(O) NHNH$_2$, —NHC=(O)NR$^{11}$R$^{12}$, —N(O)$_m$, —NR$^{11}$R$^{12}$, —C(O)R$^{13}$, —C(O)—OR$^{13}$, —C(O)NR$^{11}$R$^{12}$, —OR$^{14}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In some embodiments, R$^{10}$ is a halogen. In some embodiments, R$^{10}$ is —F. In some embodiments, multiple R$^{10}$ substituents may be present on the same compound and each R$^{10}$ may be different (e.g. —SR$^{14}$ and —OR$^{14}$) and each R group within each R$^{10}$ may be different even if the R groups have the same identifying number (e.g. —SR$^{14}$ and —OR$^{14}$, wherein the R$^{14}$ of —SR$^{14}$ is for example substituted alkyl and the R$^{14}$ of —OR$^{14}$ is for example, unsubstituted heteroaryl). In some embodiments, two R$^{10}$ substituents may optionally be joined to form a substituted or unsubstituted cycloalkyl, substituted or unsubstituted heterocycloalkyl, substituted or unsubstituted aryl, or substituted or unsubstituted heteroaryl. In some embodiments, the two $R^{10}$ substituents may be attached to the same ring atom of the phenyl shown in formula II or IIa. In some embodiments, the two $R^{10}$ substituents may be attached to adjacent ring atoms of the phenyl shown in formula II or IIa. In some embodiments, the two $R^{10}$ substituents may be attached to different, non-adjacent ring atoms of the phenyl shown in formula II or IIa. The symbol z is an integer from 0 to 5. In some embodiments z is 0. In some embodiments z is 1. In some embodiments z is 2. In some embodiments z is 3. In some embodiments z is 4. In some embodiments z is 5.

In some embodiments of a formula above (i.e. I, Ia, II, or IIa), $R^1$ is —$SR^9$, —$OSO_2R^8$, —$OSO_3H$, —$NH_2NH_2$, —$ONR^6R^7$, —$NH_2C$=(O)$NHNH_2$, —$NH_2C$=(O)$NR^6R^7$, —$NR^5R^6R^7$, —$OC(O)R^8$, —$OC(O)NR^6R^7$, —$OR^9$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In some embodiments, $R^1$ is independently —$SR^9$, —$OSO_2R^8$, —$OSO_3H$, —$NH_2NH_2$, —$ONR^6R^7$, —$NH_2C$=(O)$NHNH_2$, —$NH_2C$=(O)$NR^6R^7$, —$NR^5R^6R^7$, —$OC(O)R^8$, —$OC(O)NR^6R^7$, —$OR^9$, substituted or unsubstituted heteroalkyl, substituted or unsubstituted heterocycloalkyl, or substituted or unsubstituted heteroaryl. In some embodiments, $R^2$ and $R^3$ are independently halogen. $R^5$, $R^6$, $R^7$, $R^8$, and $R^9$ are as described herein. In some embodiments, $R^1$ is —$NH_3$. In some embodiments, $R^2$ and $R^3$ are independently —Cl.

In some embodiments of a formula above (i.e. I, Ia, II, or IIa), $R^2$ is —$SR^9$, —$OSO_2R^8$, —$OSO_3H$, —$NH_2NH_2$, —$ONR^6R^7$, —$NH_2C$=(O)$NHNH_2$, —$NH_2C$=(O)$NR^6R^7$, —$NR^5R^6R^7$, —$OC(O)R^8$, —$OC(O)NR^6R^7$, —$OR^9$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In some embodiments, $R^2$ is independently —$SR^9$, —$OSO_2R^8$, —$OSO_3H$, —$NH_2NH_2$, —$ONR^6R^7$, —$NH_2C$=(O)$NHNH_2$, —$NH_2C$=(O)$NR^6R^7$, —$NR^5R^6R^7$, —$OC(O)R^8$, —$OC(O)NR^6R^7$, —$OR^9$, substituted or unsubstituted heteroalkyl, substituted or unsubstituted heterocycloalkyl, or substituted or unsubstituted heteroaryl. In some embodiments, $R^1$ and $R^3$ are independently halogen. $R^5$, $R^6$, $R^7$, $R^8$, and $R^9$ are as described herein. In some embodiments, $R^2$ is —$NH_3$. In some embodiments, $R^1$ and $R^3$ are independently —Cl.

In some embodiments of a formula above (i.e. I, Ia, II, or IIa), $R^1$ and $R^2$ are independently —$SR^9$, —$OSO_2R^8$, —$OSO_3H$, —$NH_2NH_2$, —$ONR^6R^7$, —$NH_2C$=(O)$NHNH_2$, —$NH_2C$=(O)$NR^6R^7$, —$NR^5R^6R^7$, —$OC(O)R^8$, —$OC(O)NR^6R^7$, —$OR^9$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In some embodiments, $R^1$ and $R^2$ are independently —$SR^9$, —$OSO_2R^8$, —$OSO_3H$, —$NH_2NH_2$, —$ONR^6R^7$, —$NH_2C$=(O)$NHNH_2$, —$NH_2C$=(O)$NR^6R^7$, —$NR^5R^6R^7$, —$OC(O)R^8$, —$OC(O)NR^6R^7$, —$OR^9$, substituted or unsubstituted heteroalkyl, substituted or unsubstituted heterocycloalkyl, or substituted or unsubstituted heteroaryl. In some embodiments, $R^1$ and $R^2$ may optionally be joined to form a substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In some embodiments, $R^1$ and $R^2$ may optionally be joined to form a substituted or unsubstituted heteroalkyl, substituted or unsubstituted heterocycloalkyl, or substituted or unsubstituted heteroaryl. In some embodiments, $R^3$ is halogen. $R^5$, $R^6$, $R^7$, $R^8$, and $R^9$ are as described herein. In some embodiments, $R^1$ and $R^2$ are independently —$NH_3$. In some embodiments, $R^3$ is —Cl.

In some embodiments of a formula above (i.e. I, Ia, II, or IIa), $R^1$ and $R^3$ are independently —$SR^9$, —$OSO_2R^8$, —$OSO_3H$, —$NH_2NH_2$, —$ONR^6R^7$, —$NH_2C$=(O)$NHNH_2$, —$NH_2C$=(O)$NR^6R^7$, —$NR^5R^6R^7$, —$OC(O)R^8$, —$OC(O)NR^6R^7$, —$OR^9$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In some embodiments, $R^1$ and $R^3$ are independently —$SR^9$, —$OSO_2R^8$, —$OSO_3H$, —$NH_2NH_2$, —$ONR^6R^7$, —$NH_2C$=(O)$NHNH_2$, —$NH_2C$=(O)$NR^6R^7$, —$NR^5R^6R^7$, —$OC(O)R^8$, —$OC(O)NR^6R^7$, —$OR^9$, substituted or unsubstituted heteroalkyl, substituted or unsubstituted heterocycloalkyl, or substituted or unsubstituted heteroaryl. In some embodiments, $R^1$ and $R^3$ may optionally be joined to form a substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In some embodiments, $R^1$ and $R^3$ may optionally be joined to form a substituted or unsubstituted heteroalkyl, substituted or unsubstituted heterocycloalkyl, or substituted or unsubstituted heteroaryl. In some embodiments, $R^2$ is halogen. $R^5$, $R^6$, $R^7$, $R^8$, and $R^9$ are as described herein. In some embodiments, $R^1$ and $R^3$ are independently —$NH_3$. In some embodiments, $R^2$ is —Cl.

In some embodiments, the compound of formula I or Ia is the compound of formula III or IIIa, respectively:

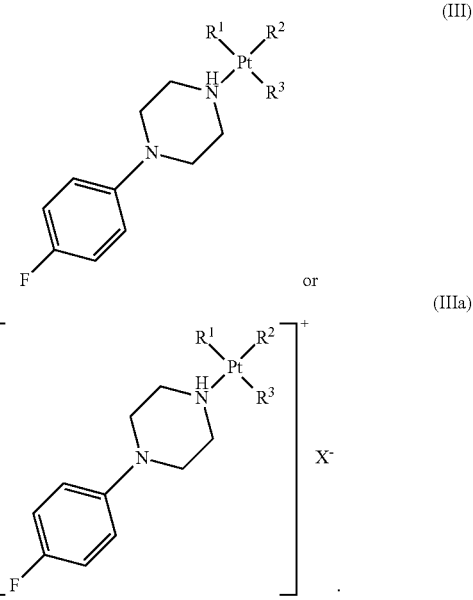

$X^-$, $R^1$, $R^2$, $R^3$, $R^5$, $R^6$, $R^7$, $R^8$, $R^9$, Y, m, q, and u are as defined above.

In some embodiments, the compound of formula I is the compound of formula IV:

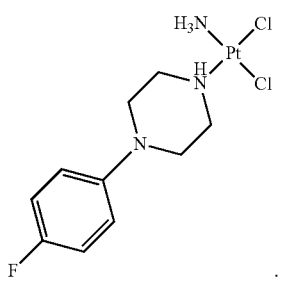

(IV)

In some embodiments, the compound of formula I is the compound of formula V:

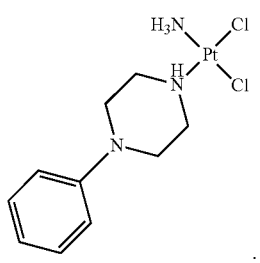

(V)

In some embodiments of the compounds provided herein, $R^1$ is halogen, —OH, —$NH_3$, —OC(O)H, —OC(O)$NH_2$, —SH, —O$SO_3$H, —O$SO_2$H, —$NH_2NH_2$, —O$NH_2$, —$NH_2$C=(O)$NH_2$, —$NH_2$C=(O)NH$NH_2$, $R^{15}$-substituted or unsubstituted alkyl, $R^{15}$-substituted or unsubstituted heteroalkyl, $R^{15}$-substituted or unsubstituted cycloalkyl, $R^{15}$-substituted or unsubstituted heterocycloalkyl, $R^{15}$-substituted or unsubstituted aryl, or $R^{15}$-substituted or unsubstituted heteroaryl. In some embodiments, $R^1$ is halogen, —OH, —$NH_3$, —OC(O)H, —OC(O)$NH_2$, —SH, —O$SO_3$H, —O$SO_2$H, —$NH_2NH_2$, —O$NH_2$, —$NH_2$C=(O)$NH_2$, —$NH_2$C=(O)NH$NH_2$, $R^{15}$-substituted or unsubstituted heteroalkyl, $R^{15}$-substituted or unsubstituted heterocycloalkyl, or $R^{15}$-substituted or unsubstituted heteroaryl. In some embodiments of the compounds provided herein, $R^1$ is a ligand of the coordination complex, bonded to a central platinum by a coordinate or coordinate covalent bond. In some embodiments of the compounds provided herein, $R^1$ contributes a lone pair of electrons from a donor atom. In some embodiments, the $R^1$ donor atom is a heteroatom. In some embodiments, the $R^1$ donor atom is a nitrogen.

$R^{15}$ is independently halogen, —$CF_3$, —CN, —OH, —$NH_2$, —COOH, —CO$NH_2$, —$NO_2$, —SH, —$SO_2$Cl, —$SO_3$H, —$SO_4$H, —$SO_2NH_2$, —NH$NH_2$, —O$NH_2$, —NHC=(O)NH$NH_2$, $R^{16}$-substituted or unsubstituted alkyl, $R^{16}$-substituted or unsubstituted heteroalkyl, $R^{16}$-substituted or unsubstituted cycloalkyl, $R^{16}$-substituted or unsubstituted heterocycloalkyl, $R^{16}$-substituted or unsubstituted aryl, or $R^{16}$-substituted or unsubstituted heteroaryl.

$R^{16}$ is independently halogen, —$CF_3$, —CN, —OH, —$NH_2$, —COOH, —CO$NH_2$, —$NO_2$, —SH, —$SO_2$Cl, —$SO_3$H, —$SO_4$H, —$SO_2NH_2$, —NH$NH_2$, —O$NH_2$, —NHC=(O)NH$NH_2$, $R^{17}$-substituted or unsubstituted alkyl, $R^{17}$-substituted or unsubstituted heteroalkyl, $R^{17}$-substituted or unsubstituted cycloalkyl, $R^{17}$-substituted or unsubstituted heterocycloalkyl, $R^{17}$-substituted or unsubstituted aryl, or $R^{17}$-substituted or unsubstituted heteroaryl.

In some embodiments of the compounds provided herein, $R^2$ is halogen, —OH, —$NH_3$, —OC(O)H, —OC(O)$NH_2$, —SH, —O$SO_3$H, —O$SO_2$H, —$NH_2NH_2$, —O$NH_2$, —$NH_2$C=(O)$NH_2$, —$NH_2$C=(O)NH$NH_2$, $R^{18}$-substituted or unsubstituted alkyl, $R^{18}$-substituted or unsubstituted heteroalkyl, $R^{18}$-substituted or unsubstituted cycloalkyl, $R^{18}$-substituted or unsubstituted heterocycloalkyl, $R^{18}$-substituted or unsubstituted aryl, or $R^{18}$-substituted or unsubstituted heteroaryl. In some embodiments, $R^2$ is halogen, —OH, —$NH_3$, —OC(O)H, —OC(O)$NH_2$, —SH, —O$SO_3$H, —O$SO_2$H, —$NH_2NH_2$, —O$NH_2$, —$NH_2$C=(O)$NH_2$, —$NH_2$C=(O)NH$NH_2$, $R^{18}$-substituted or unsubstituted heteroalkyl, $R^{18}$-substituted or unsubstituted heterocycloalkyl, or $R^{18}$-substituted or unsubstituted heteroaryl. In some embodiments of the compounds provided herein, $R^2$ is a ligand of the coordination complex, bonded to a central platinum by a coordinate or coordinate covalent bond. In some embodiments of the compounds provided herein, $R^2$ contributes a lone pair of electrons from a donor atom. In some embodiments, the $R^2$ donor atom is a heteroatom. In some embodiments, the $R^2$ donor atom is a nitrogen.

$R^{18}$ is independently halogen, —$CF_3$, —CN, —OH, —$NH_2$, —COOH, —CO$NH_2$, —$NO_2$, —SH, —$SO_2$Cl, —$SO_3$H, —$SO_4$H, —$SO_2NH_2$, —NH$NH_2$, —O$NH_2$, —NHC=(O)NH$NH_2$, $R^{19}$-substituted or unsubstituted alkyl, $R^{19}$-substituted or unsubstituted heteroalkyl, $R^{19}$-substituted or unsubstituted cycloalkyl, $R^{19}$-substituted or unsubstituted heterocycloalkyl, $R^{19}$-substituted or unsubstituted aryl, or $R^{19}$-substituted or unsubstituted heteroaryl.

$R^{19}$ independently is halogen, —$CF_3$, —CN, —OH, —$NH_2$, —COOH, —CO$NH_2$, —$NO_2$, —SH, —$SO_2$Cl, —$SO_3$H, —$SO_4$H, —$SO_2NH_2$, —NH$NH_2$, —O$NH_2$, —NHC=(O)NH$NH_2$, $R^{20}$-substituted or unsubstituted alkyl, $R^{20}$-substituted or unsubstituted heteroalkyl, $R^{20}$-substituted or unsubstituted cycloalkyl, $R^{20}$-substituted or unsubstituted heterocycloalkyl, $R^{20}$-substituted or unsubstituted aryl, or $R^{20}$-substituted or unsubstituted heteroaryl.

In some embodiments of the compounds provided herein, $R^3$ is halogen, —OH, —$NH_3$, —OC(O)H, —OC(O)$NH_2$, —SH, —O$SO_3$H, —O$SO_2$H, —$NH_2NH_2$, —O$NH_2$, —$NH_2$C=(O)$NH_2$, —$NH_2$C=(O)NH$NH_2$, $R^{21}$-substituted or unsubstituted alkyl, $R^{21}$-substituted or unsubstituted heteroalkyl, $R^{21}$-substituted or unsubstituted cycloalkyl, $R^{21}$-substituted or unsubstituted heterocycloalkyl, $R^{21}$-substituted or unsubstituted aryl, or $R^{21}$-substituted or unsubstituted heteroaryl. In some embodiments, $R^3$ is halogen, —OH, —$NH_3$, —OC(O)H, —OC(O)$NH_2$, —SH, —O$SO_3$H, —O$SO_2$H, —$NH_2NH_2$, —O$NH_2$, —$NH_2$C=(O)$NH_2$, —$NH_2$C=(O)NH$NH_2$, $R^{21}$-substituted or unsubstituted heteroalkyl, $R^{21}$-substituted or unsubstituted heterocycloalkyl, or $R^{21}$-substituted or unsubstituted heteroaryl. In some embodiments of the compounds provided herein, $R^3$ is a ligand of the coordination complex, bonded to a central platinum by a coordinate or coordinate covalent bond. In some embodiments of the compounds provided herein, $R^3$ contributes a lone pair of electrons from a donor atom. In some embodiments, the $R^3$ donor atom is a heteroatom. In some embodiments, the $R^3$ donor atom is a nitrogen.

$R^{21}$ is independently halogen, —$CF_3$, —CN, —OH, —$NH_2$, —COOH, —CO$NH_2$, —$NO_2$, —SH, —$SO_2$Cl, —$SO_3$H, —$SO_4$H, —$SO_2NH_2$, —NH$NH_2$, —O$NH_2$, —NHC=(O)NH$NH_2$, $R^{22}$-substituted or unsubstituted alkyl, $R^{22}$-substituted or unsubstituted heteroalkyl, $R^{22}$-substituted or unsubstituted cycloalkyl, $R^{22}$ substituted or unsubstituted heterocycloalkyl, $R^{22}$-substituted or unsubstituted aryl, or $R^{22}$-substituted or unsubstituted heteroaryl.

$R^{22}$ is independently halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, $R^{23}$-substituted or unsubstituted alkyl, $R^{23}$-substituted or unsubstituted heteroalkyl, $R^{23}$-substituted or unsubstituted cycloalkyl, $R^{23}$-substituted or unsubstituted heterocycloalkyl, $R^{23}$-substituted or unsubstituted aryl, or $R^{23}$-substituted or unsubstituted heteroaryl.

In some embodiments of the compounds provided herein, $R^4$ is hydrogen, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, $R^{24}$-substituted or unsubstituted alkyl, $R^{24}$-substituted or unsubstituted heteroalkyl, $R^{24}$-substituted or unsubstituted cycloalkyl, $R^{24}$-substituted or unsubstituted heterocycloalkyl, $R^{24}$-substituted or unsubstituted aryl, or $R^{24}$-substituted or unsubstituted heteroaryl.

In some embodiments of the compounds provided herein, $R^4$ is hydrogen, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, $R^{24}$-substituted or unsubstituted cycloalkyl, $R^{24}$-substituted or unsubstituted heterocycloalkyl, $R^{24}$-substituted or unsubstituted aryl, or $R^{24}$-substituted or unsubstituted heteroaryl.

In some embodiments of the compounds provided herein, $R^4$ is $R^{24}$-substituted or unsubstituted cycloalkyl, $R^{24}$-substituted or unsubstituted heterocycloalkyl, $R^{24}$-substituted or unsubstituted aryl, or $R^{24}$-substituted or unsubstituted heteroaryl.

In some embodiments of the compounds provided herein, $R^4$ is $R^{24}$-substituted or unsubstituted heteroaryl.

In some embodiments of the compounds provided herein, $R^4$ is $R^{24}$-substituted or unsubstituted aryl.

In some embodiments of the compounds provided herein, $R^4$ is $R^{24}$-substituted or unsubstituted heterocycloalkyl.

In some embodiments of the compounds provided herein, $R^4$ is $R^{24}$-substituted or unsubstituted cycloalkyl.

$R^{24}$ is independently halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, $R^{25}$-substituted or unsubstituted alkyl, $R^{25}$-substituted or unsubstituted heteroalkyl, $R^{25}$-substituted or unsubstituted cycloalkyl, $R^{25}$ substituted or unsubstituted heterocycloalkyl, $R^{25}$-substituted or unsubstituted aryl, or $R^{25}$-substituted or unsubstituted heteroaryl.

$R^{25}$ is independently halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, $R^{26}$-substituted or unsubstituted alkyl, $R^{26}$-substituted or unsubstituted heteroalkyl, $R^{26}$-substituted or unsubstituted cycloalkyl, $R^{26}$-substituted or unsubstituted heterocycloalkyl, $R^{26}$-substituted or unsubstituted aryl, or $R^{26}$-substituted or unsubstituted heteroaryl.

In some embodiments of the compounds provided herein, $R^5$ is hydrogen, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, $R^{27}$-substituted or unsubstituted alkyl, $R^{27}$-substituted or unsubstituted heteroalkyl, $R^{27}$-substituted or unsubstituted cycloalkyl, $R^{27}$-substituted or unsubstituted heterocycloalkyl, $R^{27}$-substituted or unsubstituted aryl, or $R^{27}$-substituted or unsubstituted heteroaryl. As indicated above, in some embodiments, $R^5$ may be independently $R^{5A}$, $R^{5B}$ or $R^{5C}$ where serving as a substituent of $R^1$, $R^2$ or $R^3$, respectively. Therefore, a person having ordinary skill in the art will immediately understand that, in some embodiments, $R^{27}$ may be independently $R^{27A}$, $R^{27B}$ or $R^{27C}$ where serving as a subsistent of $R^{5A}$, $R^{5B}$ or $R^{5C}$, respectively.

$R^{27}$ is independently halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, $R^{28}$-substituted or unsubstituted alkyl, $R^{28}$-substituted or unsubstituted heteroalkyl, $R^{28}$-substituted or unsubstituted cycloalkyl, $R^{28}$ substituted or unsubstituted heterocycloalkyl, $R^{28}$-substituted or unsubstituted aryl, or $R^{28}$-substituted or unsubstituted heteroaryl. As discussed above, a person having ordinary skill in the art will immediately understand that, in some embodiments, $R^{28}$ may be independently $R^{28A}$, $R^{28B}$ or $R^{28C}$ where serving as a subsistent of $R^{27A}$, $R^{27B}$ or $R_{27C}$, respectively.

$R^{28}$ is independently halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, $R^{29}$-substituted or unsubstituted alkyl, $R^{29}$-substituted or unsubstituted heteroalkyl, $R^{29}$-substituted or unsubstituted cycloalkyl, $R^{29}$-substituted or unsubstituted heterocycloalkyl, $R^{29}$-substituted or unsubstituted aryl, or $R^{29}$-substituted or unsubstituted heteroaryl. As discussed above, a person having ordinary skill in the art will immediately understand that, in some embodiments, $R^{29}$ may be independently $R^{29A}$, $R^{29B}$ or $R^{29C}$ where serving as a subsistent of $R^{28A}$, $R^{28B}$ or $R^{28C}$, respectively.

In some embodiments of the compounds provided herein, $R^6$ is hydrogen, halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, $R^{30}$-substituted or unsubstituted alkyl, $R^{30}$-substituted or unsubstituted heteroalkyl, $R^{30}$-substituted or unsubstituted cycloalkyl, $R^{30}$-substituted or unsubstituted heterocycloalkyl, $R^{30}$-substituted or unsubstituted aryl, or $R^{30}$-substituted or unsubstituted heteroaryl. As indicated above, in some embodiments, $R^6$ may be independently $R^{6A}$, $R^{6B}$ or $R^{6C}$ where serving as a substituent of $R^1$, $R^2$ or $R^3$, respectively. Therefore, a person having ordinary skill in the art will immediately understand that, in some embodiments, $R^{30}$ may be independently $R^{30A}$, $R^{30B}$ or $R^{30C}$ where serving as a subsistent of $R^{6A}$, $R^{6B}$ or $R^{6C}$, respectively.

$R^{30}$ is independently halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, $R^{31}$-substituted or unsubstituted alkyl, $R^{31}$-substituted or unsubstituted heteroalkyl, $R^{31}$-substituted or unsubstituted cycloalkyl, $R^{31}$ substituted or unsubstituted heterocycloalkyl, $R^{31}$-substituted or unsubstituted aryl, or $R^{31}$-substituted or unsubstituted heteroaryl. As discussed above, a person having ordinary skill in the art will immediately understand that, in some embodiments, $R^{31}$ may be independently $R^{31A}$, $R^{31B}$ or $R^{31C}$ where serving as a subsistent of $R^{30A}$, $R^{30B}$ or $R^{30C}$, respectively.

$R^{31}$ is independently halogen, —$CF_3$, —CN, —OH, —$NH_2$, —COOH, —$CONH_2$, —$NO_2$, —SH, —$SO_2Cl$, —$SO_3H$, —$SO_4H$, —$SO_2NH_2$, —$NHNH_2$, —$ONH_2$, —NHC=(O)$NHNH_2$, $R^{32}$-substituted or unsubstituted alkyl, $R^{32}$-substituted or unsubstituted heteroalkyl, $R^{32}$-substituted or unsubstituted cycloalkyl, $R^{32}$-substituted or unsubstituted heterocycloalkyl, $R^{32}$-substituted or unsubstituted aryl, or $R^{32}$-substituted or unsubstituted heteroaryl. As discussed above, a person having ordinary skill in the art will immediately understand that, in some embodiments, $R^{32}$ may be independently $R^{32A}$, $R^{32B}$ or $R^{32C}$ where serving as a subsistent of $R^{31A}$, $R^{31B}$ or $R^{31C}$, respectively.

In some embodiments of the compounds provided herein, $R^7$ is hydrogen, halogen, —$CF_3$, —CN, —OH, —$NH_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, $R^{33}$-substituted or unsubstituted alkyl, $R^{33}$-substituted or unsubstituted heteroalkyl, $R^{33}$-substituted or unsubstituted cycloalkyl, $R^{33}$-substituted or unsubstituted heterocycloalkyl, $R^{33}$-substituted or unsubstituted aryl, or $R^{33}$-substituted or unsubstituted heteroaryl. As indicated above, in some embodiments, $R^7$ may be independently $R^{7A}$, $R^{7B}$ or $R^{7C}$ where serving as a substituent of $R^1$, $R^2$ or $R^3$, respectively. Therefore, a person having ordinary skill in the art will immediately understand that, in some embodiments, $R^{33}$ may be independently $R^{33A}$, $R^{33B}$ or $R^{33C}$ where serving as a subsistent of $R^{7A}$, $R^{7B}$ or $R^{7C}$, respectively.

$R^{33}$ is independently halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, $R^{34}$-substituted or unsubstituted alkyl, $R^{34}$-substituted or unsubstituted heteroalkyl, $R^{34}$-substituted or unsubstituted cycloalkyl, $R^{34}$ substituted or unsubstituted heterocycloalkyl, $R^{34}$-substituted or unsubstituted aryl, or $R^{34}$-substituted or unsubstituted heteroaryl. As discussed above, a person having ordinary skill in the art will immediately understand that, in some embodiments, $R^{34}$ may be independently $R^{34A}$, $R^{34B}$ or $R^{34C}$ where serving as a subsistent of $R^{33A}$, $R^{33B}$ or $R^{33C}$, respectively.

$R^{34}$ is independently halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, $R^{35}$-substituted or unsubstituted alkyl, $R^{35}$-substituted or unsubstituted heteroalkyl, $R^{35}$-substituted or unsubstituted cycloalkyl, $R^{35}$-substituted or unsubstituted heterocycloalkyl, $R^{35}$-substituted or unsubstituted aryl, or $R^{35}$-substituted or unsubstituted heteroaryl. As discussed above, a person having ordinary skill in the art will immediately understand that, in some embodiments, $R^{35}$ may be independently $R^{35A}$, $R^{35B}$ or $R^{35C}$ where serving as a subsistent of $R^{34A}$, $R^{34B}$ or $R^{34C}$, respectively.

In some embodiments of the compounds provided herein, $R^8$ is hydrogen, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, $R^{36}$-substituted or unsubstituted alkyl, $R^{36}$-substituted or unsubstituted heteroalkyl, $R^{36}$-substituted or unsubstituted cycloalkyl, $R^{36}$-substituted or unsubstituted heterocycloalkyl, $R^{36}$-substituted or unsubstituted aryl, or $R^{36}$-substituted or unsubstituted heteroaryl. As indicated above, $R^8$ may be independently $R^{8A}$, $R^{8B}$ or $R^{8C}$ where serving as a substituent of $R^1$, $R^2$ or $R^3$, respectively. Therefore, a person having ordinary skill in the art will immediately understand that, in some embodiments, $R^{36}$ may be independently $R^{36A}$, $R^{36B}$ or $R^{36C}$ where serving as a subsistent of $R^{8A}$, $R^{8B}$ or $R^{8C}$, respectively.

$R^{36}$ is independently halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, $R^{37}$-substituted or unsubstituted alkyl, $R^{37}$-substituted or unsubstituted heteroalkyl, $R^{37}$-substituted or unsubstituted cycloalkyl, $R^{37}$ substituted or unsubstituted heterocycloalkyl, $R^{37}$-substituted or unsubstituted aryl, or $R^{37}$-substituted or unsubstituted heteroaryl. As discussed above, a person having ordinary skill in the art will immediately understand that, in some embodiments, $R^{37}$ may be independently $R^{37A}$, $R^{37B}$ or $R^{37C}$ where serving as a subsistent of $R^{36A}$, $R^{36B}$ or $R^{36C}$, respectively.

$R^{37}$ is independently halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, $R^{38}$-substituted or unsubstituted alkyl, $R^{38}$-substituted or unsubstituted heteroalkyl, $R^{38}$-substituted or unsubstituted cycloalkyl, $R^{38}$-substituted or unsubstituted heterocycloalkyl, $R^{38}$-substituted or unsubstituted aryl, or $R^{38}$-substituted or unsubstituted heteroaryl. As discussed above, a person having ordinary skill in the art will immediately understand that, in some embodiments, $R^{38B}$ may be independently $R^{38A}$, $R^{38B}$ or $R^{38C}$ where serving as a subsistent of $R^{37A}$, $R^{37B}$ or $R^{37C}$, respectively.

In some embodiments of the compounds provided herein, $R^9$ is hydrogen, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, $R^{39}$-substituted or unsubstituted alkyl, $R^{39}$-substituted or unsubstituted heteroalkyl, $R^{39}$-substituted or unsubstituted cycloalkyl, $R^{39}$-substituted or unsubstituted heterocycloalkyl, $R^{39}$-substituted or unsubstituted aryl, or $R^{39}$-substituted or unsubstituted heteroaryl. As indicated above, in some embodiments, $R^9$ may be independently $R^{9A}$, $R^{9B}$ or $R^{9C}$ where serving as a substituent of $R^1$, $R^2$ or $R^3$, respectively. Therefore, a person having ordinary skill in the art will immediately understand that, in some embodiments, $R^{39}$ may be independently $R^{39A}$, $R^{39B}$ or $R^{39C}$ where serving as a subsistent of $R^{9A}$, $R^{9B}$ or $R^{9C}$, respectively.

$R^{39}$ is independently halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, $R^{40}$-substituted or unsubstituted alkyl, $R^{40}$-substituted or unsubstituted heteroalkyl, $R^{40}$-substituted or unsubstituted cycloalkyl, $R^{40}$ substituted or unsubstituted heterocycloalkyl, $R^{40}$-substituted or unsubstituted aryl, or $R^{40}$-substituted or unsubstituted heteroaryl. As discussed above, a person having ordinary skill in the art will immediately understand that, in some embodiments, $R^{40}$ may be independently $R^{40A}$, $R^{40B}$ or $R^{40C}$ where serving as a subsistent of $R^{39A}$, $R^{39B}$ or $R^{39C}$, respectively.

$R^{40}$ is independently halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, $R^{41}$-substituted or unsubstituted alkyl, $R^{41}$-substituted or unsubstituted heteroalkyl, $R^{41}$-substituted or unsubstituted cycloalkyl, $R^{41}$-substituted or unsubstituted heterocycloalkyl, $R^{41}$-substituted or unsubstituted aryl, or $R^{41}$-substituted or unsubstituted heteroaryl. As discussed above, a person having ordinary skill in the art will immediately understand that, in some embodiments, $R^{41}$ may be independently $R^{41A}$, $R^{41B}$ or $R^{41C}$ where serving as a subsistent of $R^{40A}$, $R^{40B}$ or $R^{40C}$, respectively.

In some embodiments of the compounds provided herein, $R^{10}$ is hydrogen, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, $R^{42}$-substituted or unsubstituted alkyl, $R^{42}$-substituted or unsubstituted heteroalkyl, $R^{42}$-substituted or unsubstituted cycloalkyl, $R^{42}$-substituted or unsubstituted heterocycloalkyl, $R^{42}$-substituted or unsubstituted aryl, or $R^{42}$-substituted or unsubstituted heteroaryl.

$R^{42}$ is independently halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, R$^{43}$-substituted or unsubstituted alkyl, R$^{43}$-substituted or unsubstituted heteroalkyl, R$^{43}$-substituted or unsubstituted cycloalkyl, R$^{43}$ substituted or unsubstituted heterocycloalkyl, R$^{43}$-substituted or unsubstituted aryl, or R$^{43}$-substituted or unsubstituted heteroaryl.

R$^{43}$ is independently halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, R$^{44}$-substituted or unsubstituted alkyl, R$^{44}$-substituted or unsubstituted heteroalkyl, R$^{44}$-substituted or unsubstituted cycloalkyl, R$^{44}$-substituted or unsubstituted heterocycloalkyl, R$^{44}$-substituted or unsubstituted aryl, or R$^{44}$-substituted or unsubstituted heteroaryl.

In some embodiments of the compounds provided herein, R$^{11}$ is hydrogen, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, R$^{45}$-substituted or unsubstituted alkyl, R$^{45}$-substituted or unsubstituted heteroalkyl, R$^{45}$-substituted or unsubstituted cycloalkyl, R$^{45}$-substituted or unsubstituted heterocycloalkyl, R$^{45}$-substituted or unsubstituted aryl, or R$^{45}$-substituted or unsubstituted heteroaryl.

R$^{45}$ is independently halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, R$^{46}$-substituted or unsubstituted alkyl, R$^{46}$-substituted or unsubstituted heteroalkyl, R$^{46}$-substituted or unsubstituted cycloalkyl, R$^{46}$ substituted or unsubstituted heterocycloalkyl, R$^{46}$-substituted or unsubstituted aryl, or R$^{46}$-substituted or unsubstituted heteroaryl.

R$^{46}$ is independently halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, R$^{47}$-substituted or unsubstituted alkyl, R$^{47}$-substituted or unsubstituted heteroalkyl, R$^{47}$-substituted or unsubstituted cycloalkyl, R$^{47}$-substituted or unsubstituted heterocycloalkyl, R$^{47}$-substituted or unsubstituted aryl, or R$^{47}$-substituted or unsubstituted heteroaryl.

In some embodiments of the compounds provided herein, R$^{12}$ is hydrogen, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, R$^{48}$-substituted or unsubstituted alkyl, R$^{48}$-substituted or unsubstituted heteroalkyl, R$^{48}$-substituted or unsubstituted cycloalkyl, R$^{48}$-substituted or unsubstituted heterocycloalkyl, R$^{48}$-substituted or unsubstituted aryl, or R$^{48}$-substituted or unsubstituted heteroaryl.

R$^{48}$ is independently halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, R$^{49}$-substituted or unsubstituted alkyl, R$^{49}$-substituted or unsubstituted heteroalkyl, R$^{49}$-substituted or unsubstituted cycloalkyl, R$^{49}$ substituted or unsubstituted heterocycloalkyl, R$^{49}$-substituted or unsubstituted aryl, or R$^{49}$-substituted or unsubstituted heteroaryl.

R$^{49}$ is independently halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, R$^{50}$-substituted or unsubstituted alkyl, R$^{50}$-substituted or unsubstituted heteroalkyl, R$^{50}$-substituted or unsubstituted cycloalkyl, R$^{50}$-substituted or unsubstituted heterocycloalkyl, R$^{50}$-substituted or unsubstituted aryl, or R$^{50}$-substituted or unsubstituted heteroaryl.

In some embodiments of the compounds provided herein, R$^{13}$ is hydrogen, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, R$^{51}$-substituted or unsubstituted alkyl, R$^{51}$-substituted or unsubstituted heteroalkyl, R$^{51}$-substituted or unsubstituted cycloalkyl, R$^{51}$-substituted or unsubstituted heterocycloalkyl, R$^{51}$-substituted or unsubstituted aryl, or R$^{51}$-substituted or unsubstituted heteroaryl.

R$^{51}$ is independently halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, R$^{52}$-substituted or unsubstituted alkyl, R$^{52}$-substituted or unsubstituted heteroalkyl, R$^{52}$-substituted or unsubstituted cycloalkyl, R$^{52}$ substituted or unsubstituted heterocycloalkyl, R$^{52}$-substituted or unsubstituted aryl, or R$^{52}$-substituted or unsubstituted heteroaryl.

R$^{52}$ is independently halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, R$^{53}$-substituted or unsubstituted alkyl, R$^{53}$-substituted or unsubstituted heteroalkyl, R$^{53}$-substituted or unsubstituted cycloalkyl, R$^{53}$-substituted or unsubstituted heterocycloalkyl, R$^{53}$-substituted or unsubstituted aryl, or R$^{53}$-substituted or unsubstituted heteroaryl.

In a further embodiment of the compounds provided herein, R$^{14}$ is hydrogen, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, R$^{54}$-substituted or unsubstituted alkyl, R$^{54}$-substituted or unsubstituted heteroalkyl, R$^{54}$-substituted or unsubstituted cycloalkyl, R$^{54}$-substituted or unsubstituted heterocycloalkyl, R$^{54}$-substituted or unsubstituted aryl, or R$^{54}$-substituted or unsubstituted heteroaryl.

R$^{54}$ is independently halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, R$^{55}$-substituted or unsubstituted alkyl, R$^{55}$-substituted or unsubstituted heteroalkyl, R$^{55}$-substituted or unsubstituted cycloalkyl, R$^{55}$-substituted or unsubstituted heterocycloalkyl, R$^{55}$-substituted or unsubstituted aryl, or R$^{55}$-substituted or unsubstituted heteroaryl.

R$^{55}$ independently is halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, R$^{56}$-substituted or unsubstituted alkyl, R$^{56}$-substituted or unsubstituted heteroalkyl, R$^{56}$-substituted or unsubstituted cycloalkyl, R$^{56}$-substituted or unsubstituted heterocycloalkyl, R$^{56}$-substituted or unsubstituted aryl, or R$^{56}$-substituted or unsubstituted heteroaryl.

In some embodiments of the compounds provided herein, R$^{17}$, R$^{20}$, R$^{23}$, R$^{26}$, R$^{29}$, R$^{32}$, R$^{35}$, R$^{38}$, R$^{41}$, R$^{44}$, R$^{47}$, R$^{50}$, R$^{53}$, R$^{56}$, are independently hydrogen, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, unsubstituted alkyl, unsubstituted heteroalkyl, unsubstituted cycloalkyl, unsubstituted heterocycloalkyl, unsubstituted aryl, or unsubstituted heteroaryl.

In some embodiments, the compound is a compounds of Table 9 below:

TABLE 9

| Compound Structure | IC$_{50}$ HEK-MOCK (μM) | IC$_{50}$ HEK-hOCT1 (μM) | IC$_{50}$ HEK-hOCT2 (μM) |
|---|---|---|---|
| SM71 | 49.96 ± 2.030 | 0.745 ± 0.003 | 1.258 ± 0.319 |
| SM73 | 12.35 ± 0.759 | 0.036 ± 0.004 | 0.005 ± 0.001 |
| SM85 | 8.100 ± 1.256 | 0.071 ± 0.014 | 0.208 ± 0.035 |
| SM39 | 11.983 | 7.513 | 12.88 |
| SM78 | 134.4 ± 19.18 | 0.988 ± 0.030 | 2.351 ± 0.313 |

III. Pharmaceutical Compositions and Methods of Treatment

In a second aspect, provided is a pharmaceutical composition including a pharmaceutically acceptable excipient and a compound as described herein (e.g. formula I, Ia, II, IIa, III, IIIa, IV, or V, including embodiments), or a pharmaceutically acceptable salt of a compound described herein.

The pharmaceutical compositions include optical isomers, diastereomers, or pharmaceutically acceptable salts of the compounds disclosed herein. The compound included in the pharmaceutical composition may be covalently attached to a carrier moiety. Alternatively, the compound included in the pharmaceutical composition is not covalently linked to a carrier moiety.

The compounds of the present invention can be prepared and administered in a wide variety of oral, parenteral and topical dosage forms. Oral preparations include tablets, pills, powder, dragees, capsules, liquids, lozenges, cachets, gels, syrups, slurries, suspensions, etc., suitable for ingestion by the patient. The compounds of the present invention can also be administered by injection, that is, intravenously, intramuscularly, intracutaneously, subcutaneously, intraduodenally, or intraperitoneally. Also, the compounds described herein can be administered by inhalation, for example, intranasally. Additionally, the compounds of the present invention can be administered transdermally. It is also envisioned that multiple routes of administration (e.g., intramuscular, oral, transdermal) can be used to administer the compounds of the invention. Accordingly, the present invention also provides pharmaceutical compositions comprising a pharmaceutically acceptable excipient and one or more compounds of the invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substance, that may also act as diluents, flavoring agents, binders, preservatives, tablet disintegrating agents, or an encapsulating material.

In powders, the carrier is a finely divided solid in a mixture with the finely divided active component (e.g. a compound provided herein. In tablets, the active component is mixed with the carrier having the necessary binding properties in suitable proportions and compacted in the shape and size desired. The powders and tablets preferably contain from 5% to 70% of the active compound.

Suitable solid excipients include, but are not limited to, magnesium carbonate; magnesium stearate; talc; pectin; dextrin; starch; tragacanth; a low melting wax; cocoa butter; carbohydrates; sugars including, but not limited to, lactose, sucrose, mannitol, or sorbitol, starch from corn, wheat, rice, potato, or other plants; cellulose such as methyl cellulose, hydroxypropylmethyl-cellulose, or sodium carboxymethyl-cellulose; and gums including arabic and tragacanth; as well as proteins including, but not limited to, gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage). Pharmaceutical preparations of the invention can also be used orally using, for example, push-fit capsules made of gelatin, as well as soft, sealed capsules made of gelatin and a coating such as glycerol or sorbitol.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

When parenteral application is needed or desired, particularly suitable admixtures for the compounds of the invention are injectable, sterile solutions, preferably oily or aqueous solutions, as well as suspensions, emulsions, or implants, including suppositories. In particular, carriers for parenteral administration include aqueous solutions of dextrose, saline, pure water, ethanol, glycerol, propylene glycol, peanut oil, sesame oil, polyoxyethylene-block polymers, and the like. Ampules are convenient unit dosages. The compounds of the invention can also be incorporated into liposomes or administered via transdermal pumps or patches. Pharmaceutical admixtures suitable for use in the present invention are well-known to those of skill in the art and are described, for example, in Pharmaceutical Sciences (17th Ed., Mack Pub. Co., Easton, Pa.) and WO 96/05309, the teachings of both of which are hereby incorporated by reference.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Also included are solid form preparations that are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

Oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, *J. Pharmacol. Exp. Ther.* 281:93-102, 1997. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10000 mg, more typically 1.0 mg to 1000 mg, most typically 10 mg to 500 mg, according to the particular application and the potency of the active component. The composition can, if desired, also contain other compatible therapeutic agents.

Some compounds may have limited solubility in water and therefore may require a surfactant or other appropriate co-solvent in the composition. Such co-solvents include: Polysorbate 20, 60 and 80; Pluronic F-68, F-84 and P-103; cyclodextrin; polyoxyl 35 castor oil; or other agents known to those skilled in the art. Such co-solvents are typically employed at a level between about 0.01% and about 2% by weight.

Viscosity greater than that of simple aqueous solutions may be desirable to decrease variability in dispensing the formulations, to decrease physical separation of components of a suspension or emulsion of formulation and/or otherwise to improve the formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, combinations of the foregoing, and other agents known to those skilled in the art. Such agents are typically employed at a level between about 0.01% and about 2% by weight. Determination of acceptable amounts of any of the above adjuvants is readily ascertained by one skilled in the art.

The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes.

Pharmaceutical compositions provided by the present invention include compositions wherein the active ingredient is contained in a therapeutically effective amount, i.e., in an amount effective to achieve its intended purpose. The actual amount effective for a particular application will depend, inter alia, on the condition being treated. When administered in methods to treat a disease, such compositions will contain an amount of active ingredient effective to achieve the desired result, e.g., modulating the activity of a target molecule (e.g. OCT1, OCT2, and/or OCT3 or NET), and/or reducing, eliminating, or slowing the progression of disease symptoms. Determination of a therapeutically effective amount of a compound of the invention is well within the capabilities of those skilled in the art, especially in light of the detailed disclosure herein.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated (e.g., cancer, colorectal cancer, liver cancer, prostate cancer, renal cancer, bladder cancer, ovarian cancer, breast cancer, lung cancer, leukemia, B-cell lymphoma, non-Hodgkin's lymphoma, Burkitt's lymphoma, Small Cell, and Large Cell lymphomas, multiple myeloma, or other cancers that express one or more of the OCTs, neuroendocrine cancers, glioblastoma multiforme, glioma, neuroblastoma, brain cancer, or other cancers that express NET), kind of concurrent treatment, complications from the disease being treated or other health-related problems. Other therapeutic regimens or agents can be used in conjunction with the methods and compounds described herein. Adjustment and manipulation of established dosages (e.g., frequency and duration) are well within the ability of those skilled in the art.

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. In one embodiment, the dosage range is 0.001% to 10% w/v. In another embodiment, the dosage range is 0.1% to 5% w/v.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

The ratio between toxicity and therapeutic effect for a particular compound is its therapeutic index and can be expressed as the ratio between $LD_{50}$ (the amount of compound lethal in 50% of the population) and $ED_{50}$ (the amount of compound effective in 50% of the population). Compounds that exhibit high therapeutic indices are preferred. Therapeutic index data obtained from cell culture assays and/or animal studies can be used in formulating a range of dosages for use in humans. The dosage of such compounds preferably lies within a range of plasma concentrations that include the $ED_{50}$ with little or no toxicity. The dosage may vary within this range depending upon the dosage form employed and the route of administration utilized. See, e.g. Fingl et al., In: THE PHARMACOLOGICAL BASIS OF THERAPEUTICS, Ch. 1, p. 1, 1975. The exact formulation, route of administration and dosage can be chosen by the individual physician in view of the patient's condition and the particular method in which the compound is used.

In a third aspect is a method of treating a disease in a patient in need of such treatment, the method including administering a therapeutically effective amount of a compound described herein (e.g. formula I, Ia, II, IIa, III, IIIa, IV, or V, including embodiments).

In some embodiments, the method of treating a disease in a patient in need of such treatment, includes administering a therapeutically effective amount of a compound having the formula:

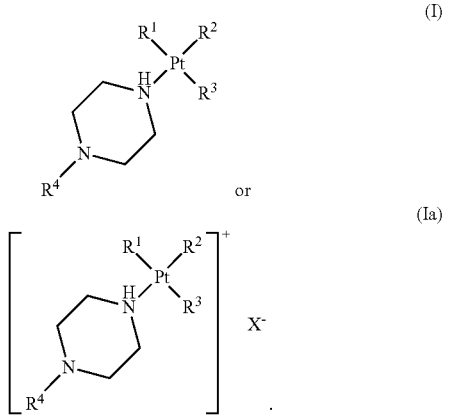

$X^-$, $R^1$, $R^2$, $R^3$, $R^4$, $R^5$, $R^6$, $R^7$, $R^8$, $R^9$, $R^{11}$, $R^{12}$, $R^{13}$, $R^{14}$, Y, m, q, u, and z are as described herein.

In some embodiments, the disease is cancer. In some embodiments, the disease is a cancer that expresses OCT1, OCT2, and/or OCT3. In some embodiments, the disease is a cancer that expresses OCT1. In some embodiments, the disease is a cancer that expresses OCT2. In some embodiments, the disease is a cancer that expresses OCT3. In some embodiments, the disease is a cancer that expresses NET. In some embodiments, the disease is colorectal cancer, liver cancer, hepatocarcinoma, renal cancer, renal cell carcinoma, bladder cancer, lung cancer, non-small cell lung cancer, ovarian cancer, uterine cancer, cervical cancer, testicular cancer, anal cancer, bile duct cancer, biliary tract cancer, gastrointestinal carcinoid tumors, esophageal cancer, gall bladder cancer, appendix cancer, small intestine cancer, stomach (gastric) cancer, urinary bladder cancer, genitourinary tract cancer, endometrial cancer, head and neck cancer, nasopharyngeal cancer, head and neck squamous cell carcinoma, mesothelioma, lymphoma, leukemia, breast cancer, or prostate cancer. In some embodiments, the disease is a disease as described herein. In some embodiments, the disease is sepsis. In some embodiments, the disease is pain. In some embodiments, the disease is neuroendocrine cancer, brain cancer, glioblastoma multiforme, neuroblastoma, or glioma. In some embodiments, the disease is neuroendocrine cancer. In some embodiments, the disease is colorectal cancer. In some embodiments, the disease is liver cancer. In some embodiments, the disease is renal cancer. In some embodiments, the disease is prostate cancer. In some embodiments, the disease is breast cancer. In some embodiments, the disease is testicular cancer.

In some embodiments, the patient has a disease that includes disease-related cells. In some embodiments, the disease-related cells express an organic cation transporter. In some embodiments, the disease-related cells express OCT1. In some embodiments, the disease-related cells express OCT2. In some embodiments, the disease-related cells express OCT3. In some embodiments, the disease-related cells express NET. In some embodiments, the disease-related cells are cancer cells. In some embodiments, the disease-related cells are metastatic cancer cells.

In some embodiments, the method of treatment includes a method of measuring the amount of a transporter in a sample from a patient. In some embodiments, the transporter is an organic cation transporter. In some embodiments, the transporter is OCT1. In some embodiments, the transporter is OCT2. In some embodiments, the transporter is OCT3. In some embodiments, the transporter is NET. In some embodiments, the method of treatment includes a method of measuring the amount of OCT1, OCT2, and/or OCT3 in a sample from a patient. In some embodiments, the sample from a patient comprises disease-related cells. In some embodiments, the disease-related cells express a transporter. In some embodiments, the transporter is an organic cation transporter. In some embodiments, the transporter is OCT1. In some embodiments, the transporter is OCT2. In some embodiments, the transporter is OCT3. In some embodiments, the transporter is NET. In some embodiments, the method of treatment includes a method of measuring the amount of OCT1, OCT2, and/or OCT3 in disease-related cells in a sample from a patient. In some embodiments, the method of treatment includes administering a compound as described herein.

In another aspect is a method of inhibiting replication of DNA in a cell, the method including contacting the cell with a compound as described herein (e.g. formula I, Ia, II, IIa, III, IIIa, IV, or V, including embodiments).

In some embodiments, the compound has formula:

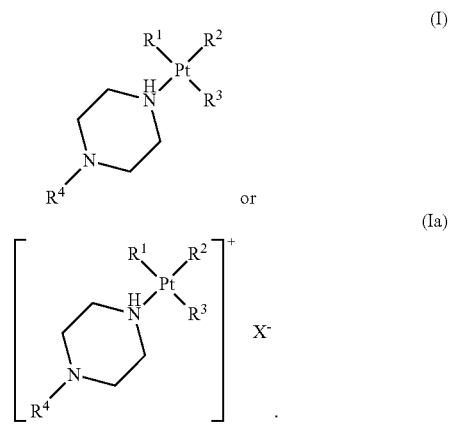

$X^-$, $R^1$, $R^2$, $R^3$, $R^4$, $R^5$, $R^6$, $R^7$, $R^8$, $R^9$, $R^{11}$, $R^{12}$, $R^{13}$, $R^{14}$, Y, m, q, u, and z are as described herein. In some embodiments, the method includes the use of a compound as described herein. In some embodiments, the cell expresses a transporter. In some embodiments, the transporter is an organic cation transporter. In some embodiments, the transporter is OCT1. In some embodiments, the transporter is OCT2. In some embodiments, the transporter is OCT3. In some embodiments, the transporter is NET. In some embodiments, the cell expresses OCT1, OCT2, and/or OCT3. In some embodiments, the cell is a cancer cell. In some embodiments, the cell is a metastatic cancer cell.

In a further aspect, is a method of inducing cell death in a cell, the method including contacting the cell with a compound as described herein (e.g. formula I, Ia, II, IIa, III, IIIa, IV, or V, including embodiments).

In some embodiments, the method includes use of the compound of formula:

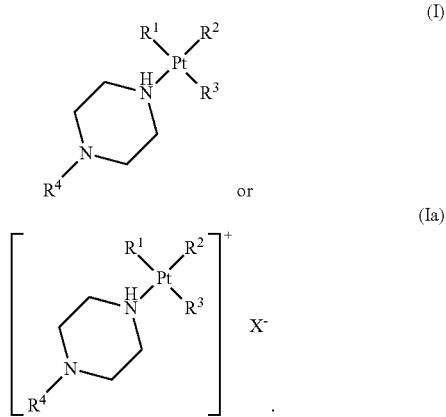

$X^-$, $R^1$, $R^2$, $R^3$, $R^4$, $R^5$, $R^6$, $R^7$, $R^8$, $R^9$, $R^{11}$, $R^{12}$, $R^{13}$, $R^{14}$, Y, m, q, u, and z are as described herein. In some embodiments, the method includes the use of a compound as described herein. In some embodiments, cell death is through apoptosis. In some embodiments, the cell expresses a transporter. In some embodiments, the transporter is an organic cation transporter. In some embodiments, the transporter is OCT1. In some embodiments, the transporter is OCT2. In some embodiments, the transporter is OCT3. In some embodiments, the transporter is NET. In some embodiments, the cell expresses OCT1, OCT2, and/or OCT3. In some embodiments, the cell is a metastatic cancer cell. In some embodiments, the cell is a cancer cell.

In a further aspect, is a method of treating a disease in a patient in need of such treatment, wherein the patient has disease-related cells expressing a norepinephrine transporter protein or mRNA, the method including administering a therapeutically effective amount of a compound as described herein (e.g. formula I, Ia, II, IIa, III, IIIa, IV, or V, including embodiments).

In some embodiments, the method of treating includes administering a compound of the formula:

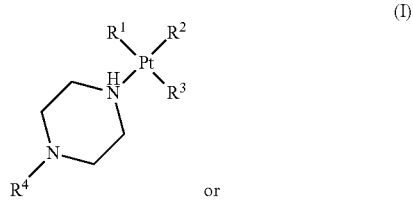

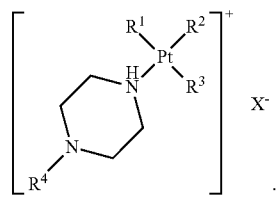

$X^-$, $R^1$, $R^2$, $R^3$, $R^4$, $R^5$, $R^6$, $R^7$, $R^8$, $R^9$, $R^{11}$, $R^{12}$, $R^{13}$, $R^{14}$, Y, m, q, u, and z are as described herein. In some embodiments, the method includes the use of a compound as described herein. In some embodiments, $R^4$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In some embodiments, the disease is cancer. In some embodiments, the cancer is glioblastoma multiforme, neuroblastoma, glioma, neuroendocrine cancer, or brain cancer. In some embodiments, the method includes a method of measuring the amount of a norepinephrine transporter protein or mRNA in a sample from the patient. In some embodiments, the sample includes disease-related cells. In some embodiments, the disease-related cells express a norepinephrine transporter protein or mRNA.

In a further aspect, is a method of inhibiting replication of DNA in a cell, wherein the cell expresses a norepinephrine transporter protein or mRNA, the method including contacting the cell with a compound as described herein (e.g. formula I, Ia, II, IIa, III, IIIa, IV, or V, including embodiments).

In some embodiments, the method includes contacting the cell with the compound of formula:

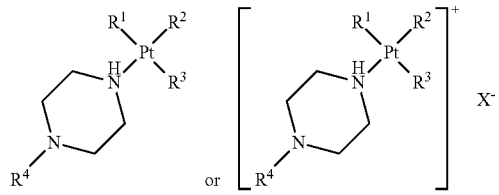

$X^-$, $R^1$, $R^2$, $R^3$, $R^4$, $R^5$, $R^6$, $R^7$, $R^8$, $R^9$, $R^{11}$, $R^{12}$, $R^{13}$, $R^{14}$, Y, m, q, u, and z are as described herein. In some embodiments, the method includes the use of a compound as described herein (e.g. formula I, Ia, II, IIa, III, IIIa, IV, or V, including embodiments). In some embodiments, $R^4$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In some embodiments, the cell is a cancer cell. In some embodiments, the cell is a neuroendocrine cancer cell. In some embodiments, the cell is a glioblastoma multiforme cancer cell. In some embodiments, the cell is a glioma cancer cell. In some embodiments, the cell is a neuroblastoma cancer cell. In some embodiments, the cell is a brain cancer cell. In some embodiments, the cell is a metastatic cancer cell.

In a further aspect is a method of inducing cell death in a cell, wherein the cell expresses a norepinephrine transporter protein or mRNA, the method including contacting the cell with a compound as described herein (e.g. formula I, Ia, II, IIa, III, IIIa, IV, or V, including embodiments).

In some embodiments, the method includes contacting the cell with a compound of formula:

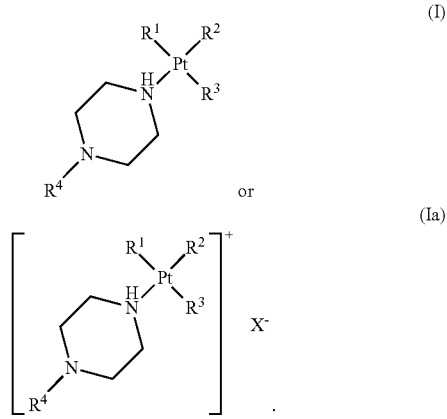

$X^-$, $R^1$, $R^2$, $R^3$, $R^4$, $R^5$, $R^6$, $R^7$, $R^8$, $R^9$, $R^{11}$, $R^{12}$, $R^{13}$, $R^{14}$, Y, m, q, u, and z are as described herein. In some embodiments, the method includes the use of a compound as described herein (e.g. formula I, Ia, II, IIa, III, IIIa, IV, or V, including embodiments). In some embodiments, $R^4$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. In some embodiments, the cell is a cancer cell. In some embodiments, the cell is a neuroendocrine cancer cell. In some embodiments, the cell is a glioblastoma multiforme cancer cell. In some embodiments, the cell is a glioma cancer cell. In some embodiments, the cell is a neuroblastoma cancer cell. In some embodiments, the cell is a brain cancer cell. In some embodiments, cell death is through apoptosis. In some embodiments, the cell is a metastatic cancer cell.

IV. Administration

As described herein, molecules, compositions, and compounds such as platinum-based compounds or drugs that have been identified as substrates for one or more OCT (or NET) are useful in treating cancers that express OCT (or NET) protein or nucleic acid. For therapeutic applications, the platinum-based compounds or drugs of the present invention can be administered alone or co-administered in combination with conventional chemotherapy, radiotherapy, hormonal therapy, and/or immunotherapy.

The compositions of the present invention can be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). Both transdermal and intradermal routes afford constant delivery for weeks or months.

The pharmaceutical compositions of the present invention can be provided as a salt and can be formed with many acids, including but not limited to hydrochloric, sulfuric, acetic, lactic, tartaric, malic, succinic, etc. Pharmaceutical compositions described herein may be salts of a compound or composition which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., *Journal of Pharmaceutical Science* 66:1-19 (1977)). Certain specific compounds of the present invention contain both basic and acidic functionalities that allow the compounds to be converted into either base or acid addition salts. Other pharmaceutically acceptable carriers known to those of skill in the art are suitable for the present invention. Salts tend to be more soluble in aqueous or other protonic solvents that are the corresponding free base forms. In other cases, the preparation may be a lyophilized powder in 1 mM-50 mM histidine, 0.1%-2% sucrose, 2%-7% mannitol at a pH range of 4.5 to 5.5, that is combined with buffer prior to use.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

Certain compositions described herein or platinum-based compounds of the present invention can exist in unsolvated forms as well as solvated forms, including hydrated forms. In general, the solvated forms are equivalent to unsolvated forms and are intended to be encompassed within the scope of the present invention. Certain platinum-based compounds of the present invention may exist in multiple crystalline or amorphous forms. In general, all physical forms are equivalent for the uses contemplated by the present invention and are intended to be within the scope of the present invention.

In another embodiment, the compositions of the present invention are useful for parenteral administration, such as intravenous (IV) administration or administration into a body cavity or lumen of an organ. The formulations for administration will commonly comprise a solution of the compositions of the present invention dissolved in a pharmaceutically acceptable carrier. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of the compositions of the present invention in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol.

In another embodiment, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989).

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The compounds described herein can be used in combination with one another, with other active agents known to be useful in treating a disease associated with cells expressing OCT1, OCT2, and/or OCT3, or NET (e.g. cancer, colorectal cancer, liver cancer, prostate cancer, renal cancer, bladder cancer, ovarian cancer, breast cancer, lung cancer, leukemia, B-cell lymphoma, non-Hodgkin's lymphoma, Burkitt's lymphoma, Small Cell, and Large Cell lymphomas, multiple myeloma, or other cancers that express one or more of the OCTs, neuroendocrine cancers, glioblastoma multiforme, glioma, neuroblastoma, brain cancer, or other cancers that express NET), or with adjunctive agents that may not be effective alone, but may contribute to the efficacy of the active agent.

In some embodiments, co-administration includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. In some embodiments, co-administration can be accomplished by co-formulation, i.e., preparing a single pharmaceutical composition including both active agents. In other embodiments, the active agents can be formulated separately.

In another embodiment, the active and/or adjunctive agents may be linked or conjugated to one another.

As a non-limiting example, the platinum-based compositions and compounds described herein can be co-administered with conventional chemotherapeutic agents including alkylating agents (e.g., cyclophosphamide, ifosfamide, chlorambucil, busulfan, melphalan, mechlorethamine, uramustine, thiotepa, nitrosoureas, etc.), anti-metabolites (e.g., 5-fluorouracil, azathioprine, methotrexate, leucovorin, capecitabine, cytarabine, floxuridine, fludarabine, gemcitabine, pemetrexed, raltitrexed, etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), other platinum-based compounds (e.g. cisplatin, oxaloplatin, carboplatin, a second platinum-based compound described herein), and the like.

The platinum-based compounds or drugs described herein can also be co-administered with conventional hormonal therapeutic agents including, but not limited to, steroids (e.g., dexamethasone), finasteride, aromatase inhibitors, tamoxifen, and gonadotropin-releasing hormone agonists (GnRH) such as goserelin.

Additionally, the platinum-based compounds or drugs described herein can be co-administered with conventional immunotherapeutic agents including, but not limited to, immunostimulants (e.g., Bacillus Calmette-Guérin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-pseudomonas exotoxin conjugate, etc.), and radioimmunotherapy (e.g., anti-CD20 monoclonal antibody conjugated to $^{111}$In, $^{90}$Y, or $^{131}$I, etc.).

In a further embodiment, the platinum-based compounds or drugs described herein can be co-administered with conventional radiotherapeutic agents including, but not limited to, radionuclides such as $^{47}$Sc, $^{64}$Cu, $^{67}$Cu, $^{89}$Sr, $^{86}$Y, $^{87}$Y, $^{90}$Y, $^{105}$Rh, $^{111}$Ag, $^{111}$In, $^{117m}$Sn, $^{149}$Pm, $^{153}$Sm, $^{166}$Ho, $^{177}$Lu, $^{186}$Re, $^{188}$Re, $^{211}$At, and $^{212}$Bi, optionally conjugated to antibodies directed against tumor antigens.

The pharmaceutical compositions of the present invention may be sterilized by conventional, well-known sterilization techniques or may be produced under sterile conditions. Aqueous solutions can be packaged for use or filtered under aseptic conditions and lyophilized, the lyophilized preparation being combined with a sterile aqueous solution prior to administration. The compositions can contain pharmaceutically acceptable auxiliary substances as required to approximate physiological conditions, such as pH adjusting and buffering agents, tonicity adjusting agents, wetting agents, and the like, e.g., sodium acetate, sodium lactate, sodium chloride, potassium chloride, calcium chloride, sorbitan monolaurate, and triethanolamine oleate.

Formulations suitable for oral administration can comprise: (a) liquid solutions, such as an effective amount of a packaged platinum-based compound or drug suspended in diluents, e.g., water, saline, or PEG 400; (b) capsules, sachets, or tablets, each containing a predetermined amount of a platinum-based compound or drug, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise a platinum-based compound or drug in a flavor, e.g., sucrose, as well as pastilles comprising the polypeptide or peptide fragment in an inert base, such as gelatin and glycerin or sucrose and acacia emulsions, gels, and the like, containing, in addition to the polypeptide or peptide, carriers known in the art.

The platinum-based compound or drug of choice, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Suitable formulations for rectal administration include, for example, suppositories, which comprises an effective amount of a packaged platinum-based compound or drug with a suppository base. Suitable suppository bases include natural or synthetic triglycerides or paraffin hydrocarbons. In addition, it is also possible to use gelatin rectal capsules which contain a combination of the platinum-based compound or drug of choice with a base, including, for example, liquid triglycerides, polyethylene glycols, and paraffin hydrocarbons.

Formulations suitable for parenteral administration, such as, for example, by intraarticular (in the joints), intravenous, intramuscular, intratumoral, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Injection solutions and suspensions can also be prepared from sterile powders, granules, and tablets. In the practice of the present invention, compositions can be administered, for example, by intravenous infusion, orally, topically, intraperitoneally, intravesically, or intrathecally. Parenteral administration, oral administration, and intravenous administration are the preferred methods of administration. The formulations of compounds can be presented in unit-dose or multi-dose sealed containers, such as ampoules and vials.

The pharmaceutical preparation is preferably in unit dosage form. In such form the preparation is subdivided into unit doses containing appropriate quantities of the active component, e.g., a platinum-based compound or drug. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The composition can, if desired, also contain other compatible therapeutic agents.

In therapeutic use for the treatment of cancer, the platinum-based compound or drug utilized in the pharmaceutical compositions of the present invention are administered at the initial dosage of about 0.001 mg/kg to about 1000 mg/kg daily. A daily dose range of about 0.01 mg/kg to about 500 mg/kg, or about 0.1 mg/kg to about 200 mg/kg, or about 1 mg/kg to about 100 mg/kg, or about 10 mg/kg to about 50 mg/kg, can be used. The dosages, however, may be varied depending upon the requirements of the patient, the severity of the condition being treated, and the platinum-based compound or drug being employed. For example, dosages can be empirically determined considering the type and stage of cancer diagnosed in a particular patient. The dose administered to a patient, in the context of the present invention, should be sufficient to affect a beneficial therapeutic response in the patient over time. The size of the dose will also be determined by the existence, nature, and extent of any adverse side-effects that accompany the administration of a particular platinum-based compound or drug in a particular patient. Determination of the proper dosage for a particular situation is within the skill of the practitioner. Generally, treatment is initiated with smaller dosages which are less than the optimum dose of the platinum-based compound or drug. Thereafter, the dosage is increased by small increments until the optimum effect under circumstances is reached. For convenience, the total daily dosage may be divided and administered in portions during the day, if desired.

In some embodiments, a pharmaceutical composition as described herein includes a compound selected from the compounds of Table 9.

V. Diagnostic and Prognostic Methods and Compositions

Detection of OCT expression (e.g., OCT1, OCT2, and/or OCT3 expression) or NET expression is particularly useful as an indicator for platinum-based compound therapy, using for example the compounds of described herein, for cancers such as colorectal cancer, liver cancer, prostate cancer, renal cancer, bladder cancer, ovarian cancer, breast cancer, lung cancer, leukemia, B-cell lymphoma (e.g., non-Hodgkin's lymphoma, including Burkitt's, Small Cell, and Large Cell lymphomas), multiple myeloma, glioblastoma multiforme, neuroblastoma, glioma, neuroendocrine cancer, or brain cancer). Detection can include, for example, the level of OCT (or NET) mRNA or protein expression, or the localization (e.g., nuclear, cytoplasmic, cell surface, etc.) of OCT (or NET) mRNA or protein. Expression of OCT (or NET) can be examined in whole cell or tissue samples. In terms of early diagnosis, treatment decisions, and prognosis, needle, surgical, or bone marrow biopsies can be used and examined by techniques such as immunoblotting or immunohistochemistry and compared to control cells or tissue, e.g., from a healthy subject. In addition, microlaser microdissection can be used to isolate a few cells and run RT-PCR for OCT (or NET) nucleic acid. The following PCR primers can be used to detect OCT1 nucleic acid: (sense, SEQ ID NO:9) 5'-CTG TGT AGA CCC CCT GGC TA-3'; and (antisense, SEQ ID NO:10) 5'-GTG TAG CCA GCC ATC CAG TT-3'. The following PCR primers can be used to detect OCT2 nucleic acid: (sense, SEQ ID NO:11) 5'-CCT GGT ATG TGC CAA CTC CT-3'; and (antisense, SEQ ID NO:12) 5'-CAC CAG GAG CCC AAC TGT AT-3'. The following PCR primers can be used to detect OCT3 nucleic acid: (sense, SEQ ID NO:13) 5'-ATC GTC AGC GAG TTT GAC CT-3'; and (antisense, SEQ ID NO:14) 5'-TTG AAT CAC GAT TCC CAC AA-3'.

In determining the levels of protein expression or the localization of OCT (or NET) protein, polyclonal or monoclonal antibodies that specifically bind to OCT1, OCT2, or OCT3 (or NET) can be used.

In some embodiments, the methods of the present invention are useful in providing a prognosis for platinum-based compound (as described herein) therapy for a colorectal cancer or a subtype thereof, e.g., colorectal adenocarcinoma (i.e., mucinous, signet ring cell), colorectal sarcoma, colorectal melanoma, colorectal carcinoid, or colorectal lymphoma. The methods of the present invention are also useful in providing a prognosis for platinum-based compound (as described herein) therapy for liver cancer or a subtype thereof, e.g., fibrolamellar hepatocarcinoma, cholangiocarcinoma, angiosarcoma, hemangiosarcoma, or hepatoblastoma. In one embodiment, the methods of the present invention are used in providing a prognosis for platinum-based compound (as described herein) therapy for a neuroendocrine cancer. In one embodiment, the methods of the present invention are used in providing a prognosis for platinum-based compound (as described herein) therapy for a brain cancer, or a subtype thereof, e.g., glioblastoma multiforme, neuroblastoma, glioma, neuroendocrine cancer. In carrying out the prognostic methods described herein, the determination of whether or not OCT (or NET) protein or nucleic acid is expressed can be made, e.g., by comparing a test sample to a control autologous sample from normal tissue.

In some embodiments of the prognostic methods of the present invention, the sample can be taken from a tissue of a primary tumor or a metastatic tumor. A tissue sample can be taken, for example, by an excisional biopsy, an incisional biopsy, a needle biopsy, a surgical biopsy, a bone marrow biopsy, or any other biopsy technique known in the art. In some embodiments, the tissue sample is microlaser microdissected cells from a needle biopsy. In other embodiments, the tissue sample is a metastatic cancer tissue sample. In yet other embodiments, the tissue sample is fixed, e.g., with paraformaldehyde, and embedded, e.g., in paraffin. Suitable tissue samples can be obtained from colon, rectum, liver, kidney, bladder, prostate, ovary, lung, breast, brain, etc., as well as from the blood, serum, saliva, urine, bone, lymph node, or other tissue.

In some embodiments, the diagnostic or prognostic methods of the present invention further comprise genotyping the subject to determine an OCT (or NET) genotype, i.e., determining the presence or absence of a variant allele at a polymorphic site in the OCT1, OCT2, and/or OCT3 (or NET) gene. In one embodiment, the OCT genotype is selected from the group consisting of: wild-type OCT (OCT1, OCT2, and/or OCT3), G401S, 420del, S14F, R61C, G220V, V408M, and G465R. In one embodiment, presence of the wild-type or V408M variant predicts a better response to platinum-based compound, as described herein, therapy.

In some embodiments is a method of localizing a cancer that expresses an OCT (e.g., OCT1, OCT2, and/or OCT3) (or NET) in vivo, the method comprising the step of imaging in a subject a cell expressing the OCT (or NET) (e.g., protein and/or RNA), thereby localizing the cancer in vivo.

In some embodiments is a method of treating or inhibiting a cancer that expresses an OCT (e.g., OCT1, OCT2, and/or OCT3) or NET, the method comprising the step of administering to a subject in need thereof a therapeutically effective amount of a platinum-based compound or drug as described herein.

In some embodiments are methods of diagnosing or providing a prognosis for a cancer therapy, e.g., therapy for a cancer that expresses at least one OCT (or NET) marker (e.g., OCT1, OCT2 and/or OCT3) such as colorectal cancer or liver cancer or brain cancer or neuroendocrine cancer. As used herein, the term "providing a prognosis" refers to providing a prediction of the probable course, recommended therapy, and outcome of a cancer or the likelihood of recovery from the cancer.

In some embodiments, cancer patients with positive or high OCT (or NET) expression have a longer disease-specific survival as compared to those with negative or low expression. As such, the level of OCT (or NET) expression can be used as a prognostic indicator, with positive or high expression as an indication of a good prognosis, e.g., a longer disease-specific survival.

In some embodiments, the methods of the present invention can also be useful for diagnosing the severity of a cancer, e.g., a cancer that expresses at least one OCT (or NET) marker. As a non-limiting example, the level of OCT (or NET) expression can be used to determine the stage or grade of a cancer such as colorectal cancer, e.g., according to the Tumor/Nodes/Metastases (TNM) system of classification (International Union Against Cancer, 6th edition, 2002), the Dukes staging system (Dukes, *J. Pathol.*, 35:323 (1932)), or the Astler-Coller staging system (Astler et al., *Ann. Surg.*, 139:846 (1954)). Typically, cancers are staged using a combination of physical examination, blood tests, and medical imaging. If tumor tissue is obtained via biopsy or surgery, examination of the tissue under a microscope can also provide pathologic staging. In some embodiments, cancer patients with positive or high OCT (or NET) expression may have a more severe stage or grade of that type of cancer. As such, the level of OCT (or NET) expression can be used as a diagnostic indicator of the severity of a cancer or of the risk of developing a more severe stage or grade of the cancer. In certain other instances, the stage or grade of a cancer assists a practitioner in determining the prognosis for the cancer and in selecting the appropriate cancer therapy.

Diagnosis or prognosis can involve determining the level of OCT (or NET) expression (i.e., transcription or translation) in a patient and then comparing the level or localization to a baseline or range. In some embodiments, the baseline value is representative of OCT (or NET) expression levels in a healthy person not suffering from the disease (e.g. cancer). Variation of levels of a polypeptide or polynucleotide of the present invention from the baseline range (i.e., either up or down) may indicate that the patient has a cancer or is at risk of developing a cancer. Variation of levels of a polypeptide or polynucleotide of the present invention from the baseline range (i.e., either up or down) may indicate that the patient has a cancer that would respond to platinum-based compound therapy or would not respond to platinum-based compound therapy. In some embodiments, the level of OCT (or NET) expression is measured by taking a blood, urine, or tissue sample from a patient and measuring the amount of a polypeptide or polynucleotide of the present invention in the sample using any number of detection methods, such as those discussed herein. In some embodiments, the presence of OCT (or NET) expression in a sample is indicative that the patient should receive platinum-based compound treatment, as described herein. In some embodiments, an increased level of OCT (or NET) expression in a sample, compared to a control, is indicative that the patient should receive platinum-based compound treatment, as described herein.

Any antibody-based technique for determining a level of expression of a protein of interest can be used to measure the level of OCT or NET expression in tumor tissue or cancerous cells (e.g. ELISA assays, immunoprecipitation assays, and immunohistochemical assays). One skilled in the art will know of additional antibody-based techniques that can be used for determining a level of OCT (or NET) expression. PCR assays can be used to detect expression levels of nucleic acids, as well as to discriminate between variants in genomic structure, such as insertion/deletion mutations, truncations, or splice variants.

In some embodiments, the expression of at least one OCT (or NET) marker in a cancerous or potentially cancerous tissue may be evaluated by visualizing the presence and/or localization of the OCT (or NET) marker in the subject. The visualization of cancerous or potentially cancerous tissue in live subjects can be performed using anti-OCT (OCT1, OCT2, and/or OCT3) or anti-NET antibodies or other molecules that specifically interacts or binds to an OCT (or NET) transcript or to a polypeptide encoded by the transcript.

A detectable moiety can be coupled either directly or indirectly to anti-OCT antibodies (or anti-NET antibodies) using methods well known in the art (e.g. radionuclides, fluorescent dyes (e.g., fluorescein, fluorescein isothiocyanate (FITC), Oregon Green™, rhodamine, Texas red, tetrarhodimine isothiocynate (TRITC), Cy3, Cy5, etc.), fluorescent markers (e.g., green fluorescent protein (GFP), phycoerythrin, etc.), autoquenched fluorescent compounds that are activated by tumor-associated proteases, enzymes (e.g., luciferase, horseradish peroxidase, alkaline phosphatase, etc.), nanoparticles, biotin, digoxigenin).

In some embodiments, a composition or method of detection may be used to visualize live subjects using any device or method known in the art (e.g. Single Photon Emission Computerized Tomography (SPECT), radionuclide scintigraphy, Positron Emission Tomography (PET), a laparoscopic probe (see U.S. Pat. No. 5,429,133), Magnetic Resonance Imaging (MRI), radiography (i.e., X-rays), computed tomography (CT), fluoroscopy, or other methods known in the art).

In some embodiments in vivo optical imaging techniques may be suitable for the visualization of fluorescent and/or enzymatic labels or markers (e.g. fluorescence microendoscopy (see, e.g., Flusberg et al., *Optics Lett.*, 30:2272-2274 (2005)), fiber-optic fluorescence imaging (see, e.g., Flusberg et al., *Nature Methods*, 2:941-950 (2005)), fluorescence imaging using a flying-spot scanner (see, e.g., Ramanujam et al., *IEEE Trans. Biomed. Eng.*, 48:1034-1041 (2001)), catheter-based imaging systems (see, e.g., Funovics et al., *Radiology*, 231:659-666 (2004)), near-infrared imaging systems (see, e.g., Mahmood et al., *Radiology*, 213:866-870 (1999)), fluorescence molecular tomography (see, e.g., Gurfinkel et al., *Dis. Markers*, 19:107-121 (2004)), and bioluminescent imaging (see, e.g., Dikmen et al., *Turk. J. Med. Sci.*, 35:65-70 (2005))).

Anti-OCT antibodies (or anti-NET antibodies), when conjugated to any of the above-described detectable moieties, can be administered in doses effective to achieve the desired image of tumor tissue or cancerous cells in a subject. Such detection is aimed at determining where one or more OCT (or NET) markers are concentrated in a subject, with such concentration being an indicator of the location of a tumor or tumor cells. Alternatively, such detection is aimed at determining the extent of tumor regression in a subject, with the size of the tumor being an indicator of the efficacy of cancer therapy.

Diagnosis or prognosis can further involve determining the genotype of at least one OCT marker (or NET marker) in a subject. For example, genotyping an OCT (or NET) nucleic acid marker at a polymorphic site for alleles that result in decreased or increased organic cation transporter activity can be useful in diagnosing or providing a prognosis for cancers that express the OCT (or NET) marker. In certain instances, an OCT (or NET) nucleic acid marker that comprises a variant allele resulting in no or substantially reduced substrate transporter activity is indicative of a cancer that does not express the OCT (or NET) marker. A subject having this genotype would have a cancer that may be resistant to platinum-based compound or drug therapy and may have a poor prognosis for cancer using such therapy. Variant alleles in OCT1 and OCT2 which comprise polymorphisms suitable for detecting in the methods of the present invention are described in, e.g., Shu et al., *Proc. Natl. Acad. Sci. U.S.A.*, 100:5902-5907 (2003); and Leabman et al., *Pharmacogenetics*, 12:395-405 (2002).

In some embodiments the methods of the present invention include determining whether or not OCT (or NET) protein or nucleic acid (e.g., mRNA) is expressed in a sample. As used herein, the term "determining whether or not OCT (or NET) protein (or nucleic acid) is expressed" refers to determining the presence or level of at least one OCT (or NET) marker of interest (e.g., OCT1, OCT2, and/or OCT3 or NET) by using any quantitative or qualitative assay known to one of skill in the art. In some embodiments of the methods described herein, prognostic or diagnostic methods as described above are combined with the methods of using the compounds described herein (e.g. formula I, Ia, II, IIa, III, IIIa, IV, or V, including embodiments).

In some embodiments, an OCT (or NET) protein marker is analyzed using an immunoassay, although other methods are well known to those skilled in the art (e.g., the measurement of marker RNA levels). Immunoassay techniques and protocols are generally described in Price and Newman, "Principles and Practice of Immunoassay," 2nd Edition, Grove's Dictionaries, 1997; and Gosling, "Immunoassays: A Practical Approach," Oxford University Press, 2000. The presence or amount of an OCT (or NET) protein marker is generally determined using antibodies specific for the marker and detecting specific binding. For example, polyclonal antibodies directed to OCT1, OCT2, or OCT3 can be obtained from Alpha Diagnostics Intl. Inc. (San Antonio, Tex.).

Any suitable immunoassay can be utilized for determining whether or not OCT (or NET) protein is expressed in a sample (e.g. enzyme immunoassays (EIA) such as enzyme multiplied immunoassay technique (EMIT), enzyme-linked immunosorbent assay (ELISA), IgM antibody capture ELISA (MAC ELISA), and microparticle enzyme immunoassay (MEIA); capillary electrophoresis immunoassays (CEIA); radioimmunoassays (RIA); immunoradiometric assays (IRMA); fluorescence polarization immunoassays (FPIA); and chemiluminescence assays (CL)). If desired, such immunoassays can be automated. Immunoassays can also be used in conjunction with laser induced fluorescence (see, e.g., Schmalzing et al., *Electrophoresis*, 18:2184-93 (1997); Bao, *J. Chromatogr. B. Biomed. Sci.*, 699:463-80 (1997)). Liposome immunoassays, such as flow-injection liposome immunoassays and liposome immunosensors, (see, e.g., Rongen et al., *J. Immunol. Methods*, 204:105-133 (1997)) or nephelometry assays may be used in the methods of detecting the presence of a marker as described herein.

Specific immunological binding of the antibody to OCT (or NET) protein can be detected directly or indirectly (e.g. direct detection may include fluorescent or luminescent tags, metals, dyes, radionuclides). An antibody labeled with iodine-125 ($^{125}$I) can be used for determining whether or not OCT (or NET) protein is expressed in a sample. A chemiluminescence assay using a chemiluminescent antibody specific for an OCT (or NET) protein marker is suitable for sensitive, non-radioactive detection of OCT (or NET) protein levels. An antibody labeled with fluorochrome is also suitable for determining whether or not OCT (or NET) protein is expressed in a sample (e.g. DAPI, fluorescein, Hoechst 33258, R-phycocyanin, B-phycoerythrin, R-phycoerythrin, rhodamine, Texas red, and lissamine). Indirect labels include various enzymes well known in the art, such as horseradish peroxidase (HRP), alkaline phosphatase (AP), β-galactosidase, urease, and the like. A horseradish-peroxidase detection system can be used, for example, with the chromogenic substrate tetramethylbenzidine (TMB), which yields a soluble product in the presence of hydrogen peroxide that is detectable at 450 nm. An alkaline phosphatase detection system can be used with the chromogenic substrate p-nitrophenyl phosphate, for example, which yields a soluble product readily detectable at 405 nm. Similarly, a β-galactosidase detection system can be used with the chromogenic substrate o-nitrophenyl-β-D-galactopyranoside (ONPG), which yields a soluble product detectable at 410 nm. An urease detection system can be used with a substrate such as urea-bromocresol purple (Sigma Immunochemicals; St. Louis, Mo.). A signal from the label can be analyzed, for example, using a spectrophotometer to detect color from a chromogenic substrate; a radiation counter to detect radiation such as a gamma counter for detection of $^{125}$I; or a fluorometer to detect fluorescence in the presence of light of a certain wavelength.

Antigen capture assays can be useful in the methods of the present invention. For example, in an antigen capture assay, an antibody directed to an OCT (or NET) protein marker is bound to a solid phase and sample is added such that OCT (or NET) protein is bound by the antibody. After unbound proteins are removed by washing, the amount of bound marker can be quantitated using, for example, a radioimmunoassay (see, e.g., Harlow and Lane, Antibodies: A Laboratory Manual, Cold Spring Harbor Laboratory, New York, 1988)). Sandwich enzyme immunoassays can also be useful in the methods of the present invention. For example, in a two-antibody sandwich assay, a first antibody is bound to a solid support, and OCT (or NET) protein is allowed to bind to the first antibody. The amount of OCT (or NET) protein is quantitated by measuring the amount of a second antibody that binds the marker. The antibodies can be immobilized onto a variety of solid supports, such as magnetic or chromatographic matrix particles, the surface of an assay plate (e.g., microtiter wells), pieces of a solid substrate material or membrane (e.g., plastic, nylon, paper), and the like. An assay strip can be prepared by coating the antibody or a plurality of antibodies in an array on a solid support. This strip can then be dipped into the test sample and processed quickly through washes and detection steps to generate a measurable signal, such as a colored spot.

Quantitative western blotting can also be used to detect or determine whether or not OCT (or NET) protein is expressed in a sample. Western blots can be quantitated by well known methods such as scanning densitometry or phosphorimaging.

Alternatively, a variety of immunohistochemistry (IHC) techniques can be used to determine whether or not OCT (or NET) protein is expressed in a sample. As used herein, the term "immunohistochemistry" or "IHC" encompasses techniques that utilize the visual detection of fluorescent dyes or enzymes coupled (i.e., conjugated) to antibodies that react with the OCT (or NET) protein marker using fluorescent microscopy or light microscopy (e.g. direct fluorescent antibody, indirect fluorescent antibody (IFA), anticomplement immunofluorescence, avidin-biotin immunofluorescence, and immunoperoxidase assays).

The presence or level of an OCT (or NET) protein marker can also be determined by detecting or quantifying the amount of the purified marker. Purification of OCT (or NET) protein can be achieved, for example, by high pressure liquid chromatography (HPLC), alone or in combination with mass spectrometry (e.g., MALDI/MS, MALDI-TOF/MS, tandem MS, etc.). Qualitative or quantitative detection of OCT (or NET) protein can also be determined by well-known methods including, without limitation, Bradford assays, Coomassie blue staining, silver staining, assays for radiolabeled protein, and mass spectrometry.

The analysis of a plurality of OCT (or NET) protein markers may be carried out separately or simultaneously with one test sample. For separate or sequential assay of OCT (or NET) protein markers, suitable apparatuses include clinical laboratory analyzers such as the ElecSys (Roche), the AxSym (Abbott), the Access (Beckman), the ADVIA®, the CENTAUR® (Bayer), and the NICHOLS ADVANTAGE® (Nichols Institute) immunoassay systems. Preferred apparatuses or protein chips perform simultaneous assays of a plurality of OCT (or NET) protein markers on a single surface. Particularly useful physical formats comprise surfaces having a plurality of discrete, addressable locations for the detection of a plurality of different biomarkers. Such formats include protein microarrays, or "protein chips" (see, e.g., Ng et al., *J. Cell Mol. Med.*, 6:329-340 (2002)) and certain capillary devices (see, e.g., U.S. Pat. No. 6,019,944). In these embodiments, each discrete surface location may comprise antibodies to immobilize one or more OCT (or NET) protein markers for detection at each location. Surfaces may alternatively comprise one or more discrete particles (e.g., microparticles or nanoparticles) immobilized at discrete locations of a surface, where the microparticles comprise antibodies to immobilize one or more OCT (or NET) protein markers for detection.

In addition to the above-described assays for determining whether or not OCT (or NET) protein is expressed in a sample, analysis of OCT (or NET) marker mRNA levels using routine techniques such as Northern analysis, reverse-transcriptase polymerase chain reaction (RT-PCR), or any other methods based on hybridization to a nucleic acid sequence that is complementary to a portion of the marker coding sequence (e.g., slot blot hybridization) are also within the scope of the present invention. The mRNA expression of a gene of interest is typically evaluated in vitro on a sample collected from the subject in comparison to a normal or reference sample. Applicable PCR amplification techniques are described in, e.g., Ausubel et al., Theophilus et al., and Innis et al., supra. General nucleic acid hybridization methods are described in Anderson, "Nucleic Acid Hybridization," BIOS Scientific Publishers, 1999. Amplification or hybridization of a plurality of transcribed nucleic acid sequences (e.g., mRNA or cDNA) can also be performed from mRNA or cDNA sequences arranged in a microarray. Microarray methods are generally described in Hardiman, "Microarrays Methods and Applications: Nuts & Bolts," DNA Press, 2003; and Baldi et al., "DNA Microarrays and Gene Expression: From Experiments to Data Analysis and Modeling," Cambridge University Press, 2002.

Analysis of the genotype of an OCT (or NET) nucleic acid marker can be performed using techniques known in the art including, without limitation, polymerase chain reaction (PCR)-based analysis, sequence analysis, and electrophoretic analysis. A non-limiting example of a PCR-based analysis includes a Taqman® allelic discrimination assay available from Applied Biosystems. Non-limiting examples of sequence analysis include Maxam-Gilbert sequencing, Sanger sequencing, capillary array DNA sequencing, thermal cycle sequencing (Sears et al., *Biotechniques*, 13:626-633 (1992)), solid-phase sequencing (Zimmerman et al., *Methods Mol. Cell. Biol.*, 3:39-42 (1992)), sequencing with mass spectrometry such as matrix-assisted laser desorption/ionization time-of-flight mass spectrometry (MALDI-TOF/MS; Fu et al., *Nature Biotech.*, 16:381-384 (1998)), and sequencing by hybridization (Chee et al., *Science*, 274:610-614 (1996); Drmanac et al., *Science*, 260:1649-1652 (1993); Drmanac et al., *Nature Biotech.*, 16:54-58 (1998)). Non-limiting examples of electrophoretic analysis include slab gel electrophoresis such as agarose or polyacrylamide gel electrophoresis, capillary electrophoresis, and denaturing gradient gel electrophoresis. Other methods for genotyping a subject at a polymorphic site in an OCT (or NET) nucleic acid marker include, e.g., the INVADER® assay from Third Wave Technologies, Inc., restriction fragment length polymorphism (RFLP) analysis, allele-specific oligonucleotide hybridization, a heteroduplex mobility assay, and single strand conformational polymorphism (SSCP) analysis.

Analysis of whether or not an OCT (or NET) nucleic acid has been gene amplified or deleted in a sample can also be used in the pharmacogenetic, diagnostic and prognostic methods described herein. In some embodiments, the presence or level of gene amplification or deletion of one or more OCT (or NET) nucleic acid markers can be determined by DNA-based techniques such as PCR or Southern blot analysis or by molecular cytogenetic techniques such as fluorescence in situ hybridization (FISH), chromogenic in situ hybridization (CISH), and immunohistochemistry. Other techniques include genome-wide scanning of amplified chromosomal regions with comparative genomic hybridization for the detection of amplified regions in tumor DNA (see, e.g., Kallioniemi et al., Science, 258:818-821 (1992)) and the detection of gene amplification by genomic hybridization to cDNA microarrays (see, e.g., Heiskanen et al., Cancer Res., 60:799-802 (2000)). One skilled in the art will know of additional gene amplification or deletion techniques that can be used to detect or determine a level of an amplified gene that corresponds to one or more OCT (or NET) nucleic acid markers of the present invention.

In another embodiment, the present invention provides kits for carrying out the therapeutic, diagnostic, and prognostic assays described herein. The kits typically include one or more probes that comprise an antibody or nucleic acid sequence that specifically binds to the polypeptides or polynucleotides of the present invention, and a label for detecting the presence of the probe. The kits can find use, for example, for measuring the levels of OCT (or NET) protein or OCT (or NET) transcripts, or for measuring OCT (or NET) activity to a target substrate. The kits may also include several polynucleotide sequences encoding polypeptides of the present invention. In some embodiments of the methods described herein, prognostic or diagnostic methods as described above may be combined with the methods of using the compounds described herein (e.g. formula I, Ia, II, IIa, III, IIIa, IV, or V, including embodiments).

In some embodiments is a method of providing a prognosis for platinum-based compound cancer therapy in a subject, the method including the steps of (a) contacting a sample from the subject with an antibody that specifically binds to OCT (or NET) protein; and (b) determining whether or not OCT (or NET) protein is expressed in the sample, thereby providing a prognosis for platinum-based compound cancer therapy. In some embodiments, the cancer is selected from the group consisting of colorectal cancer, liver cancer, prostate cancer, renal cancer, bladder cancer, ovarian cancer, breast cancer, lung cancer, leukemia, non-Hodgkin's lymphoma, and multiple myeloma. In some embodiments, the cancer is selected from the group consisting of brain cancer, glioblastoma multiforme, glioma, neuroblastoma, and neuroendocrine cancer. In some embodiments, the OCT is selected from the group consisting of OCT1, OCT2, OCT3, and combinations thereof. In some embodiments, the method includes genotyping the subject to determine an OCT (or NET) genotype. In some embodiments of the methods described herein, prognostic or diagnostic methods as described above may be combined with the methods of using the compounds described herein (e.g. formula I, Ia, II, IIa, III, IIIa, IV, or V, including embodiments).

In some embodiments is a method of providing a prognosis for platinum-based compound cancer therapy in a subject, the method including the steps of (a) contacting a sample from the subject with a primer set of a first oligonucleotide and a second oligonucleotide that each specifically hybridize to an OCT (or NET) nucleic acid; (b) amplifying the OCT (or NET) nucleic acid in the sample; and (c) determining whether or not the OCT (or NET) nucleic acid in the sample is expressed in the sample, thereby providing a prognosis for platinum-based compound cancer therapy. In some embodiments, the cancer is selected from the group consisting of colorectal cancer, liver cancer, prostate cancer, renal cancer, bladder cancer, ovarian cancer, breast cancer, lung cancer, leukemia, non-Hodgkin's lymphoma, and multiple myeloma. In some embodiments, the cancer is selected from the group consisting of brain cancer, glioblastoma multiforme, glioma, neuroblastoma, and neuroendocrine cancer. In some embodiments is a method of localizing a cancer that expresses an organic cation transporter (OCT) or NET in vivo, the method comprising the step of imaging in a subject a cell expressing OCT or NET, thereby localizing the cancer in vivo. In some embodiments of the methods described herein, prognostic or diagnostic methods as described above are combined with the methods of using the compounds described herein (e.g. formula I, Ia, II, IIa, III, IIIa, IV, or V, including embodiments).

In some embodiments, a method is presented for detecting an OCT (or a NET) protein or mRNA in a cell from a patient. In some embodiments, the method further includes administering to the patient a platinum-based compound described herein. In some embodiments, the cell from the patient expresses an OCT (or NET) protein. In some embodiments, the cell from the patient has an increased amount of an OCT or NET mRNA or protein compared to the amount of an OCT or NET mRNA or protein in a control sample.

In some embodiments, a method is presented for administering a platinum-based compound as described herein to a patient with cancer cells that have an increased amount of an OCT or NET mRNA or protein compared to a control sample.

Examples

A. Experimental Overview

Members of the solute carrier (SLC) 22A family, OCT1 (SLC22A1) and OCT2 (SLC22A2) mediate the intracellular uptake of structurally diverse organic cations that includes endogenous cations such as choline, creatinine and a variety of xenobiotics such as tetraethylammonium (TEA, a prototypic organic cation), the neurotoxin MPP+ (1-methyl-4-pyridinium). It is quite likely that these transporters are expressed by neoplastic liver cells. Any increase in the affinity of oxaliplatin-like or other platinum complex towards OCTs holds the promise of delivering a therapeutic agent that possesses a far greater efficacy and specificity for any cancer that retains a high level of OCT expression than the agents currently used.

Several mechanistic investigations have established the monoaquated complex of compounds such as oxaliplatin to be the form that is transporter by the OCTs. This complex has a net one positive charge (FIG. 1). Such complexes are highly unstable in nature due to their tremendous susceptibility toward the displacement of the water molecule by a chloride ion, forming a neutral dichloro compound. Chemical mimics of the monoaqua complex, that have similar stereoelectronic properties may possess the ability to be recognized by OCTs as substrates. In effect, this implies a chemically stable entity whose activity is channeled towards an OCT-expressing tumor.

Described herein are examples of platinum complexes of various types:

Examples of a type of platinum complex are listed in Table 1.

TABLE 1

Cytotoxicity of class A platinum complexes in cells stably transfected with human OCTs (ND = not determined)

| Compound Structure | IC$_{50}$ HEK-MOCK (μM) | IC$_{50}$ HEK-hOCT1 (μM) | IC$_{50}$ HEK-hOCT2 (μM) |
|---|---|---|---|
| 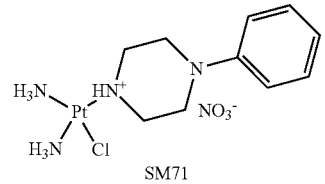 SM71 | 49.96 ± 2.030 | 0.745 ± 0.003 | 1.258 ± 0.319 |

Examples of another type of platinum complex are listed in Table 2. The dichlorides on the leaving group side may be intact and may form bidentate chelates with DNA, possibly similar to those formed by oxaliplatin.

TABLE 2

Cytotoxicity of class B platinum complexes in cells stably transfected with human OCTs

| Compound Structure | IC$_{50}$ HEK-MOCK (μM) | IC$_{50}$ HEK-hOCT1 (μM) | IC$_{50}$ HEK-hOCT2 (μM) |
|---|---|---|---|
| 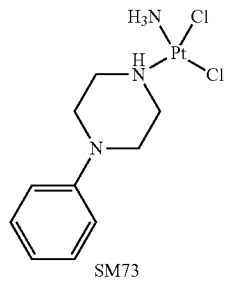 SM73 | 12.35 ± 0.759 | 0.036 ± 0.004 | 0.005 ± 0.001 |
| 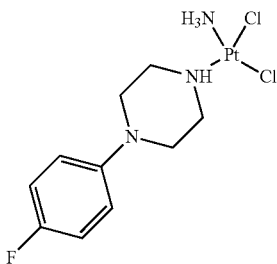 SM85 | 8.100 ± 1.256 | 0.071 ± 0.014 | 0.208 ± 0.035 |

Examples of another type of platinum complex are listed in Table 3 which comprises trans-platinum complexes that may form bi- or monodentate complexes with DNA.

TABLE 3

Cytotoxicity of class C platinum complexes in cells stably transfected with human OCTs

| Compound Structure | IC$_{50}$ HEK-MOCK (μM) | IC$_{50}$ HEK-hOCT1 (μM) | IC$_{50}$ HEK-hOCT2 (μM) |
| --- | --- | --- | --- |
| 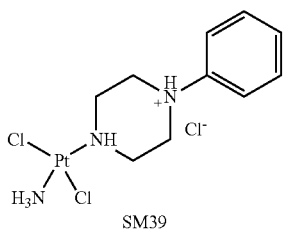 SM39 | 11.983 | 7.513 | 12.88 |
| 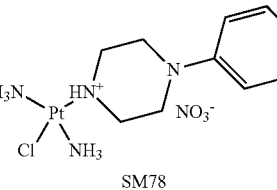 SM78 | 134.4 ± 19.18 | 0.988 ± 0.030 | 2.351 ± 0.313 |

Evaluation of compounds was carried out in an in-vitro cytotoxicity assay, involving a comparison between the effect of the platinum complex on human embryonic kidney cells (HEK293) transfected with human OCT1 (HEK-hOCT1) and OCT2 (HEK-hOCT2) versus those that are not transfected. The results indicated that the positively charged complexes are much better substrates for OCT1 and OCT2 than oxaliplatin itself. The IC$_{50}$ values of these new synthesized complexes were 20-170 times lower in OCT transfected cell lines when compared with untransfected cells. Cytotoxicities of individual platinum complexes are listed in table 1, 2 and 3.

The increased cytotoxicity of the compounds described herein was determined in HEK-hOCT1 cells when compared to untransfected cells and suggests an increased cellular uptake and accumulation.

Evidence for the higher accumulation of platinum-based compounds described herein was obtained through a comparison of the cellular uptake of select compounds vs. oxaliplatin in OCT1 transfected and untransfected cells. A higher accumulation of compounds, when compared to the accumulation of oxaliplatin in HEK-OCT1 cells, both in comparison to untransfected cells serves to confirm that platinum-based compounds described herein have an increased cellular uptake in OCT expressing cells. Similar results were obtained when platinum-DNA adducts concentration was quantitated in HEK-OCT1 and HEK-MOCK cells. These experiments clearly demonstrated that platinum-based compounds could be used as targeted anticancer therapy.

Similar results were obtained for the series of our synthetic platinum complexes (tables 1, 2 and 3). Also, certain complexes were found to be substrates for OCT2 (tables 1, 2 and 3) and OCT3 (table 4). This greatly substantiates our original proposition of the stereoelectronic mimicry of the bioactive mono-aqua complex to achieve higher affinity for OCTs.

TABLE 4

| Platinum-based compound in HEK cells expressing NET or controls. | | | |
| --- | --- | --- | --- |
| Platinum Compound | HEK-EV IC50 (IIM) | HEK-hNET IC50 (LIM) | Resistance Factor |
| Cisplatin | 2.56 ± 0.38 | 1.38 ± 0.17 | 1.8 |
| Oxaliplattn | 2.71 1 0.43 | 1.55 ± 0.21 | 1.7 |
| SM73 | 5.84 ± 0.11 | 1.07 ± 0.49 | 5.5 |
| SM85 | 9.65 ± 2.61 | 2.32 ± 22.5 | 4.1 |

Our preliminary in vivo toxicity experiments in nude mice have indeed lended support for our rational design of targeted platinum complexes.

Based on our in-vitro findings that positively charged synthetic platinum complexes are very good substrates of OCTs, a complete in-vivo efficacy evaluation of lead compounds is being carried out in transgenic and xenograft mouse models for cancer. Further, the efficacy of these complexes is being tested in cancer cell lines expressing OCTs. Based on the pharmacokinetic properties of these lead complexes, further structural optimization is being carried out to develop platinum compounds with enhanced specificity for OCTs. We are developing platinum anticancer compounds that are excellent substrates of OCTs for the purpose of targeted therapy of cancers with high level expression of human OCTs. This approach can enhance the therapeutic efficacy and reduce systemic toxicity of the platinum-based anticancer drugs due to the enrichment of platinum compounds in cells with high level of OCT expression. Oxaliplatin and its synthetic platinum analogs can be used for the treatment of the cancers expressing relatively high levels of OCTs, since they are expected to be enriched in the liver tumor cells due to the high level of OCT expression.

This study provides a pharmacogenomic basis for the selection of patients based on the expression level of a particular transporter for treatment with these novel anticancer agents and moving towards individualized therapy. A net increase in the therapeutic efficacy and decrease of systemic toxicity is a desired characteristic of these anticancer compounds.

Targeting OCTs enhances the delivery of platinum compounds to OCT expressing tumors and hence decreases the toxicity to cells which do not express OCTs. Currently synthezied platinum analogs of oxaliplatin will, for the first time, bring into practice the currently hypothetical individualized treatment for cancer, since the expression level and/or polymorphism of these transporters will dictate the response and/or adverse reactions of their treatment.

Utilization of either the siRNA approach and/or the use of an inhibitor of hOCTs for diminishing the efficacy of the lead compounds is being used to confirm the utilization of OCTs to get inside cells by these compounds. We are performing in-vivo studies in transgenic and xenograft mouse models for cancers to produce a proof-of-concept. Further effect of individual OCT on pharmacokinetics and efficacy of new platinum complexes is being evaluated in specific OCT-knockout mice. Based on the efficacy, toxicity and PK/PD data for our lead compounds from our preliminary in vivo screen, we are rationally modifying/optimizing the structural features of these currently promising compounds.

Platinum-complexes are some of the most widely-used drugs for the treatment of cancers, especially solid tumors. Unfortunately, their tissue distribution is either nonspecific or of a specificity that is insufficient to cause adequate selective accumulation so as to deliver an adequate cytotoxic effect. We have found that the distribution of platinum complexes into various body tissues including tumors or neoplasms can be influenced through design of ligands that confer upon the platinum complex increased affinity for a particular influx transport mechanism. This enhanced affinity translates into higher sequestration of the platinum into tissues that express the particular influx transport mechanism. Higher tissue accumulation translates into 1) higher anticancer potency and 2) lower potential of adverse effects because the platinum is channeled away from the tissue where adverse effects occur.

In some embodiments, the platinum-based compound comprises one platinum ion in either the +2 or the +4 oxidation state. The nature of ligand attachment to the Pt ion may be an ionic bond or a dative/covalent-coordinate bond. In some embodiments, ionic bonds may be present bridging ligands or the Pt containing compound and a counterion without the involvement of the platinum ion in the said bridging unit.

Figure 5:
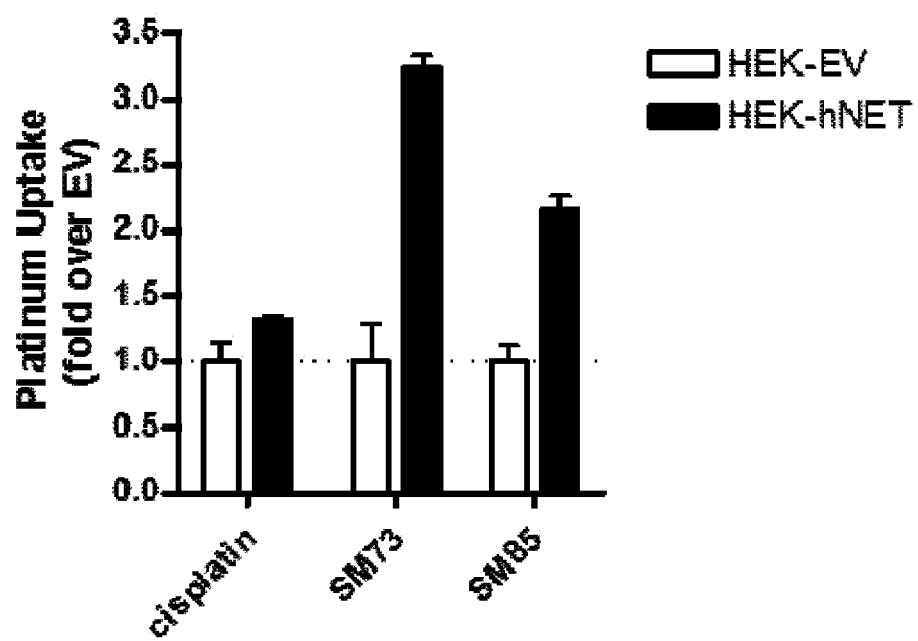
FIG. 5 shows the uptake of the platinum compounds, SM-73 and SM-85 into HEK cells that express NET vs. empty vector HEK cells.
Figure 6:
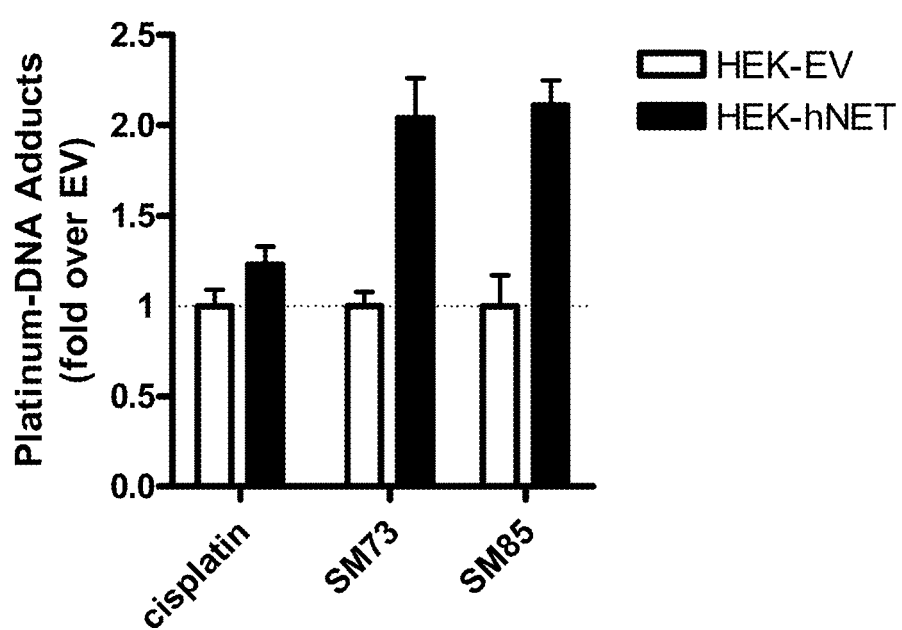
FIG. 6 shows the DNA-binding of the platinum agents in HEK cells.

We have synthesized a large (>100) library of platinum-based compounds. Described herein is the application these platinum-based compounds to the targeting of Norepinephrine Transporter (NET). A set platinum compounds are selected to exemplify this concept: SM-73 and SM-85 (FIG. 5).

Table 4 shows the toxicity of these compounds toward HEK cells that are either transfected stably with the Norepinephrine Transporter or are empty vector cells. The platinums in FIG. 5 bear ligands that confer upon them varying degrees of affinity for NET, which is translated into varying cytotoxicities that are dependent on the presence of absence of NET.

The term "resistance factor" is a measure of selectivity conferred upon the platinum-based compound by the inclusion of ligands that promote recognition by NET. From Table 4, it is clear that SM-73 is 5.5-fold more effective against HEK cells that express NET.

The success of our targeting strategy can be gauged in-vitro also through comparing the uptake of the platinum complex into cells. The actual effects of this increased uptake can in turn be ascertained and quantified through comparison of DNA-binding of the platinum complexes.

Overall, it is clear that the targeted platinum agents are more selective for accumulation into NET-expressing HEK cells when compared to the non-targeted platinum agent, cisplatin. Their individual selectivities vary and correspond well with their "resistance factor" values described previously; SM-73 is once again the most selective (3.25-fold) platinum agent.

Figure 7:
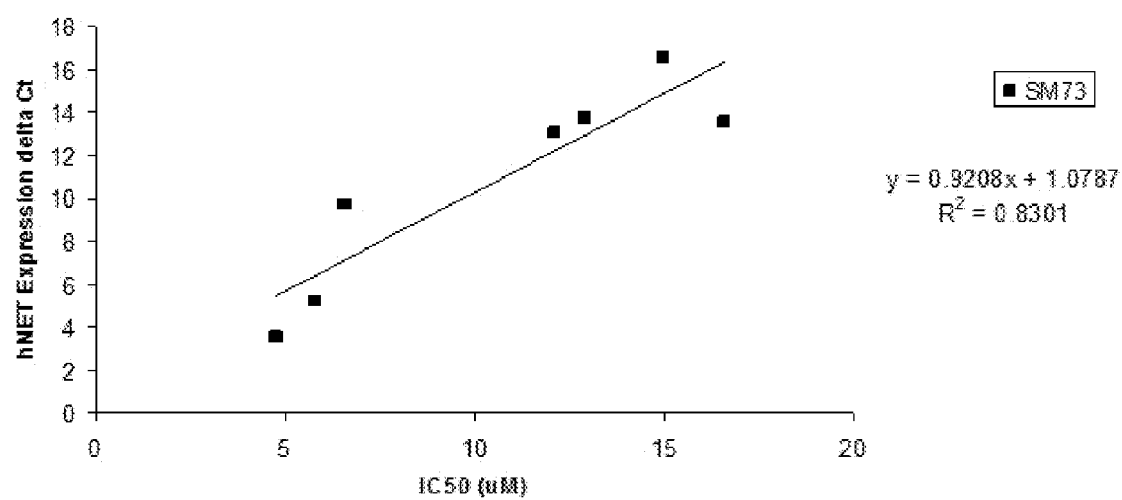
FIG. 7 shows a comparison of $IC_{50}$ values for select compounds with the degree of NET expression in the cell lines.
Figure 8:
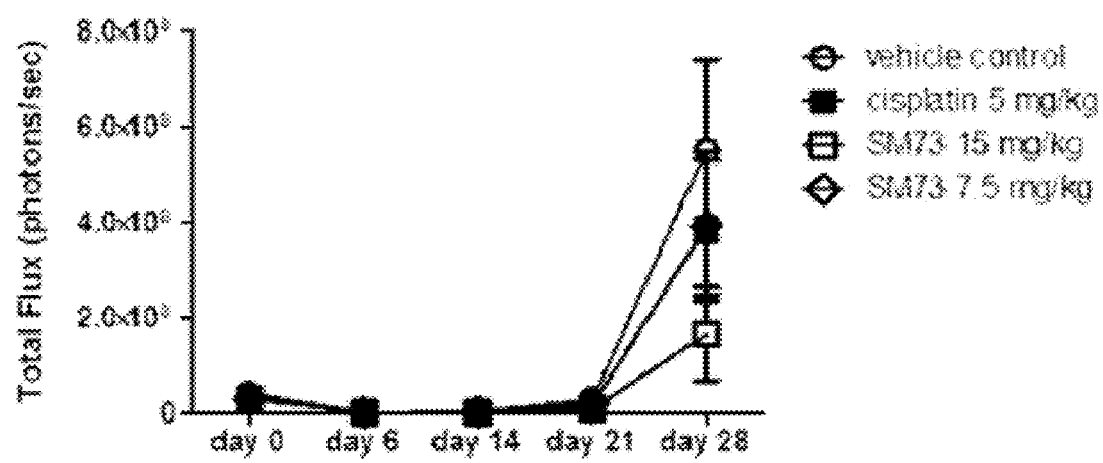
FIG. 8 shows that SM73 retains the antitumor efficacy of cisplatin to a significant extent against neuroblastoma xenografts in mice.
Figure 9:
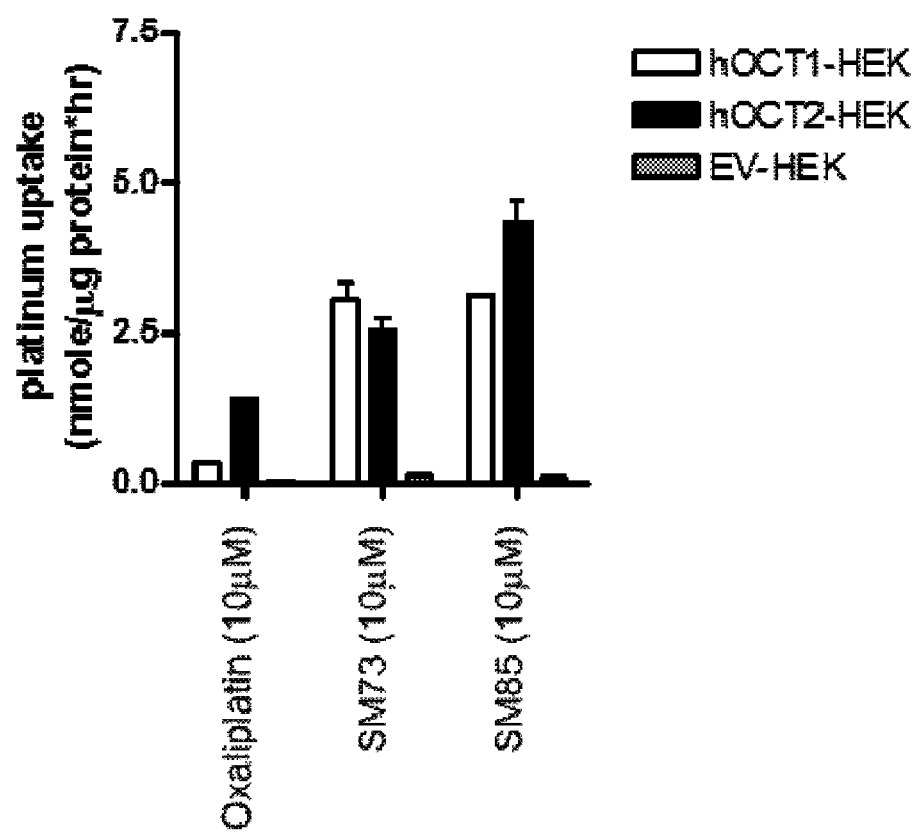
FIG. 9. Enhanced efficacy of synthetic platinum analogs hOCT1 expressing cell line compared to untransfected MOCK.
Figure 10:
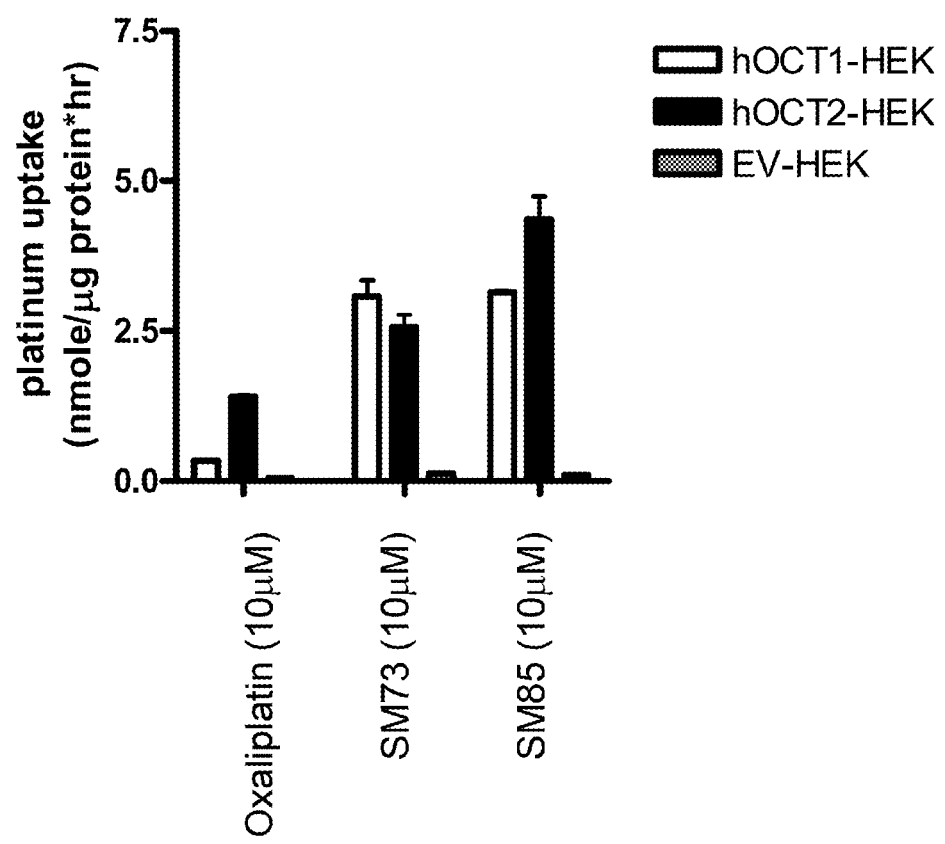
FIG. 10. Cellular accumulation rates of platinum after 2-hour exposure to oxaliplatin and lead platinum analogs.

FIG. 7 shows the DNA-binding of the platinum agents in HEK cells. The DNA-binding is also an example of a measure of the individual chemical reactivities of the platinum agents and thus does not reflect only the degree of targeting. The increased targeting in SM-73 and SM-85 has led to increased DNA-binding in spite of the inclusion of bulkier ligands when compared to cisplatin.

Compounds SM-73 and SM-85 are assayed against an array of neuroblastoma cell lines. Table 5 shows their toxicity against seven neuroblastoma cell lines.

TABLE 5

Platinum-based compounds in cell lines.

| Cell line | $IC_{50}$ (μM) | | | |
|---|---|---|---|---|
| | Cisplatin | SM73 | SM85 | Oxaliplatin |
| LANS | 6.156 | 5.235 | 8.156 | 15.93 |
| SHEP | 24.49 | 16.53 | 30.75 | 24.77 |
| SHSY5Y | 18.55 | 13.78 | 31.06 | 18.75 |
| Kelly | 19.88 | 13.06 | 33.11 | 20.41 |
| SKNSH | 3.769 | 3.583 | 8.427 | 15.54 |
| SKNMC | 9.629 | 13.55 | 18.90 | 19.91 |
| NB1691 | 12.41 | 9.722 | 9.898 | 29.4 |

SM-73 and SM-85 retain the efficacy of cisplatin against the seven neuroblastoma cell lines in spite of added steric bulk.

The efficacy of SM-73 may be related to the degree of NET expression in the seven tested cell lines. Cisplatin showed no such correlation. Increased efficacy arises from targeted cellular accumulation rather than nonspecific chemical reactivity.

The present studies demonstrate the advantage of using the newly synthesized platinum agent SM73 in vivo. SM-73 is being tested against neuroblastoma xenografts to ascertain retention of a significant degree of efficacy when compared to cisplatin. An evaluation is being conducted in various body tissues/plasma to determine toxicity.

Blood (CBC), Kidney and Liver-function tests of the mice treated with SM-73 in the present studies were similar to the vehicle treated control group, while the cisplatin treated group shows results indicative of some nephrotoxicity. The SM-73 treated mice group was also evaluated for ototoxicity. No ototoxicity was observed, in sharp contrast to the well-known clinically observed ototoxic effects of cisplatin.

We are currently evaluating similar newly synthesized platinum complexes targeted to influx transporters expressed by human cancer cells for development of invidualized cancer treatment.

B. Method Overview

Overview of Methods: An initial toxicity study is performed on oxaliplatin and two platinum analogs identified SM73 and SM85; to determine their maximum tolerated doses (MTDs) and pharmacokinetic profiles. The determined MTDs serves as a guideline for selecting the proper dose for studying the efficacy of these platinums. Stably transfected HEK293 cells with empty vector and OCT1 or OCT2 or OCT3 or NET are employed in this study. These cells lines are implanted subcutaneously in mice and the mice are subsequently treated with oxaliplatin, SM73 and SM85. Tumor growth rate and survival is monitored twice weekly for four weeks.

TABLE 8

Cytotoxicity of select Platinum complexes in cells stably transfected with human OCT3.

| Compound Number | Chemical Structure | IC$_{50}$ (μM) HEK-MOCK | IC$_{50}$ (μM) HEK-hOCT3 |
|---|---|---|---|
| Cisplatin | H$_3$N–Pt(Cl)$_2$–NH$_3$ | 2.624 | 4.838 |
| Carboplatin | (cyclobutanedicarboxylato) Pt(NH$_2$)$_2$ | 41.53 | 63.14 |
| Oxaliplatin | (1R,2R-DACH) Pt(oxalato) | 1.618 | 1.324 |

Determination of the maximum tolerated dose: Nude mice are being injected weekly for four weeks with three doses of oxaliplatin, SM73 and SM85 (3 mice per group) by an intravenous tail-vein injection. From the results of in vitro cytotoxicity experiments, we are selecting the following doses: oxaliplatin (3, 10, 30 mg/kg), SM73 (10, 30, 50 mg/kg), SM85 (30, 50, 90 mg/kg). Toxicity is being determined by: 1) twice weekly body weight measurements, 2) CBC at 2 and 4 weeks, 3) daily visual inspection, 4) liver function test and full serum panel from terminal bleed at the end of the study. Pharmacokinetic parameters for each platinum compound are being determined by measuring platinum blood plasma levels at 0.17, 2, 4, 8, 24 h. Tissue accumulation of platinum is being determined after 48 h of a single bolus intravenous tail-vein injection of each platinum drug.

Tumor Induction: The choice of HEK293 cells for this study is influenced by their modest tumor growth-rates and their well-documented ability to express readily the transfected mammalian proteins. In this study, nude mice are being divided into different treatment groups: 1-4. tumors consisting of HEK293 cells stably expressing OCT1 or OCT2 or OCT3 or NET respectively; 6. tumors consisting of HEK293 cells expressing the vector alone. For these different groups, tumors are being induced by a subcutaneous injection of ~7×10$^6$ HEK293 cells into the flanks of mice. Animals are being maintained in pathogen-free conditions in autoclaved microisolator cages. Serial tumor measurements are being obtained every 3-4 days by a caliper in three dimensions. Tumor volumes are being calculated according to the following formula: volume=height×weight×length×0.5236. Tumors are being allowed to grow for 15 days in both treatment groups or until their mean size approximated 150 mm$^3$.

Drug Treatment and Evaluation: For drug treatment, animals with equal tumor sizes are being divided randomly into four groups: saline, oxaliplatin, SM73 and SM85 (three mice per group). Based on the MTD determined for each of the platinums, animals are being treated by intravenous tail-vein injection of oxaliplatin (10 mg/kg), SM73 (15 mg/kg) and SM85 (30 mg/kg) once a week for four weeks. Body weights and tumor volumes are being measured twice a week. Decrease in the tumor size, expressed as a percentage of the tumor size observed in the group being treated with saline is being regarded as an indicator of the efficacy of these drugs.

Statistical Comparisons: Tumor volumes for each drug treatment are being compared to saline treatment for each tumor type at various time points until sacrifice. ANalysis Of VAriance (ANOVA) is being used to compare within and between treatment groups. A p-value lower than 0.05 is being considered significant.

The main purpose of this efficacy study in OCT1 or OCT2 or OCT3 or NET-expressing xenografts is to verify an improved response, as measured by tumor volume, in the tumor bearing mice treated with oxaliplatin or new platinum leads in comparison to tumor bearing mice treated with saline.

C. Synthesis of Compounds

Overview of Synthetic Schemes:

All compounds were synthesized by directly following the literature procedures or slight modifications of them. Cisplatin, transplatin or potassium tetrachloroplatinate served as starting materials.

Synthesis of Certain Class A Compounds:

Cisplatin was dehalogenated with silver nitrate and the intermediate was then substituted by the desired amine group to obtain subclass I compounds. Following the work of Hollis et al., cisplatin (1.5 mmol) was mixed in dry DMF (8 mL) and the mixture was treated with silver nitrate (1.43 mmol) at ambient temperature. After 24 h, precipitated silver chloride was filtered off and the requisite amine (1.5 mmol) was added in one portion to the filtrate. After incubation of this mixture for 24 h at ambient temperature, it was evaporated to remove most of the solvent and then triturated successively with CH$_2$Cl$_2$ and with Et$_2$O until a TLC spot of the washings showed no response to charring after being dipped in 1% anisaldehyde in ethanol. The solid residue was then recrystallized from methanol to afford the cis-[Pt(NH$_3$)$_2$(Amine)Cl](NO$_3$) products. The color ranged from off-white to yellow. Hollis L S, Amundsen A R, Stern E W. Chemical and biological properties of a new series of Cis-diammineplatinum(II) antitumor agents containing 3 nitrogen donors—Cis-[Pt(NH$_3$)$_2$(N-Donor)Cl]$^+$. J Med. Chem. 1989; 32:128-36.

Scheme 1. Example of synthesis of certain class A platinum compounds. Am may be a composition as described herein.

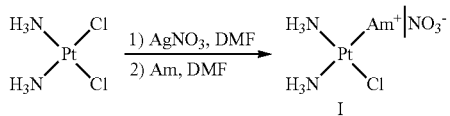

Synthesis of Certain Class B Compounds.

Significant difficulties were met with during the substitution of one of the ammonia ligands in cisplatin with a chloride, resulting in a low yield of the trichloro-amino platinum complex. However, once prepared, a sequence consisting of displacement of one of the chlorides with iodide followed by substitution with a substituted amine trans to the iodide (vide infra), deiodination with Ag$^+$ and replacement with chloride (again, trans to the amine) worked. These compounds were prepared through a modified form of a reported preparative procedure (Giandomenico 1995).

To dimethylacetamide (100 mL, distilled freshly from CaH$_2$) was added Et$_4$NCl.H$_2$O (780 mg, 4.41 mmol) and the mixture was distilled under a pressure of 1 mmHg to remove ca. 20 mL of the solvent. To the remaining pale yellow solution was added cisplatin (1.09 g, 3.66 mmol) and the mixture was stirred at 90° C. under Ar overnight. The resulting solution was then evaporated to ⅓$^{th}$ its volume and poured into ether-hexanes (1:1, 200 mL) and stored at −20° C. overnight, during which an oily residue separated from the mixture. The supernatant was decanted and the oily residue taken up in ca. 15 of water, filtered, and treated with well-swelled Dowex 50W-X8 cationic resin for 2 h. The mixture was filtered, resin washed with 10 mL of water and the combined filtrates where evaporated under 0.5 mmHg to a volume of 1-2 mL. Saturated aqueous KCl (4 mL) was added and the mixture cooled in an ice bath for an hour, resulting in orange crystals, that were collected to afford K[PtCl$_3$NH$_3$].0.5H$_2$O (676 mg, 49%).

To K[Pt$^{II}$Cl$_3$NH$_3$].0.5H$_2$O (100 mg, 0.27 mmol) in water (1 mL) was added sodium iodide (80 mg, 2 equiv, 0.54 mmol) and the requisite Amine (0.41 mmol) (e.g. piperazine or substituted piperazine). After stirring vigorously at ambient temperature overnight, the yellow precipitate was isolated by filtration and triturated with water (10 mL, 3×) and acetone (10 mL, 3×). The solid was then dried under 1 mm Hg to afford Na[PtClIAmineNH$_3$].H$_2$O (84 mg, 67%).

To Na[PtClIAmineNH$_3$].H$_2$O (80 mg) was added AgNO$_3$ (1 equiv) under exclusion of light followed by H$_2$O (5 mL). This mixture was stirred until a test of silver ion was negative. About 1.00 g of activated charcoal was then added and the mixture was filtered after stirring for an hour. HCl (2 mL) was then added, causing precipitation of a solid over 24 h. The solid was collected by filtration, washed with EtOH, EtOAc and then ether, and dried under 0.5 mmHg to afford 68 mg (51%) of Na[PtCl$_2$-AmineNH$_3$]. Giandomenico C M, Abrams M J, Murrer, B A, et al. Carboxylation of kinetically inert platinum (IV) hydroxy complexes. An entree into orally active platinum(IV) antitumor agents. Inorg Chem 1995; 34:1015-21.

Synthesis of Certain Class C Compounds followed a literature protocol (Scheme 2). Synthesis of subclass VI compounds followed the procedure used for subclass I compounds, with the exception of transplatin being the starting material. Procedures followed for class C compounds were adapted (Najajreh 2002).

Scheme 2. Example of synthesis of certain class C platinum compounds. Am may be a composition as described herein, Am is depicted with a positive charge; however, Am may also be neutral.

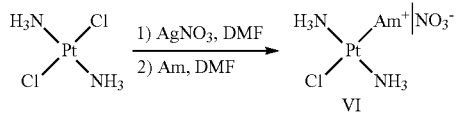

The procedure is analogous to that for the preparation of Class A compounds. Najajreh Y, Perez J M, Navarro-Ranninger C, Gibson D. Novel soluble cationic trans-diaminedichloroplatinum (II) complexes that are active against cisplatin resistant ovarian cancer cell lines. J Med Chem 2002; 45: 5189-95.

All compounds were verified by $^1$H NMR and their homogeneity was ascertained through elemental analysis, with less than 0.4% of deviation in the expected and experimental values being regarded as proof of purity (Table 10).

TABLE 10

Combustion analysis data for platinum compounds.

| | |
|---|---|
| SM71 | Expected C (24.57%), H (4.12%), N (14.33%) |
| | Found C (24.25%), H (4.50%), N (14.14%) |
| SM73 | Expected C (26.98%), H (3.85%), N (9.44%) |
| | Found C (27.03%), H (4.20%), N (9.53%) |
| SM85 | Expected C (25.93%), H (3.48%), N (9.07%) |
| | Found C (26.03%), H (3.25%), N (8.75%) |
| SM39 | Expected C (24.93%), H (3.77%), N (8.72%) |
| | Found C (24.75%), H (3.71%), N (8.70%) |
| SM78 | Expected C (24.57%), H (4.12%), N (14.33%) |
| | Found C (24.44%), H (4.50%), N (14.17%) |

D. Characterization of Platinum-Based Compounds

To determine the OCT1 specificity and cytotoxicity of the platinum-based compounds by comparing the cytotoxicity, uptake, and DNA adduct formation in cells transfected with OCT1 versus untransfected cells. Compounds synthesized were evaluated in three types of in vitro experiments: 1) cytotoxicity assay, 2) platinum uptake assay, 3) platinum-DNA adducts quantitation assay.

Overview of Methods:

In these studies, oxaliplatin and platinum-based compounds described herein were exposed to hOCTs transfected HEK cell lines to determine their cytotoxicity. Platinum uptake and platinum-DNA adduct formation was then measured in these transfected cell lines. In some cases, chemical inhibitors of OCT1 were used. In general, we used disopyramide (150 μM). At this concentration, disopyramide has been shown to completely inhibit the uptake of model organic cations by OCT1. Furthermore, at this concentration, it is selective for OCT1 over OCT2. In some cases, cimetidine (3 mM) was used as a general OCT inhibitor. Cytotoxicity of some of the leads was determined in colon cancer cell lines. Described below in some detail are the methods for these studies.

TABLE 6

Cytotoxicity of synthetic platinum analogs in colon cancer cell lines in presence and absence of an OCT inhibitor, cimetidine (3 mM). Resistance factor is expressed as the ratio of IC50 value of platinums in presence and absence of cimetidine.

| | Platinum Compounds IC50 μMLine | | |
|---|---|---|---|
| Colon Cancer Cell | Oxaliplatin | SM73 | SM85 |
| HCT116 | 6.14 ± 1.80 | 18.34 ± 2.28 | 54.5 ± 10.6 |
| (in presence of cimetidine) | (66.5 ± 14.6) | (71.2 ± 10.0) | (364 ± 15.8) |
| Resistance Factor | 10.8 | 3.88 | 6.67 |
| RKO | 2.90 ± 0.77 | 19.6 ± 1.17 | 55.0 ± 20.0 |
| (in presence of cimetidine) | (41.7 + 9.75) | (75.8 + 9.35) | (305 ± 31.3) |
| Resistance Factor | 14.3 | 3.87 | 5.54 |
| DLD | 21.5 ± 5.30 | 48.9 ± 8.50 | 132 ± 28.3 |
| (in presence of cimetidine) | (151 ± 12.6) | (195 ± 19.4) | (>600 pM) |
| Resistance Factor | 7.02 | 3.98 | >5 |
| HT29 | 13.2 ± 3.30 | 14.5 ± 8.54 | 43.04 ± 11.5 |
| (in presence of cimetidine) | (61.2 ± 6.88) | (109 ± 8.95) | (>600 mtv1) |
| Resistance Factor | 4.63 | >7 | >13 |
| SW620 | 7.16 ± 3.59 | 33.03 ± 5.27 | 57.4 ± 14.4 |
| (in presence of cimetidine) | (40.0 ± 0.53) | (147 ± 10.3) | (286 ± 28.3) |
| Resistance Factor | 5.71 | 4.45 | 4.98 |

Cell Lines and Culture:

HEK293 cell lines, stably expressing hOCT1, hOCT2 and hOCT3. The following colon cancer cell lines were also used: HCT116, RKO, DLD, HT29 and SW620 purchased from American Type Tissue Culture collection.

Cytotoxicity Studies:

The cytotoxicity of oxaliplatin/platinum-based compounds described herein was measured by standard MTT (thiazolyl blue tetrazolium bromide) assays in 96-well plates. After overnight incubation, the platinum compound with or without an OCT inhibitor (disopyramide) was then be added to the culture medium to various concentrations. After exposure to the drug for 7 hours, the drug-containing medium was replaced with fresh, drug-free medium and the incubation was continued for 72 hours. The $IC_{50}$ (the drug concentration that inhibits 50% of cell growth) values were obtained by fitting the percent of the maximal cell growth at different drug concentrations (F) to the equation, $F=100\times(1-C^\gamma/(IC_{50}^\gamma+C^\gamma)$, using WinNonlin (Pharsight, Mountain View, Calif.). The maximal cell growth is considered to be the cell growth in the medium without any platinum compounds; C is the concentration of the platinum compound and $\gamma$ is the slope factor.

Cellular Accumulation of Platinum:

The cells were incubated in the culture medium containing 10 μM concentrations of oxaliplatin or synthetic platinum analogs with or without an OCT1 inhibitor, disopyramide. Cell pellets obtained after centrifugation were dissolved in 70% nitric acid. Distilled water containing 10 ppb of iridium (Sigma) and 0.1% Triton X-100 was then added. The platinum content was measured by inductively coupled plasma mass spectrometry (ICP-MS) in the Analytical Facility at University of California at Santa Cruz. Accumulation was normalized to protein content.

Platinum-DNA Adduct Formation:

The cells were incubated in the culture medium containing 10 μM concentration of oxaliplatin or platinum-based compounds with or without an OCT inhibitor. After incubation, genomic DNA was isolated from the cell pellets using Wizard® Genomic DNA Purification Kit (Promega, Madison, Wis.) following the manufacturer's instructions. The genomic DNA was used for determination of platinum (ICP-MS) and DNA content (absorption spectrometry at 260 nm). Platinum-DNA adduct formation was expressed as amount of platinum per amount of DNA.

Rate of Inactivation of Platinums by Glutathione:

Platinum-based compound as described herein at a 100 μM concentration was reacted with physiological concentration of GSH and the absorption at 260 nm was measured to monitor the progress of the reaction. Absorption as a function of time ($0 \le t \le 1440$ min) for platinum concentration of zero was subtracted from the absorption at each platinum concentration. Initial rates were calculated from the early time points as change in absorption over change in time.

Statistics:

In the studies using OCT transfected cells, comparisons of $IC_{50}$, uptake and platinum DNA adduct formation was performed between OCTs expressing cells and control (empty vector transfected cells). In the colon cancer cell lines, the same comparisons were made in the presence and absence of disopyramide. Standard t-tests will be used with a p value set at 0.05 (two-tailed).

Evaluation of all three classes of compounds was carried out in an in-vitro cytotoxicity assay, involving a comparison between the effect of the platinum complex on human embryonic kidney cells (HEK293) transfected with human OCT1 (HEK-hOCT1) and OCT2 (HEK-hOCT2) versus those that are not transfected. The results indicated that the positively charged complexes are superior substrates for OCT1 and OCT2 than oxaliplatin itself. The $IC_{50}$ values of these newly synthesized complexes were 20-170 times lower in OCT transfected cell lines when compared with untransfected cells. Cytotoxicities of individual member of platinum complex classes A, B and C are listed in table 2, 3 and 4. From this preliminary cytotoxicity data, the identified lead platinum-based compounds as described herein were: SM73 and SM85 (10).

Concrete evidence for the higher accumulation of platinum-based compounds is obtained through a comparison of the cellular uptake of lead platinum compounds vs. oxaliplatin in OCT1 or OCT2 or OCT3 or NET transfected and untransfected cells. A 50-100 fold higher accumulation of new platinum compounds, when compared to the 4.5-fold higher accumulation of oxaliplatin in HEK-OCT1 cells than untransfected cells serves to confirm the abovesaid supposition (FIG. 11). These experiments clearly demonstrate that platinum-based compounds designed to target hOCT1 were far better substrates of hOCT1 when compared to oxaliplatin and could indeed be used as targeted anticancer therapy.

Similar results were obtained for the entire series of our synthetic platinum complexes (tables 6, 7, and 8). Also, most of these complexes were found to be substrates for OCT2 (tables 6 and 7). This greatly substantiates our original proposition of the stereoelectronic mimicry of the bioactive mono-aqua complex to achieve higher affinity for OCTs.

To further support our results from experiments in transfected cell lines, we will demonstrate anticancer efficacy of oxaliplatin and these platinum-based compounds as described herein in colon cancer cell lines or neuroendocrine cancer cell lines or other cancer cell lines that express and OCT or NET, or another transporter that translocates the compounds described herein.

Besides these in vitro experiments which demonstrate the importance of OCT1 in the pharmacological efficacy of these platinums, we carried out a mechanistic study whereby we compared the rates of inactivation of these lead synthetic platinums with that of cisplatin and oxaliplatin. One major pathway by which these platinum drugs get inactivated in vivo is by reaction with glutathione (GSH). We mimicked this reaction with GSH in vitro using physiological concentrations of GSH and salts. Increase in absorption at 260 nm over period of time was monitored for progress of the reaction and initial rates were calculated from the early time points in terms of the change in absorption over change in time.

TABLE 7

Initial rate of reaction of synthetic platinum analogs with glutathione.

| Platinum Drug (100 μM) | [GSH] mM | [NaCl] mM | Initial Rate Absorption unit/hr | R |
|---|---|---|---|---|
| Cisplatin | 6.75 | 4.62 | 0.1173 | >0.99 |
| Oxaliplatin | 6.75 | 4.62 | 0.0909 | >0.99 |
| SM73 | 6.75 | 4.62 | 0.1132 | >0.98 |
| SM85 | 6.75 | 4.62 | 0.1037 | >0.99 |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

EMBODIMENTS

Embodiment 1

A compound having the formula:

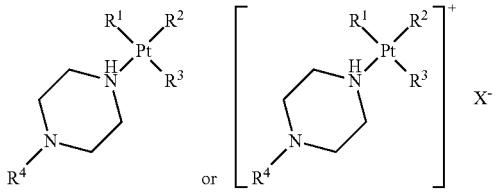

wherein, X⁻ is a counterion; $R^1$, $R^2$, and $R^3$ are independently halogen, —$SR^9$, —$OSO_2R^8$, —$OSO_3H$, —$NH_2NH_2$, —$ONR^6R^7$, —$NH_2C$=(O)$NHNH_2$, —$NH_2C$=(O)$NR^6R^7$, —$NR^5R^6R^7$, —$OC(O)R^8$, —$OC(O)NR^6R^7$, —$OR^9$, substituted or unsubstituted heteroalkyl, substituted or unsubstituted heterocycloalkyl, or substituted or unsubstituted heteroaryl, with the proviso $R^1$, $R^2$, and $R^3$ are attached to the Pt atom through an atom that is not a carbon atom, wherein $R^1$ and $R^2$, $R^2$ and $R^3$ or $R^1$ and $R^3$ may optionally be joined to form a substituted or unsubstituted heterocycloalkyl or substituted or unsubstituted heteroaryl; $R^4$ is substituted or unsubstituted cycloalkyl, substituted or unsubstituted heterocycloalkyl, substituted or unsubstituted aryl, or substituted or unsubstituted heteroaryl; $R^5$, $R^6$, $R^7$, $R^8$, and $R^9$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^5$ and $R^6$, $R^6$ and $R^7$, or $R^5$ and $R^7$, may optionally be joined to form, in combination with their commonly bonded nitrogen, a substituted or unsubstituted heterocycloalkyl or substituted or unsubstituted heteroaryl.

Embodiment 2

The compound of embodiment 1, wherein $R^1$ is —$SR^9$, —$OSO_2R^8$, —$OSO_3H$, —$NH_2NH_2$, —$ONR^6R^7$, —$NH_2C$=(O)$NHNH_2$, —$NH_2C$=(O)$NR^6R^7$, —$NR^5R^6R^7$, —$OC(O)R^8$, —$OC(O)NR^6R^7$, —$OR^9$, substituted or unsubstituted heteroalkyl, substituted or unsubstituted heterocycloalkyl, or substituted or unsubstituted heteroaryl, with the proviso $R^1$ is attached to the Pt atom through an atom that is not a carbon atom; and $R^2$ and $R^3$ are independently halogen.

Embodiment 3

The compound of embodiment 2 wherein $R^1$ is —$NH_3$.

Embodiment 4

The compound of embodiment 2, wherein $R^2$ and $R^3$ are independently —Cl.

Embodiment 5

The compound of embodiment 1, wherein $R^2$ is —$SR^9$, —$OSO_2R^8$, —$OSO_3H$, —$NH_2NH_2$, —$ONR^6R^7$, —$NH_2C$=(O)$NHNH_2$, —$NH_2C$=(O)$NR^6R^7$, —$NR^5R^6R^7$, —$OC(O)R^8$, —$OC(O)NR^6R^7$, —$OR^9$, substituted or unsubstituted heteroalkyl, substituted or unsubstituted heterocycloalkyl, or substituted or unsubstituted heteroaryl, with the proviso $R^2$ is attached to the Pt atom through an atom that is not a carbon atom; and $R^1$ and $R^3$ are independently halogen.

Embodiment 6

The compound of embodiment 5, wherein $R^2$ is —$NH_3$.

Embodiment 7

The compound of embodiment 5, wherein $R^1$ and $R^3$ are independently —Cl.

Embodiment 8

The compound of embodiment 1, wherein $R^1$ and $R^2$ are independently —$SR^9$, —$OSO_2R^8$, —$OSO_3H$, —$NH_2NH_2$, —$ONR^6R^7$, —$NH_2C$=(O)$NHNH_2$, —$NH_2C$=(O)$NR^6R^7$, —$NR^5R^6R^7$, —$OC(O)R^8$, —$OC(O)NR^6R^7$, —$OR^9$, substituted or unsubstituted heteroalkyl, substituted or unsubstituted heterocycloalkyl, or substituted or unsubstituted heteroaryl, with the proviso $R^1$ and $R^2$ are attached to the Pt atom through an atom that is not a carbon atom; and $R^3$ is halogen.

Embodiment 9

The compound of embodiment 8, wherein $R^1$ and $R^2$ are independently —$NH_3$.

Embodiment 10

The compound of embodiment 8, wherein $R^3$ is —Cl.

Embodiment 11

The compound of embodiment 1, wherein $R^1$ and $R^3$ are independently —$SR^9$, —$OSO_2R^8$, —$OSO_3H$, —$NH_2NH_2$, —$ONR^6R^7$, —$NH_2C$=(O)$NHNH_2$, —$NH_2C$=(O)$NR^6R^7$, —$NR^5R^6R^7$, —$OC(O)R^8$, —$OC(O)NR^6R^7$, —$OR^9$, substituted or unsubstituted heteroalkyl, substituted or unsubstituted heterocycloalkyl, or substituted or unsubstituted heteroaryl, with the proviso $R^1$ and $R^3$ are attached to the Pt atom through an atom that is not a carbon atom; and $R^2$ is halogen.

Embodiment 12

The compound of embodiment 11, wherein $R^1$ and $R^3$ are independently —$NH_3$.

Embodiment 13

The compound of embodiment 11, wherein $R^2$ is —Cl.

Embodiment 14

The compound of embodiment 1, wherein $R^4$ is substituted or unsubstituted aryl or substituted or unsubstituted heteroaryl.

Embodiment 15

The compound of embodiment 14, wherein $R^4$ is substituted or unsubstituted aryl.

Embodiment 16

The compound of embodiment 15, wherein $R^4$ is substituted or unsubstituted phenyl.

Embodiment 17

The compound of embodiment 16, wherein $R^4$ is unsubstituted phenyl.

Embodiment 18

The compound of embodiment 16, wherein $R^4$ is substituted phenyl.

Embodiment 19

The compound of embodiment 18, having the formula:

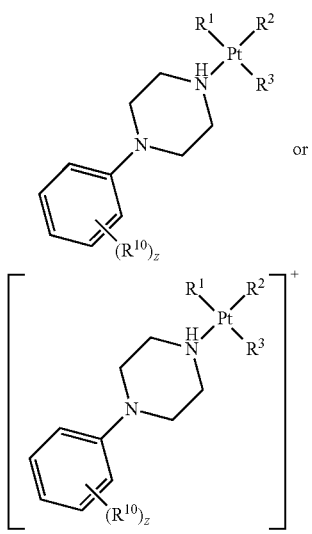

wherein, $R^{10}$ is independently halogen, —$CY_3$, —CN, —$SO_2Cl$, —$SO_qR^{14}$, —$SO_uNR^{11}R^{12}$, —$NHNH_2$, —$ONR^{11}R^{12}$, —$NHC=(O)NHNH_2$, —$NHC=(O)NR^{11}R^{12}$, —$N(O)_m$, —$C(O)R^{13}$, —$C(O)—OR^{13}$, —$C(O)NR^{11}R^{12}$, —$OR^{14}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^{10}$ substituents may optionally be joined to form a substituted or unsubstitued cycloalkyl, substituted or unsubstituted heterocycloalkyl, substituted or unsubstituted aryl, or substituted or unsubstituted heteroaryl; $R^{11}$, $R^{12}$, $R^{13}$, and $R^{14}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; z is an integer from 0 to 5; u is independently an integer from 1 to 2; m is independently an integer from 1 to 2; q is independently an integer from 0 to 4; Y is independently —Cl, —Br, —I, or —F.

Embodiment 20

The compound of embodiment 19, wherein $R^{10}$ is independently halogen.

Embodiment 21

The compound of embodiment 20, wherein $R^{10}$ is independently —F.

Embodiment 22

The compound of embodiment 21, wherein z is 1.

Embodiment 23

The compound of embodiment 22, having the formula:

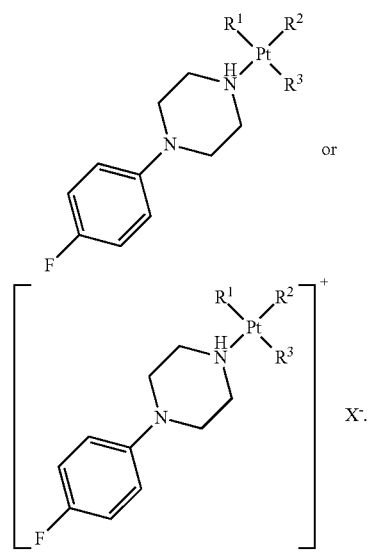

Embodiment 24

The compound of embodiment 23, having the formula:

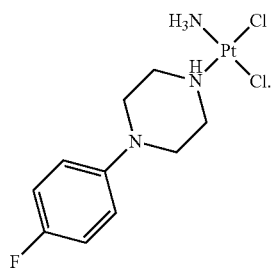

Embodiment 25

The compound of embodiment 17, having the formula:

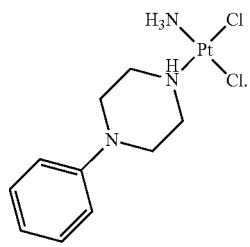

Embodiment 26

A pharmaceutical composition comprising a pharmaceutically acceptable excipient and a compound of any one of embodiments 1 to 25 or a pharmaceutically acceptable salt thereof.

Embodiment 27

A method of treating a disease in a patient in need of such treatment, said method comprising administering a therapeutically effective amount of a compound having the formula:

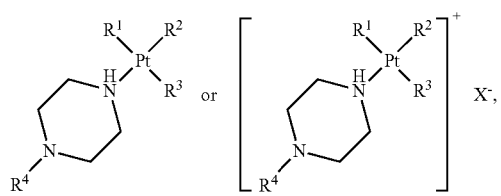

wherein, $X^-$ is a counterion; $R^1$, $R^2$, and $R^3$ are independently halogen, —$SR^9$, —$OSO_2R^8$, —$OSO_3H$, —$NH_2NH_2$, —$ONR^6R^7$, —$NH_2C=(O)NHNH_2$, —$NH_2C=(O)NR^6R^7$, —$NR^5R^6R^7$, —$OC(O)R^8$, —$OC(O)NR^6R^7$, —$OR^9$, substituted or unsubstituted heteroalkyl, substituted or unsubstituted heterocycloalkyl, or substituted or unsubstituted heteroaryl, with the proviso $R^1$, $R^2$, and $R^3$ are attached to the Pt atom through an atom that is not a carbon atom, wherein $R^1$ and $R^2$, $R^2$ and $R^3$ or $R^1$ and $R^3$ may optionally be joined to form a substituted or unsubstituted heterocycloalkyl or substituted or unsubstituted heteroaryl; $R^4$ is substituted or unsubstituted cycloalkyl, substituted or unsubstituted heterocycloalkyl, substituted or unsubstituted aryl, or substituted or unsubstituted heteroaryl; $R^5$, $R^6$, $R^7$, $R^8$, and $R^9$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^5$ and $R^6$, $R^6$ and $R^7$, or $R^5$ and $R^7$, may optionally be joined to form, in combination with their commonly bonded nitrogen, a substituted or unsubstituted heterocycloalkyl or substituted or unsubstituted heteroaryl.

Embodiment 28

The method of embodiment 27, wherein the disease is cancer.

Embodiment 29

The method of embodiment 28, wherein said cancer is colorectal cancer, liver cancer, hepatocarcinoma, renal cancer, renal cell carcinoma, bladder cancer, lung cancer, non-small cell lung cancer, ovarian cancer, uterine cancer, cervical cancer, testicular cancer, anal cancer, bile duct cancer, biliary tract cancer, gastrointestinal carcinoid tumors, esophageal cancer, gall bladder cancer, appendix cancer, small intestine cancer, stomach (gastric) cancer, urinary bladder cancer, genitourinary tract cancer, endometrial cancer, head and neck cancer, nasopharyngeal cancer, head and neck squamous cell carcinoma, mesothelioma, lymphoma, leukemia, breast cancer, or prostate cancer.

Embodiment 30

The method of any one of embodiments 27 to 29, wherein said patient has disease-related cells expressing an organic cation transporter.

Embodiment 31

The method of any one of embodiments 27 to 29, further comprising a method of measuring the amount of an organic cation transporter in a sample from the patient.

Embodiment 32

The method of embodiment 31, wherein said sample comprises disease-related cells.

Embodiment 33

The method of embodiment 32, wherein said cells express an organic cation transporter.

Embodiment 34

The method of embodiment 29, wherein the cancer is liver cancer.

Embodiment 35

The method of embodiment 29, wherein the cancer is renal cancer.

Embodiment 36

The method of embodiment 27, wherein the compound is a compound of any one of embodiments 1 to 25.

Embodiment 37

A method of inhibiting replication of DNA in a cell, wherein said method comprises contacting said cell with the compound of formula:

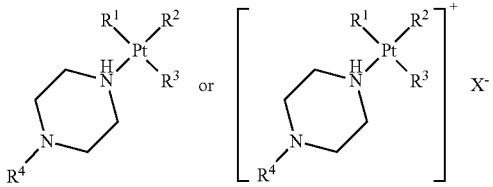

wherein, $X^-$ is a counterion; $R^1$, $R^2$, and $R^3$ are independently halogen, —$SR^9$, —$OSO_2R^8$, —$OSO_3H$, —$NH_2NH_2$, —$ONR^6R^7$, —$NH_2C=(O)NHNH_2$, —$NH_2C=(O)NR^6R^7$, —$NR^5R^6R^7$, —$OC(O)R^8$, —$OC(O)NR^6R^7$, —$OR^9$, substituted or unsubstituted heteroalkyl, substituted or unsubstituted heterocycloalkyl, or substituted or unsubstituted heteroaryl, with the proviso $R^1$, $R^2$, and $R^3$ are attached to the Pt atom through an atom that is not a carbon atom, wherein $R^1$ and $R^2$, $R^2$ and $R^3$ or $R^1$ and $R^3$ may optionally be joined to form a substituted or unsubstituted heterocycloalkyl or substituted or unsubstituted heteroaryl; $R^4$ is substituted or unsubstituted cycloalkyl, substituted or unsubstituted heterocycloalkyl, substituted or unsubstituted aryl, or substituted or unsubstituted heteroaryl; $R^5$, $R^6$, $R^7$, $R^8$, and $R^9$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^5$ and $R^6$, $R^6$ and $R^7$, or $R^5$ and $R^7$, may optionally be joined to form, in combination with their commonly bonded nitrogen, a substituted or unsubstituted heterocycloalkyl or substituted or unsubstituted heteroaryl.

Embodiment 38

The method of embodiment 37, wherein the compound is a compound of any one of embodiments 1 to 25.

Embodiment 39

A method of inducing cell death in a cell, wherein said method comprises contacting said cell with the compound of formula:

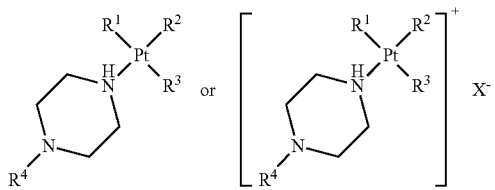

wherein, $X^-$ is a counterion; $R^1$, $R^2$, and $R^3$ are independently halogen, $-SR^9$, $-OSO_2R^8$, $-OSO_3H$, $-NH_2NH_2$, $-ONR^6R^7$, $-NH_2C=(O)NHNH_2$, $-NH_2C=(O)NR^6R^7$, $-NR^5R^6R^7$, $-OC(O)R^8$, $-OC(O)NR^6R^7$, $-OR^9$, substituted or unsubstituted heteroalkyl, substituted or unsubstituted heterocycloalkyl, or substituted or unsubstituted heteroaryl, with the proviso $R^1$, $R^2$, and $R^3$ are attached to the Pt atom through an atom that is not a carbon atom, wherein $R^1$ and $R^2$, $R^2$ and $R^3$ or $R^1$ and $R^3$ may optionally be joined to form a substituted or unsubstituted heterocycloalkyl or substituted or unsubstituted heteroaryl; $R^4$ is substituted or unsubstituted cycloalkyl, substituted or unsubstituted heterocycloalkyl, substituted or unsubstituted aryl, or substituted or unsubstituted heteroaryl; $R^5$, $R^6$, $R^7$, $R^8$, and $R^9$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^5$ and $R^6$, $R^6$ and $R^7$, or $R^5$ and $R^7$, may optionally be joined to form, in combination with their commonly bonded nitrogen, a substituted or unsubstituted heterocycloalkyl or substituted or unsubstituted heteroaryl.

Embodiment 40

The method of embodiment 39, wherein the compound is a compound of any one of embodiments 1 to 25.

Embodiment 41

The method of embodiment 37 or 39, wherein said cell expresses an organic cation transporter.

Embodiment 42

A method of treating a disease in a patient in need of such treatment, said method comprising administering a therapeutically effective amount of a compound having the formula:

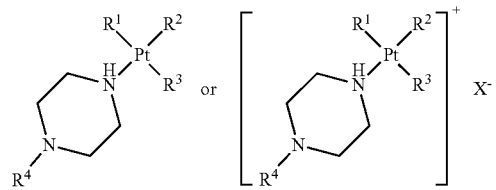

wherein, $X^-$ is a counterion; $R^1$, $R^2$, and $R^3$ are independently halogen, $-SR^9$, $-OSO_2R^8$, $-OSO_3H$, $-NH_2NH_2$, $-ONR^6R^7$, $-NH_2C=(O)NHNH_2$, $-NH_2C=(O)NR^6R^7$, $-NR^5R^6R^7$, $-OC(O)R^8$, $-OC(O)NR^6R^7$, $-OR^9$, substituted or unsubstituted heteroalkyl, substituted or unsubstituted heterocycloalkyl, or substituted or unsubstituted heteroaryl, with the proviso $R^1$, $R^2$, and $R^3$ are attached to the Pt atom through an atom that is not a carbon atom, wherein $R^1$ and $R^2$, $R^2$ and $R^3$ or $R^1$ and $R^3$ may optionally be joined to form a substituted or unsubstituted heterocycloalkyl or substituted or unsubstituted heteroaryl; $R^4$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^5$, $R^6$, $R^7$, $R^8$, and $R^9$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^5$ and $R^6$, $R^6$ and $R^7$, or $R^5$ and $R^7$, may optionally be joined to form, in combination with their commonly bonded nitrogen, a substituted or unsubstituted heterocycloalkyl or substituted or unsubstituted heteroaryl; wherein said patient has disease-related cells expressing a norepinephrine transporter protein or mRNA.

Embodiment 43

The method of embodiment 42, wherein the disease is cancer.

Embodiment 44

The method of embodiment 43, wherein the cancer is glioblastoma multiforme, neuroblastoma, glioma, neuroendocrine cancer, or brain cancer.

Embodiment 45

The method of embodiment 42, wherein the compound is a compound of any one of embodiments 1 to 25.

Embodiment 46

The method of any one of embodiments 42 to 44, further comprising a method of measuring the amount of a norepinephrine transporter protein or mRNA in a sample from the patient.

Embodiment 47

The method of embodiment 46, wherein said sample comprises disease-related cells.

Embodiment 48

The method of embodiment 47, wherein said cells express a norepinephrine transporter protein or mRNA.

Embodiment 49

A method of inhibiting replication of DNA in a cell, wherein said method comprises contacting said cell with the compound of formula:

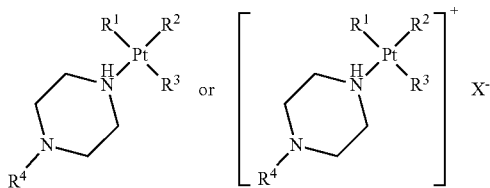

wherein, X⁻ is a counterion; $R^1$, $R^2$, and $R^3$ are independently halogen, —$SR^9$, —$OSO_2R^8$, —$OSO_3H$, —$NH_2NH_2$, —$ONR^6R^7$, —$NH_2C$=(O)$NHNH_2$, —$NH_2C$=(O)$NR^6R^7$, —$NR^5R^6R^7$, —$OC(O)R^8$, —$OC(O)NR^6R^7$, —$OR^9$, substituted or unsubstituted heteroalkyl, substituted or unsubstituted heterocycloalkyl, or substituted or unsubstituted heteroaryl, with the proviso $R^1$, $R^2$, and $R^3$ are attached to the Pt atom through an atom that is not a carbon atom, wherein $R^1$ and $R^2$, $R^2$ and $R^3$ or $R^1$ and $R^3$ may optionally be joined to form a substituted or unsubstituted heterocycloalkyl or substituted or unsubstituted heteroaryl; $R^4$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^5$, $R^6$, $R^7$, $R^8$, and $R^9$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^5$ and $R^6$, $R^6$ and $R^7$, or $R^5$ and $R^7$, may optionally be joined to form, in combination with their commonly bonded nitrogen, a substituted or unsubstituted heterocycloalkyl or substituted or unsubstituted heteroaryl; wherein said cell expresses a norepinephrine transporter protein or mRNA.

Embodiment 50

The method of embodiment 49, wherein the compound is a compound of any one of embodiments 1 to 25.

Embodiment 51

A method of inducing cell death in a cell, wherein said method comprises contacting said cell with the compound of formula:

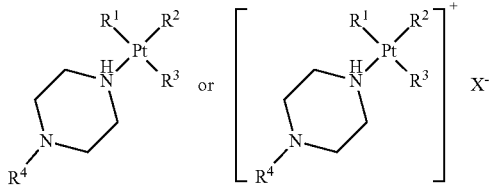

wherein, X⁻ is a counterion; $R^1$, $R^2$, and $R^3$ are independently halogen, —$SR^9$, —$OSO_2R^8$, —$OSO_3H$, —$NH_2NH_2$, —$ONR^6R^7$, —$NH_2C$=(O)$NHNH_2$, —$NH_2C$=(O)$NR^6R^7$, —$NR^5R^6R^7$, —$OC(O)R^8$, —$OC(O)NR^6R^7$, —$OR^9$, substituted or unsubstituted heteroalkyl, substituted or unsubstituted heterocycloalkyl, or substituted or unsubstituted heteroaryl, with the proviso $R^1$, $R^2$, and $R^3$ are attached to the Pt atom through an atom that is not a carbon atom, wherein $R^1$ and $R^2$, $R^2$ and $R^3$ or $R^1$ and $R^3$ may optionally be joined to form a substituted or unsubstituted heterocycloalkyl or substituted or unsubstituted heteroaryl; $R^4$ is substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^5$, $R^6$, $R^7$, $R^8$, and $R^9$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^5$ and $R^6$, $R^6$ and $R^7$, or $R^5$ and $R^7$, may optionally be joined to form, in combination with their commonly bonded nitrogen, a substituted or unsubstituted heterocycloalkyl or substituted or unsubstituted heteroaryl; wherein said cell expresses a norepinephrine transporter protein or mRNA.

Embodiment 52

The method of embodiment 51, wherein the compound is a compound of any one of embodiments 1 to 25.

What is claimed is:
1. A compound having the formula:

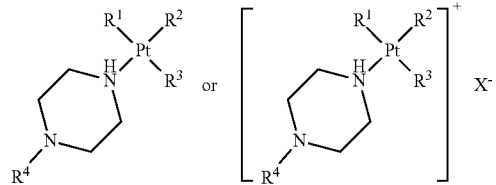

wherein,
X⁻ is a counterion;
$R^1$, $R^2$, and $R^3$ are independently halogen, —$SR^9$, —$OSO_2R^8$, —$OSO_3H$, —$NH_2NH_2$, —$ONR^6R^7$, —$NH_2C$=(O)$NHNH_2$, —$NH_2C$=(O)$NR^6R^7$, —$NR^5R^6R^7$, —$OC(O)R^8$, —$OC(O)NR^6R^7$, —$OR^9$, substituted or unsubstituted heteroalkyl, substituted or unsubstituted heterocycloalkyl, or substituted or unsubstituted heteroaryl, with the proviso $R^1$, $R^2$, and $R^3$ are attached to the Pt atom through an atom that is not a carbon atom, wherein $R^1$ and $R^2$, $R^2$ and $R^3$ or $R^1$ and $R^3$ may optionally be joined to form a substituted or unsubstituted heterocycloalkyl or substituted or unsubstituted heteroaryl;

$R^4$ is substituted or unsubstituted cycloalkyl, substituted or unsubstituted heterocycloalkyl, substituted or unsubstituted aryl, or substituted or unsubstituted heteroaryl;

$R^5$, $R^6$, $R^7$, $R^8$, and $R^9$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^5$ and $R^6$, $R^6$ and $R^7$, or $R^5$ and $R^7$, may optionally be joined to form, in combination with their commonly bonded nitrogen, a substituted or unsubstituted heterocycloalkyl or substituted or unsubstituted heteroaryl.

2. The compound of claim 1, wherein $R^1$ and $R^2$ are independently —$SR^9$, —$OSO_2R^8$, —$OSO_3H$, —$NH_2NH_2$, —$ONR^6R^7$, —$NH_2C$=(O)$NHNH_2$, —$NH_2C$=(O)$NR^6R^7$, —$NR^5R^6R^7$, —$OC(O)R^8$, —$OC(O)NR^6R^7$, —$OR^9$, substituted or unsubstituted heteroalkyl, substituted or unsubstituted heterocycloalkyl, or substituted or unsubstituted heteroaryl, with the proviso $R^1$ and $R^2$ are attached to the Pt atom through an atom that is not a carbon atom; and
$R^3$ is halogen.

3. The compound of claim 2, wherein $R^1$ and $R^2$ are independently
—$NH_3$.

4. The compound of claim 2, wherein $R^3$ is —Cl.

5. The compound of claim 1, wherein $R^1$ and $R^3$ are independently
—$SR^9$, —$OSO_2R^8$, —$OSO_3H$, —$NH_2NH_2$, —$ONR^6R^7$, —$NH_2C$=(O)$NHNH_2$, —$NH_2C$=(O)$NR^6R^7$, —$NR^5R^6R^7$, —$OC(O)R^8$, —$OC(O)NR^6R^7$, —$OR^9$, substituted or unsubstituted heteroalkyl, substituted or unsubstituted heterocycloalkyl, or substituted or unsubstituted heteroaryl, with the proviso $R^1$ and $R^3$ are attached to the Pt atom through an atom that is not a carbon atom; and
$R^2$ is halogen.

6. The compound of claim 5, wherein $R^1$ and $R^3$ are independently —$NH_3$.

7. The compound of claim 5, wherein $R^2$ is —Cl.

8. The compound of claim 1, wherein $R^4$ is substituted or unsubstituted aryl or substituted or unsubstituted heteroaryl.

9. The compound of claim 8, wherein $R^4$ is substituted or unsubstituted phenyl.

10. The compound of claim 1, having the formula:

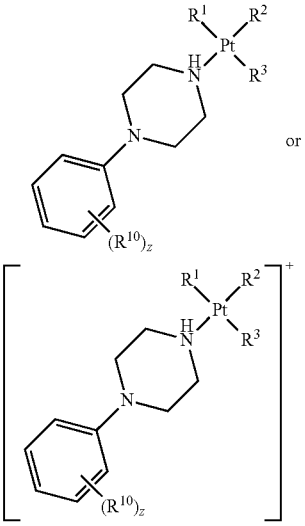

wherein,
$R^{10}$ is independently halogen, —$CY_3$, —CN, —$SO_2Cl$, —$SO_qR^{14}$, —$SO_uNR^{11}R^{12}$, —$NHNH_2$, —$ONR^{11}R^{12}$, —$NHC$=(O)$NHNH_2$, —$NHC$=(O)$NR^{11}R^{12}$, —$N(O)_m$, —$NRR^{12}$, —C(O)$R^{13}$, —C(O)—$OR^{13}$, —C(O)$NR^{11}R^{12}$, —$OR^{14}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

two adjacent $R^{10}$ substituents may optionally be joined to form a substituted or unsubstituted cycloalkyl, substituted or unsubstituted heterocycloalkyl, substituted or unsubstituted aryl, or substituted or unsubstituted heteroaryl;
$R^{11}$, $R^{12}$, $R^{13}$, and $R^{14}$ are independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
z is an integer from 0 to 5;
u is independently an integer from 1 to 2;
m is independently an integer from 1 to 2;
q is independently an integer from 0 to 4;
Y is independently —Cl, —Br, —I, or —F.

11. The compound of claim 10, having the formula:

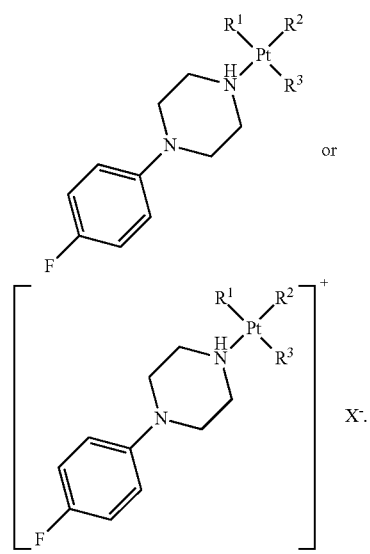

12. The compound of claim 11, having the formula:

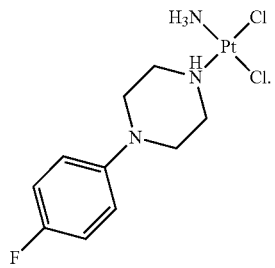

13. The compound of claim 9, having the formula:

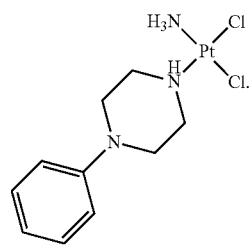

14. A pharmaceutical composition comprising a pharmaceutically acceptable excipient and a compound of claim 1 or a pharmaceutically acceptable salt thereof.

15. A method of inhibiting replication of DNA in a cell, wherein said method comprises contacting said cell with the compound of claim 1.

16. A method of inducing cell death in a cell, wherein said method comprises contacting said cell with the compound of claim 1.

* * * * *